US009913878B2

(12) United States Patent
Cochran et al.

(10) Patent No.: US 9,913,878 B2
(45) Date of Patent: *Mar. 13, 2018

(54) ENGINEERED INTEGRIN BINDING PEPTIDE COMPOSITIONS

(71) Applicant: The Board of Trustees of the Leland Stanford Junior University, Stanford, CA (US)

(72) Inventors: Jennifer R. Cochran, Stanford, CA (US); Richard H. Kimura, Menlo Park, CA (US); Aron M. Levin, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 45 days.

This patent is subject to a terminal disclaimer.

(21) Appl. No.: 15/007,091

(22) Filed: Jan. 26, 2016

(65) Prior Publication Data
US 2016/0206692 A1  Jul. 21, 2016

Related U.S. Application Data

(60) Continuation of application No. 14/028,348, filed on Sep. 16, 2013, now Pat. No. 9,265,845, which is a division of application No. 12/418,376, filed on Apr. 3, 2009, now Pat. No. 8,536,301, which is a continuation-in-part of application No. PCT/US2007/021218, filed on Oct. 3, 2007.

(60) Provisional application No. 60/849,259, filed on Oct. 4, 2006.

(51) Int. Cl.
| A61K 38/01 | (2006.01) |
| A61K 38/17 | (2006.01) |
| C07K 14/47 | (2006.01) |
| A61K 49/00 | (2006.01) |
| A61K 51/08 | (2006.01) |
| G01N 33/574 | (2006.01) |
| A61K 38/06 | (2006.01) |
| A61K 38/08 | (2006.01) |
| A61K 45/06 | (2006.01) |

(52) U.S. Cl.
CPC .......... *A61K 38/1709* (2013.01); *A61K 38/06* (2013.01); *A61K 38/08* (2013.01); *A61K 45/06* (2013.01); *A61K 49/0056* (2013.01); *A61K 51/082* (2013.01); *C07K 14/47* (2013.01); *G01N 33/57492* (2013.01)

(58) Field of Classification Search
None
See application file for complete search history.

(56) References Cited

U.S. PATENT DOCUMENTS

| 4,789,734 A | 12/1988 | Pierschbacher |
| 4,792,525 A | 12/1988 | Ruoslahti et al. |
| 4,879,237 A | 11/1989 | Rudslahti et al. |
| 4,988,621 A | 1/1991 | Ruoslahti et al. |
| 5,169,930 A | 12/1992 | Ruoslahti et al. |
| 5,519,005 A | 5/1996 | Lider et al. |
| 5,536,814 A | 7/1996 | Ruoslahti et al. |
| 5,695,997 A | 12/1997 | Ruoslahti et al. |
| 5,766,591 A | 6/1998 | Brooks et al. |
| 5,827,821 A | 10/1998 | Pierschbacher et al. |
| 5,880,092 A | 3/1999 | Pierschbacher et al. |
| 5,916,875 A | 6/1999 | Ruoslahti et al. |
| 5,981,468 A | 11/1999 | Pierschbacher et al. |
| 5,981,478 A | 11/1999 | Ruoslahti et al. |
| 5,994,501 A | 11/1999 | Ruoslahti et al. |
| 6,020,460 A | 2/2000 | Pierschbacher et al. |
| 6,180,610 B1 | 1/2001 | Ruoslahti et al. |
| 6,265,539 B1 | 7/2001 | Arlinghaus |
| 6,353,090 B1 | 3/2002 | Pierschbacher et al. |
| 6,451,976 B1 | 9/2002 | Lu et al. |
| 6,962,974 B1 | 11/2005 | Kalluri |
| 8,536,301 B2 * | 9/2013 | Cochran ................ C07K 14/47 530/324 |
| 9,265,845 B2 * | 2/2016 | Cochran ................ C07K 14/47 |
| 2002/0018780 A1 | 2/2002 | Koenig et al. |
| 2004/0132659 A1 | 7/2004 | Markland, Jr. et al. |
| 2004/0146976 A1 | 7/2004 | Wittrup et al. |
| 2005/0075323 A1 | 4/2005 | Day et al. |
| 2005/0164300 A1 | 7/2005 | Artis et al. |
| 2005/0196427 A1 | 9/2005 | Tirrell et al. |
| 2006/0029544 A1 | 2/2006 | Sutcliffe-Goulden et al. |
| 2010/0267610 A1 | 10/2010 | Blind et al. |
| 2017/0304342 A1 * | 10/2017 | Cox ................ A61K 47/48246 |

FOREIGN PATENT DOCUMENTS

WO  2008045252 A2  4/2008

OTHER PUBLICATIONS

Ana Segura, et al., "Snakin-1, a peptide from potato that is active against plant pathogens," MPMI, 1999, vol. 12, 16-23.

(Continued)

*Primary Examiner* — Maher M Haddad
(74) *Attorney, Agent, or Firm* — Brian E. Davy; Bozicevic, Field & Francis LLP

(57) ABSTRACT

Engineered peptides that bind with high affinity (low equilibrium dissociation constant (Kd)) to the cell surface receptors of fibronectin ($\alpha_5\beta_1$) or vitronectin ($\alpha_v\beta_3$ and $\alpha_v\beta_5$ integrins) are disclosed as useful as imaging tissue. These peptides are based on a molecular scaffold into which a subsequence containing the RGD integrin-binding motif has been inserted. The subsequence (RGD mimic) comprises about 9-13 amino acids, and the RGD contained within the subsequence can be flanked by a variety of amino acids, the sequence of which was determined by sequential rounds of selection (in vitro evolution). The molecular scaffold is preferably based on a knottin, e.g., EETI (Trypsin inhibitor 2 (Trypsin inhibitor II) (EETI-II) [*Ecballium elaterium* (Jumping cucumber)], AgRP (Agouti-related protein), and Agatoxin IVB, which peptides have a rigidly defined three-dimensional conformation. It is demonstrated that EETI tolerates mutations in other loops and that the present peptides may be used as imaging agents.

18 Claims, 14 Drawing Sheets

(56) References Cited

OTHER PUBLICATIONS

Jean-Christophe Gelly, et al., "The Knottin website and database: a new information system dedicated to the knottin scaffold," Nucleic Acids Research, 2004, vol. 32, D156-D159.

Andreas Christmann, et al., "The cystine knot of a squash-type protease inhibitor as a structural scaffold for *Escherichia coli* cell surface display of conformationally constrained peptides," Protein Engineering, 1999, vol. 12, 797-806.

FlowJo, Data analysis software for flow cytometry, User Documentation tutorial, Version 3.4, Apr. 2001.

Joseph C. McNulty, et al., "High-resolution NMR structure of the chemically-synthesized melanocortin receptor binding domain AGRP(87-132) of the agouti-related protein," Biochemistry, 2001, vol. 40, 15520-15527.

Valerie Copie, et al., "Solution structure and dynamics of linked cell attachment modules of mouse fibronectin containing the RGD and synergy regions: comparison with the human fibronectin crystal structure," J. Mol. Biol., 1998, vol. 277, 663-682.

Norelle L. Daly, et al., "Disulfide folding pathways of cystine know proteins," J. Biol. Chem., 2003, vol. 278, 6314-6322.

Aarno Hautanen, et al., "Effects of modifications of the RGD sequence and its context on recognition by the fibronectin receptor," J. Biol. Chem., 1989, vol. 264, 1437-1442.

C. S. Elangbam, et al., "Cell adhesion molecules—update," Vet Pathol, 1997, 34,61-73.

Leonore A. Herzenberg, et al., "Intepreting flow cytometry data: a guide for the perplexed," Nature Immunology, 2006, vol. 7, 681-685.

Shuang Liu, "Radiolabeled multimeric cyclic RGD peptides as integrin αvβ3 targeted radiotracers for tumor imaging," Molecular Pharmaceutics, 2006, vol. 3, 472-487.

Arne Skerra, "Engineered protein scaffolds for molecular recognition," J. Mol. Recognition, 2000, vol. 13, 167-187.

Beth Wattam, et al., "Arg-Tyr-Asp (RYD) and Arg-Cys-Asp (RCD) motifs in dendroaspin promote selective inhibition of β1 and β3 integrins," Biochem. J., 2001, vol. 356, 11-17.

Ralf J. Hosse, et al., "A new generation of protein display scaffolds for molecular recognition," Protein Science, 2006, vol. 15, 14-27.

Geoffrey P. Smith, et al., "Small binding proteins selected from a combinatorial repertoire of knottins displayed on phage," J. Mol. Biol., 1998, vol. 277, 317-332.

Robert M. Scarborough, et al., "Characterization of the integrin specificities of disintegrins isolated from american pit viper venoms," J. Biol. Chem., 1993, vol. 268, 1058-1065.

Thomas J. Kunicki, et al., "The exchange of Arg-Gly-Asp (RGD) and Arg-Tyr-Asp (RYD) binding sequences in a recombinant murine Fab fragment specific for the integrin αIIbβ3 does not alter integrin recognition," J. Biol. Chem., 1995, vol. 270, 16660-16665.

Herren Wu, et al., "Stepwise in vitro affinity maturation of vitaxin, an αvβ3-specific humanized mAb," PNAS, 1998, vol. 95, 6037-6042.

Victor M. Garsky, et al., "Chemical synthesis of echistatin, a potent inhibitor of platelet aggregation from Echis carinatus: synthesis and biological activity of selected analogs," PNAS, 1989, vol. 86, 4022-4026.

Sandy Reiss, et al., "Inhibition of platelet aggregation by grafting RGD and KGD sequences on the structural scaffold of small disulfide-rich proteins," Platelets, 2006, vol. 17, 153-157.

Richard H. Kimura, et al., "Engineered knottin peptides: A new class of agents for imaging integrin expression in living subjects," Cancer Research, 2009, vol. 69, 2435-2442.

Alexander Wentzel, et al., "Sequence requirements of the GPNG beta-turn of the Ecballium elaterium trypsin inhibitor II explored by combinatorial library screening," J. Biol. Chem., 1999, vol. 274, 21037-21043.

Erkki Koivunen, et al., "Phage libraries displaying cyclic peptides with different ring sizes: ligand specificities of the RGD-directed integrins," Nature Biotechnology, 1995, vol. 13, 265-270.

Peter C. Brooks, et al., "Requirement of vascular integrin αvβ3 for angiogenesis," Science, 1994, vol. 264, 569-571.

A. Favel, et al., "Protease inhibitors from Ecballium elaterium seeds," Int. J. Peptide Protein Res., 1989, vol. 33, 202-208.

Timothy Hla, et al., "Human cyclooxygenase-2 cDNA," PNAS, 1992, vol. 89, 7384-7388.

PCT International Search Report for application PCT/US 07/21218 dated May 29, 2008.

Koivunen, et al., "Identification of receptor ligands with phage display peptide libraries", J. Nucl. Med.; 40:883-888, 1999.

Lu, et al., "Preferential antagonism of the interactions of the integrin alpha IIb beta 3 with immobilized glycoprotein ligands by snake-venom RGD (Arg-Gly-Asp) proteins . . . snake-venom RGD proteins", 1994, Biochem J 304: 929-936.

Attwood, "Genomics. The Babel of bioinformatics", Science. 290(5491):471-473, 2000.

Skolnick, et al., "From genes to protein structure and function: novel applications of computational approaches in the genomic era," Trends Biotechnol. 18(1):34-9, 2000.

Kuntz, "Structure-based strategies for drug design and discovery," Science, 1992, 257(5073):1078-1082.

Miller, et al., "Ligand binding to proteins: the binding landscape model", Protein Sci. Oct. 1997:6(10):2166-79.

Li, et al., "Use of phage display to probe the evolution of binding specificity and affinity in integrins", Protein Engineering vol. 16, No. 1, pp. 65-72, 2003.

\* cited by examiner

Fig. 3A

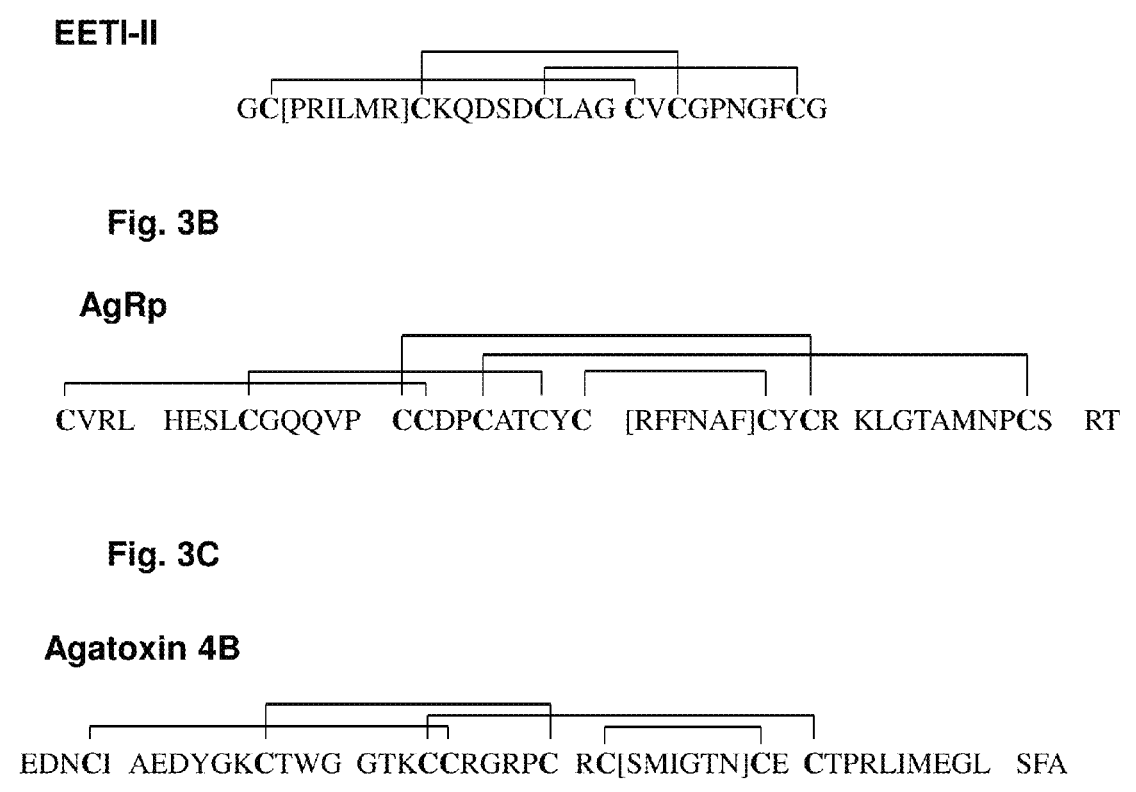

EETI-II

GC[PRILMR]CKQDSDCLAG CVCGPNGFCG

Fig. 3B

AgRp

CVRL HESLCGQQVP CCDPCATCYC [RFFNAF]CYCR KLGTAMNPCS RT

Fig. 3C

Agatoxin 4B

EDNCI AEDYGKCTWG GTKCCRGRPC RC[SMIGTN]CE CTPRLIMEGL SFA

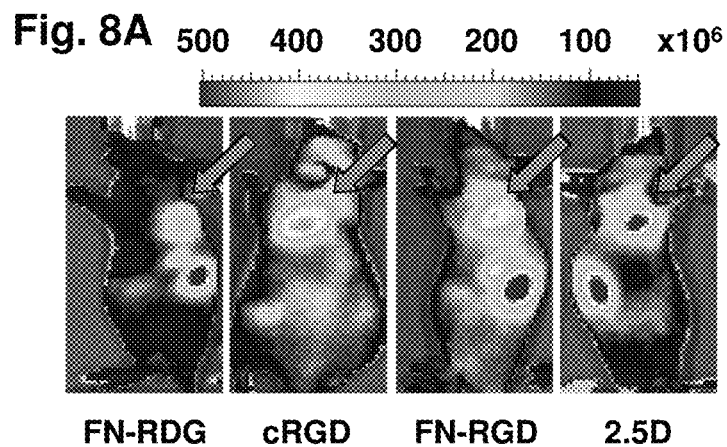
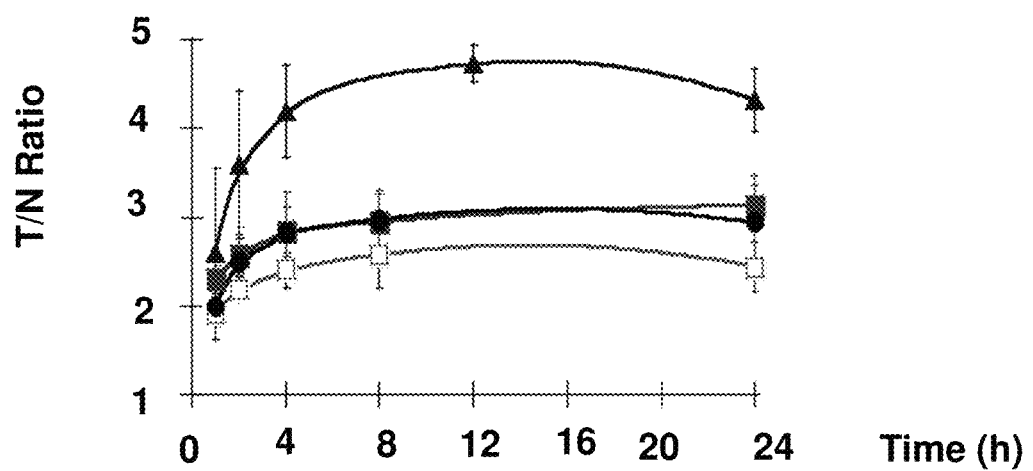

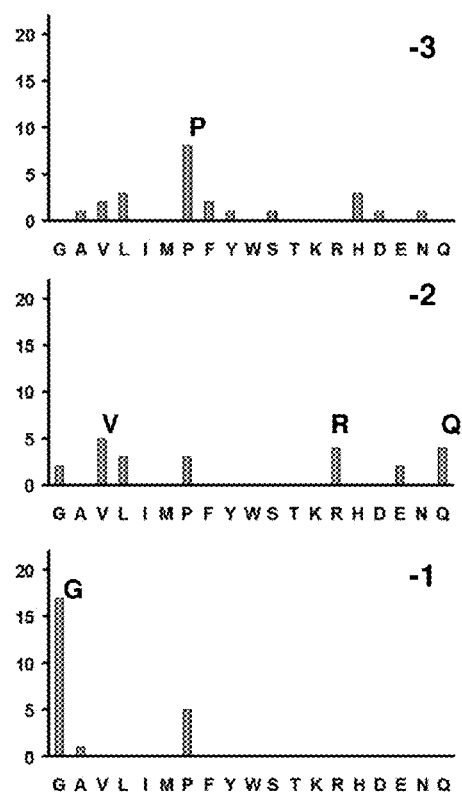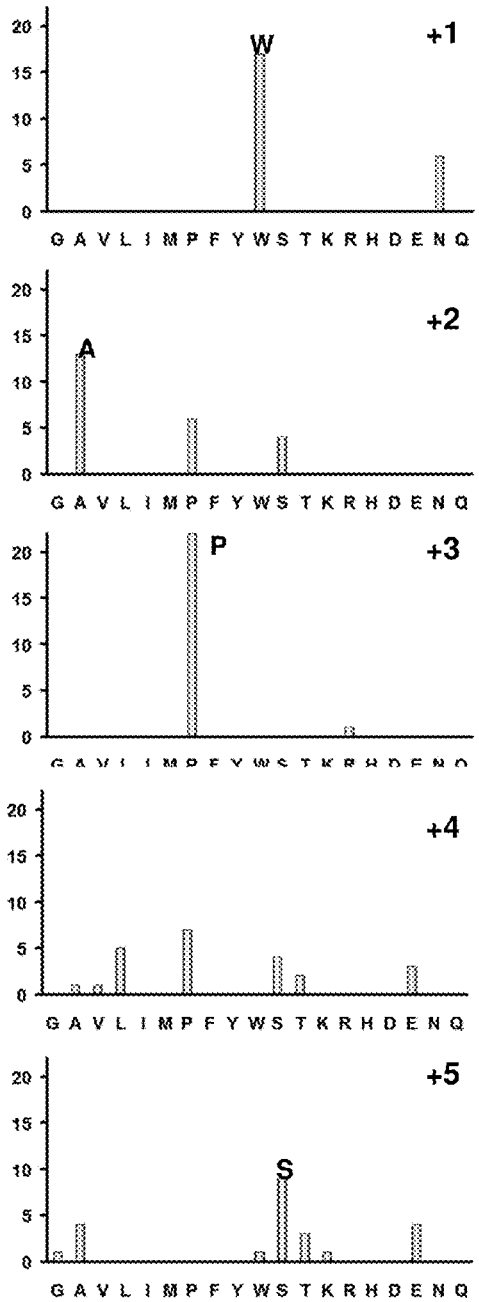
Fig. 11

ENGINEERED INTEGRIN BINDING PEPTIDE COMPOSITIONS

CROSS-REFERENCE TO RELATED APPLICATIONS

This application is a continuation of U.S. patent application Ser. No. 14/028,348 filed on Sep. 16, 2013, which is a divisional application of U.S. patent application Ser. No. 12/418,376 filed on Apr. 3, 2009, now U.S. Pat. No. 8,536,301 issued on Sep. 17, 2013, which is a continuation in part to PCT/US2007/021218, filed on Oct. 3, 2007, which claims priority to U.S. Provisional Patent Application No. 60/849,259 filed on Oct. 4, 2006, all of which are hereby incorporated by reference in their entirety.

STATEMENT OF GOVERNMENTAL SUPPORT

This invention was made with Government support under contract 5K01CA104706 awarded by the National Institutes of Health. The Government has certain rights in the invention.

In accordance with "Legal Framework for EFS-Web," (6 Apr. 2011) Applicants submit herewith a sequence listing as an ASCII text file. The text file will serve as both the paper copy required by 37 CFR 1.821(c) and the computer readable form (CRF) required by 37 CFR 1.821(e). The date of creation of the file was Sep. 16, 2013, and the size of the ASCII text file in bytes is 21,580. Applicants incorporate the contents of the sequence listing by reference in its entirety.

BACKGROUND OF THE INVENTION

Field of the Invention

The present invention relates to the field of engineered peptides, and to the field of peptides which bind to integrins, and, particularly to integrin binding as it relates to cell growth and development.

Related Art

Integrins are a family of extracellular matrix adhesion proteins that noncovalently associate into $\alpha$ and $\beta$ heterodimers with distinct cellular and adhesive specificities (Hynes, 1992; Luscinskas and Lawler, 1994). Cell adhesion, mediated though integrin-protein interactions, is responsible for cell motility, survival, and differentiation. Each $\alpha$ and $\beta$ subunit of the integrin receptor contributes to ligand binding and specificity.

Protein binding to many different cell surface integrins can be mediated through the short peptide motif Arg-Gly-Asp (RGD) (Pierschbacher and Ruoslahti, 1984). These peptides have dual functions: They promote cell adhesion when immobilized onto a surface, and they inhibit cell adhesion when presented to cells in solution. Adhesion proteins that contain the RGD sequence include: fibronectin, vitronectin, osteopontin, fibrinogen, von Willebrand factor, thrombospondin, laminin, entactin, tenascin, and bone sialoprotein (Ruoslahti, 1996). The RGD sequence displays specificity to about half of the 20 known integrins including the $\alpha_5\beta_1$, $\alpha_8\beta_1$, $\alpha_v\beta_1$, $\alpha_v\beta_3$, $\alpha_v\beta_5$, $\alpha_v\beta_6$, $\alpha_v\beta_8$, and $\alpha_{iiib}\beta_3$ integrins, and, to a lesser extent, the $\alpha_2\beta_1$, $\alpha_3\beta_1$, $\alpha_4\beta_1$, and $\alpha_7\beta_1$ integrins (Ruoslahti, 1996). In particular, the $\alpha_v\beta_3$ integrin is capable of binding to a large variety of RGD containing proteins including fibronectin, fibrinogen, vitronectin, osteopontin, von Willebrand factor, and thrombospondin (Ruoslahti, 1996; Haubner et al., 1997), while the $\alpha_5\beta_1$ integrin is more specific and has only been shown to bind to fibronectin (D'Souza et al., 1991).

The linear peptide sequence RGD has a much lower affinity for integrins than the proteins from which it is derived (Hautanen et al., 1989). This due to conformational specificity afforded by folded protein domains not present in linear peptides. Increased functional integrin activity has resulted from preparation of cyclic RGD motifs, alteration of the residues flanking the RGD sequence, and synthesis of small molecule mimetics (reviewed in (Ruoslahti, 1996; Haubner et al., 1997)).

The X-ray crystal structure of the 10th type III domain of fibronectin (Dickinson et al., 1994), and the NMR solution structures of the murine 9th and 10th type III fibronection domains (Copie et al., 1998) containing the RGD sequence have been solved. In these structures, the GRGDSP (SEQ ID NO: 105) amino acid sequence makes a type II $\beta$-hairpin turn that protrudes from the rest of the fibronectin structure for interaction with integrin receptors.

Short RGD peptides also have been shown to assume a type II $\beta$-turn in aqueous solution, as determined by NMR (Johnson et al., 1993). Conformation and stereochemistry about the RGD motif in the form of cyclic penta- and hexa-peptides, and disulfide-constrained peptides have been studied extensively (reviewed in (Haubner et al., 1997)). Previous approaches have shown that combinations of natural and unnatural amino acids, peptidomimetics, or disulfide bonds flanking the RGD motif have been necessary to create high affinity, biologically active $\beta$-turn structures. The recent structure of an RGD $\beta$-loop mimic bound to $\alpha_v\beta_3$ (Xiong et al., 2002) has shed some interesting light on the nature of the ligand-receptor interaction and has validated the body of work encompassing the ligand-based design strategy.

Previously, phage display technology has been used to isolate cyclic peptides specific to different integrin receptors. When a random linear hexapeptide library displayed on phage was panned with immobilized integrin, the amino acid sequence CRGDCL (SEQ ID NO: 1) was isolated (Koivunen et al., 1993). It was determined that this peptide was 10-fold more potent than linear RGD hexapeptides in inhibiting the binding of attachment of $\alpha_5\beta_1$ expressing cells to fibronectin (Koivunen et al., 1993). This cyclic peptide also inhibited cell adhesion mediated by $\alpha_v\beta_1$, $\alpha_v\beta_3$, and $\alpha_v\beta_5$ integrins. In another study, phage display was used to isolate selective ligands to the $\alpha_5\beta_1$, $\alpha_v\beta_3$, $\alpha_v\beta_5$, and $\alpha_{IIb}\beta_3$ integrins from phage libraries expressing cyclic peptides (Koivunen et al., 1995). It was determined that each of the four integrins studied primarily selected RGD-containing sequences, but preferred different ring sizes and flanking residues around the RGD motif. A cyclic peptide, ACRGDGWCG (SEQ ID NO: 2), was isolated that bound with high affinity to the $\alpha_5\beta_1$ integrin. In addition, the cyclic peptide ACDCRGDCFCG (SEQ ID NO: 3), which contains two disulfide bonds, was shown to be 20-fold more effective in inhibiting cell adhesion mediated by the $\alpha_v\beta_3$ and $\alpha_v\beta_5$ integrins than comparable peptides with one disulfide bond, and 200-fold more potent than linear RGD peptides.

Phage display has also been used to isolate novel integrin binding motifs from peptide libraries. The cyclic peptide CRRETAWAC (SEQ ID NO: 4) was identified from a random heptapeptide phage library with flanking cystine residues (Koivunen et al., 1994). This peptide was specific for binding to the $\alpha_5\beta_1$ integrin, and not the $\alpha_v\beta_3$ and $\alpha_v\beta_5$ integrins, and was determined to have an overlapping binding site with the RGD sequence. The peptide NGRAHA (SEQ ID NO: 5) was identified by phage display libraries as well (Koivunen et al., 1993), but it was later determined that the receptor for this peptide was aminopeptidase N, and not integrins as originally thought (Pasqualini et al., 2000). A synergistic binding site on the 10th domain of fibronectin (encompassing the sequence RNS) also enhances RGD binding to the $\alpha_5\beta_1$ integrin (Koivunen et al., 1994; Obara and Yoshizato, 1995). In addition, the sequence PHSRN (SEQ ID NO: 6) (from the 9th domain of fibronectin), increases $\alpha_5\beta_1$ integrin binding to the RGD peptide in fibronectin (Aota et al., 1994). The sequence ACGSAGTCSPHLRRP (SEQ ID NO: 7) was identified from a 15-mer phage library panned with $\alpha_v\beta_3$ integrin. The SAGT (SEQ ID NO: 139) tetrapeptide is found in the sequence of vitronectin, suggesting that this may be an accessory site for integrin recognition and binding (Healy et al., 1995). It has been hypothesized that other synergy sites may exist (reviewed in Ruoslahti, 1996), suggesting that random peptide library screening for integrin ligands other than RGD would be useful.

The presentation of multiple RGD motifs within one molecule has been shown to increase integrin binding affinity and activity. Numerous studies have demonstrated that multivalent clustering of RGD ligands within a polymer coated surface or bead results in enhanced cell adhesion, due to increased local concentration of ligand, or increased ligand/receptor avidity. (Miyamoto et al., 1995; Maheshwari et al., 2000; Pierschbacher et al., 1994; Shakesheff et al., 1998). Soluble RGD repeats incorporated into polypeptides (Saiki, 1997), or linked through a poly(carboxyethylmethacrylamide) backbone (Komazawa et al., 1993) have demonstrated an increased potential for inhibition of cancer metastasis compared to free peptide. More recently, soluble multivalent polymers of GRGD (SEQ ID NO: 8), and copolymers of GRGD (SEQ ID NO: 8) and the $\alpha_5\beta_1$ synergy peptide SRN have been prepared synthetically through ring-opening metathesis (Maynard et al., 2001). Homopolymers containing GRGD (SEQ ID NO: 8) peptides were more potent inhibitors of fibronectin cell adhesion ($IC_{50}$=0.18 mM) than peptide alone ($IC_{50}$=1.08 mM). Heteropolymers containing both GRGD (SEQ ID NO: 8) and SRN peptides exhibited an enhanced ability to block fibronectin adhesion with an $IC_{50}$ of 0.03 mM (Maynard et al., 2001). Although multivalent homo- and hetero-oligomers of integrin peptides demonstrated increased inhibition of cell adhesion, improvements in affinity and efficacy are contemplated through the use of multivalent frameworks.

The growth of new blood vessels, termed angiogenesis, plays an important role in development, wound healing, and inflammation (Folkman and Shing, 1992). Angiogenesis has been implicated in proliferative disease states such as rheumatoid arthritis, cancer, and diabetic retinopathy, and therefore is a relevant and attractive target for therapeutic intervention. In cancer, the growth and survival of solid tumors is dependent on their ability to trigger new blood vessel formation to supply nutrients to the tumor cells (Folkman, 1992). With this new tumor vascularization comes the ability to release tumor cells into the circulation leading to metastases. One specific approach to anti-angiogenic therapy is to inhibit cell adhesion events in endothelial cells. The $\alpha_v\beta_3$ (Brooks et al., 1994) and $\alpha_v\beta_5$ integrins (Friedlander et al., 1995), and more recently the $\alpha_5\beta_1$ integrin (Kim et al., 2000), have been shown to be required for angiogenesis in vascular cells. Brooks and colleagues demonstrated that the $\alpha_v\beta_3$ integrin was abundantly expressed on blood vessels, but not on dermis or epithelial cells, and expression was upregulated on vascular tissue during angiogenesis (Brooks et al., 1994). In addition, the $\alpha_v\beta_1$ integrin has been shown to be expressed on the tumor vasculature of breast, ovarian, prostate, and colon carcinomas, but not on normal adult tissues or blood vessels (Kim et al., 2000). The $\alpha_v\beta_3$ (and $\alpha_v\beta_5$) integrins are highly expressed on many tumor cells such as osteosarcomas, neuroblastomas, carcinomas of the lung, breast, prostate, and bladder, as well as glioblastomas, and invasive melanomas (reviewed in (Haubner et al., 1997). It has also been demonstrated that the expression levels of $\alpha_v\beta_3$ and $\alpha_v\beta_5$ by the vascular endothelium of neuroblastoma was associated with the aggressiveness of the tumor (Erdreich-Epstein et al., 2000).

A monoclonal anti-$\alpha_v\beta_3$ antibody (LM609) was shown to inhibit angiogenesis by fibroblast growth factor (FGF), tumor necrosis factor-a, and human melanoma fragments (Brooks et al., 1994). The humanized version of LM609, termed Vitaxin, has been shown to suppress tumor growth in animal models (Brooks et al., 1995), and target angiogenic blood vessels (Sipkins et al., 1998). Vitaxin has undergone Phase I clinical trials in humans and appears to be safe and potentially active in disease stabilization (Gutheil et al., 2000). In another study, function-blocking anti-$\alpha_5\beta_1$ monoclonal antibodies were shown to inhibit cell adhesion to fibronectin, and inhibit FGF-induced angiogenesis in vivo (Kim et al., 2000). In addition, RGD peptides selective to $\alpha_v$ (Pasqualini et al., 1997) and $\alpha_5\beta_1$ integrins (Kim et al., 2000) are relevant targets for imaging and therapeutic purposes. Bacteriophage displaying an RGD peptide (CD-CRGDCFC) (SEQ ID NO: 9) with high affinity to $\alpha_v$ integrins was shown to localize to tumor blood vessels when injected into tumor-bearing mice (Ruoslahti, 2000). In other approaches, RGD containing peptides and peptidomimetics have demonstrated promise in cancer therapy by binding to overexpressed cell surface integrins and interfering with angiogenesis and tumor blood supply. Inhibition of $\alpha_v\beta_3$ and $\alpha_v\beta_5$ integrins by cyclic RGD peptides resulted in significant reduction of functional blood vessel density, and was shown to impair tumor growth and metastasis in vivo (Brooks et al., 1994; Buerkle et al., 2002). In addition, the cyclic peptide c(RGDfV) (SEQ ID NO: 10) was shown to cause $\alpha_v\beta_3$-mediated apoptosis in human malignant glioma cells (Chatterjee et al., 2000) and prostate cancer cells (Chatterjee et al., 2001). The cyclic peptide antagonist CRRETAWAC (SEQ ID NO: 11), and the nonpeptide antagonist SJ749, were shown to selectively inhibit $\alpha_5\beta_1$-mediated cell adhesion to fibronectin, as well as block FGF-induced angiogenesis in vivo (Kim et al., 2000). Of particular interest, the integrin inhibitors seem to have no effect on normal vessels, and appear to function by specifically inducing apoptosis in newly budding endothelial cells during angiogenesis (Brooks et al., 1994), and interfering with the function of metalloproteinase enzymes required for cellular invasion (Brooks et al., 1996).

Radiolabeled integrin antagonists as described below are useful in tumor targeting and imaging applications. Noninvasive methods to visualize and quantify integrin expression in vivo are crucial for clinical applications of integrin antagonists (Brower, 1999). The first generation of radioiodinated cyclic RGD peptides exhibited high affinity and specificity in vitro and in vivo for $\alpha_v\beta_3$ integrins however, exhibited rapid excretion and accumulation in the liver and intestines, limiting their application (Haubner et al., 1999). Modifications of these peptides with a sugar moiety reduced their uptake in the liver, and increased their accumulation in $\alpha_v\beta_3$-expressing tumors in vivo (Haubner et al., 2001). Noninvasive imaging with an $^{18}$F-labeled version of this glycoRGD peptide by positron emission tomography demonstrated receptor-specific binding and high tumor to background ratios in vivo, suggesting suitability for $\alpha_v\beta_3$ quantification and therapy (Haubner et al., 2001). In addition, RGD peptides coupled to chelating agents could be radiolabeled with $^{111}$In, $^{125}$I, $^{90}$Y and $^{177}$Lu, enlarging their potential for both tumor imaging and radionuclide therapy (van Hagen et al., 2000). Integrin-specific antibodies can also be useful for imaging applications. Paramagnetic liposomes coated with the anti $\alpha_v\beta_3$ integrin antibody LM609 were used for detailed imaging of rabbit carcinomas for a noninvasive means to asses growth and malignancy of tumors (Sipkins et al., 1998). The small integrin binding proteins described below would therefore be very amenable to coupling to a variety of radionuclides and chemotherapeutic agents.

Patents and Publications

Ruoslahti et al., have obtained a series of patents relating to RGD peptides. For example, U.S. Pat. No. 5,695,997, entitled "Tetrapeptide," relates to a method of altering cell attachment activity of cells, comprising: contacting the cells with a substantially pure soluble peptide including RGDX where X is any amino acid and the peptide has cell attachment activity. The patent further includes an embodiment where X is any amino acid and the peptide has cell attachment activity and the peptide has less than about 31 amino acids.

Similarly, U.S. Pat. No. 4,792,525 relates to a substantially pure peptide including as the cell-attachment-promoting constituent the amino acid sequence Arg-Gly-Asp-R wherein R is Ser, Cys, Thr or other amino acid, said peptide having cell-attachment promoting activity, and said peptide not being a naturally occurring peptide.

U.S. Pat. No. 5,169,930, to Ruoslahti, et al., relates to a substantially pure integrin receptor characterized in that it consists of an $\alpha_v\beta_1$ subunit.

U.S. Pat. No. 5,536,814, to Ruoslahti, et al., entitled "Integrin-binding peptides," issued Jul. 16, 1996, discloses a purified synthetic peptide consisting of certain specified amino acid sequences.

U.S. Pat. No. 5,519,005, to Ofer et al., relates to certain non-peptidic compounds comprising a guanidino and a carboxyl terminal groups with a spacer sequence of 11 atoms between them, which are effective inhibitors of cellular or molecular interactions which depend on RXD or DGR recognition, wherein X is G (gly), E (glu), Y (tyr), A (ala) or F (phe). These RXD and DGR analogues are referred to as "RXD surrogates."

US 2005/0164300 to Artis, et al., published Jul. 28, 2005, entitled "Molecular scaffolds for kinase ligand development," discloses molecular scaffolds that can be used to identify and develop ligands active on one or more kinases, for example, the PIM kinases, (e.g., PIM-1, PIM-2, and PIM-3).

U.S. Pat. No. 6,451,976, to Lu et al., discloses a process in which dendroaspin, a polypeptide neurotoxin analogue, is modified by recombinant DNA techniques, particularly "loop grafting," to provide a modified polypeptide.

U.S. Pat. No. 6,962,974, to Kalluri et al., issued Nov. 8, 2005, discloses recombinantly-produced Tumstatin, comprising the NC1 domain of the $\alpha$3 chain of Type IV collagen, having anti-angiogenic activity, anti-angiogenic fragments of the isolated Tumstatin, multimers of the isolated Tumstatin and anti-angiogenic fragments, and polynucleotides encoding those anti-angiogenic proteins.

U.S. Pat. No. 5,766,591, to Brooks et al., relates to a method of inducing solid tumor regression comprising administering an RGD-containing integrin $\alpha_v\beta 3$ antagonist.

U.S. Pat. No. 5,880,092 to Pierschbacher et al., relates to a substantially pure compound comprising an Arg-Gly-Asp sequence stereochemically stabilized through a bridge and having a molecular weight less than about 5.4 kilodaltons.

U.S. Pat. No. 5,981,468 to Pierschbacher et al., relates to a compound having a stabilized stereochemical conformation of a cyclic RGD peptide.

Koivunen et al., "Phage Libraries Displaying Cyclic Peptides with Different Ring Sizes: Ligand Specificities of the RGD-Directed Integrins," *Bio/Technology* 13:265-270 (1995) discloses selective ligands to the cell surface receptors of fibronectin ($\alpha_5\beta_1$ integrin), vitronectin (($\alpha_v\beta_3$ integrin and $\alpha_v\beta_5$ integrin and fibrinogen (($\alpha_m\beta_3$ integrin from phage libraries expressing cyclic peptides. A mixture of libraries was used that express a series of peptides flanked by a cystine residue on each side (CX5C, CX6C, CX7C) or only on one side (CX9) of the insert.

Reiss et al., "Inhibition of platelet aggregation by grafting RGD and KGD sequences on the structural scaffold of small disulfide-rich proteins," *Platelets* 17(3):153-7 (May 2006) discloses RGD and KGD containing peptide sequences with seven and 11 amino acids, respectively, which were grafted into two cystine knot microproteins, the trypsin inhibitor EETI-II and the melanocortin receptor binding domain of the human agouti-related protein AGRP, as well as into the small disintegrin obtustatin.

Wu et al., "Stepwise in vitro affinity maturation of Vitaxin, an $\alpha_v\beta_3$-specific humanized mAb," *Proc. Nat. Acad. Sci. Vol.* 95, Issue 11, 6037-6042, May 26, 1998, discloses a focused mutagenesis implemented by codon-based mutagenesis applied to Vitaxin, a humanized version of the antiangiogenic antibody LM609 directed against a conformational epitope of the $\alpha_v\beta_3$ integrin complex. Wu et al., "Stepwise in vitro affinity maturation of Vitaxin, an v3-specific humanized mAb," *Proc. Nat. Acad. Sci., Vol.* 95, Issue 11, 6037-6042, May 26, 1998, discloses a focused mutagenesis implemented by codon-based mutagenesis applied to Vitaxin, a humanized version of the antiangiogenic antibody LM609 directed against a conformational epitope of the $\alpha_v\beta_3$ integrin complex.

BRIEF SUMMARY OF THE INVENTION

The following brief summary is not intended to include all features and aspects of the present invention, nor does it imply that the invention must include all features and aspects discussed in this summary.

In certain aspects, the present invention comprises an artificial integrin binding peptide, based on a combination of a knottin peptide and an engineered loop, where the engineered loop provides a binding sequence specific to bind to at least one of $\alpha_v\beta_5$ integrin, $\alpha_v\beta_3$ integrin and $\alpha_5\beta_1$ integrin, said binding sequence being comprised in a knottin protein scaffold. The knottin protein provides a "scaffold" due to its relatively rigid three-dimensional structure. The binding sequence will be an engineered integrin binding loop between 9 and 13 amino acids long, said loop comprising the sequence RGD. Said scaffold, except for the engineered integrin binding loop, is identical or at least substantially identical to one of: EETI-II, AgRP, mini-AGRP, agatoxin or miniagatoxin. It is shown here that certain scaffolds are tolerant to mutations in their loop regions.

In certain aspects, the present invention comprises an integrin binding peptide, comprising a binding sequence, which specifically binds to one or both of $\alpha_v\beta 5$ and $\alpha_v\beta 3$ integrins. Certain sequences also bind only to $\alpha_5\beta_1$ integrin. It has been shown that some of the present peptides will bind to only $\alpha_v\beta_5$ and $\alpha v\beta 3$ integrins and not $\alpha_5\beta_1$. The present engineered peptides further comprise a molecular scaffold which is a knottin protein. As described, the knottin proteins are characterized by intramolecular bonds which stabilize them and form a rigid scaffold. A portion of the scaffold, e.g., a loop beginning at residue 3 of EETI-II, is replaced by a sequence that has been discovered, though in vitro molecular evolution, to have superior binding properties. The peptide thus has a scaffold comprising replacement of a portion of the knottin with an integrin binding loop between 9 and 13 amino acids long, said peptide substantially identical to one of: EETI sequences as set forth in Table 2, AgRP sequences as set forth in Table 3 or mini-RGD-AgRP sequences as set forth in Table 4.

The present invention may further be characterized in that it comprises an integrin binding peptide comprising a molecular scaffold, wherein the molecular scaffold is covalently linked to either end of an RGD mimic sequence, which is a loop consisting of about 8-12 amino acids, which comprise the sequence RGD, and preferably are selected from the group consisting of XXXRGDXXXXX (sequence (a)), 11 amino acids and XXRGDXXXX (sequence (b)), 9 amino acids, where X is any amino acid and said mimic sequence is linked at either end in the vicinity of, preferably immediately adjacent to, cross-linked residues, e.g., cysteines. The molecular scaffold is preferably taken from a knottin peptide, and the mimic sequence is inserted in the scaffold between the two cysteine residues. The identity of the residues "X" can be varied in that, together, the X residues flanking the binding motif (RGD, RYD, etc.), provided a certain structure that will selectively recognize the ligand, in this case an endothelial integrin. Directed evolution techniques were used and peptides with surprising selectivity and binding affinity were obtained. It has been found that the number of residues on either side of the RGD sequence is critical, particularly in relation to the three dimensional structure of the flanking Cys residues. That is, the location of RGD as after 3 residues and before 5 residues (sequence (a)) is important with regard to the EETI scaffold, while the location in sequence (b) is similarly important in the AgRP or agatoxin scaffold. The present EETI peptides will have 2-5 disulfide linkages between cysteine residues, where the linkages are not directly between Cys residues immediately flanking the RGD loop, as shown in FIG. 3. In other knottins, there may be a disulfide linkage immediately flanking the loop, but in each case, there are at least two disulfide linkages, forming a molecular scaffold.

The present integrin binding peptides will have a specific affinity for an integrin selected from the group consisting of $\alpha_5\beta_1$, $\alpha_v\beta_3$ and $\alpha_v\beta_5$, particularly $\alpha_v\beta_3$. The present peptides preferably have a Kd less than 100 nM, or, more preferably less than 70 nM. Also they preferably do not bind to integrin $\alpha IIb\beta 3$, which is found on platelets. The term Kd means a dissociation constant, as is known in the art; lower Kd indicates tighter binding between the peptide and the integrin.

The molecular scaffold is preferably selected from the group consisting of EETI, AgRP, and agatoxin.

The sequences may be taken from a peptide having a sequence substantially identical to a peptide listed in Table 1 (EETI scaffold containing native fibronectin loop), Table 2 (EETI mutant, RGD in loop 4-6), Table 3 (AgRP peptides, RGD in loop) or Table 4 (mini-RGD-AgRP peptides, RGD in loop). Substantial identity may be regarded as least 70% identical, or at least 90-95% identical. Substantial identity may be different in the RGD loop and in the knottin scaffold.

The peptides of the present invention can be made by recombinant DNA production techniques, including a vector encoding a peptide sequence according to the present invention. The DNA sequences are chosen according to the genetic code, with codon preferences given according to the host cell, e.g., mammalian, insect, yeast, etc. The present peptides may also be made by peptide synthetic methods.

Thus there is provided a method of inhibiting binding of an integrin to vitronectin and, in some cases, fibronectin, comprising contacting said integrin with an integrin binding peptide comprising a molecular scaffold, wherein the molecular scaffold is covalently linked to either end of an RGD mimic sequence selected from the group consisting of XXXRGDXXXXX and XXRGDXXXX, where X is any amino acid. The present invention has been demonstrated with comparison to the $10^{th}$ domain of fibronectin ("10FN" in the figures, e.g., FIGS. 4(f) and 4(i)).

Also provided is a method of treating a proliferative disease comprising the step of administering to a subject in need thereof a composition comprising an integrin binding peptide comprising a molecular scaffold, wherein the molecular scaffold is covalently linked to either end of an RGD mimic sequence selected from the group consisting of XXXRGDXXXXX and XXRGDXXXX, where X is any amino acid. A wide variety of proliferative disorders will respond to the integrin inhibiting effects of the present peptides, which have been demonstrated with integrin $\alpha_v\beta_3$, $\alpha_v\beta_5$, and in some cases $\alpha_5\beta_1$. For example, adhesive interaction of vascular cells through this integrin is known to be necessary for angiogenesis, and an antibody to this integrin has been shown to block angiogenesis. The present peptides may also be used in vitro or in vivo, e.g., in bone or tissue grafts, to promote cell adhesion by binding to cells expressing a selected integrin. The present peptides may also be used as imaging agents, in recognition of their affinity for integrins, which are more highly expressed in certain types of cells. For example, tumor cells express higher levels of these integrins.

Also provided is a method for imaging tumors, in which engineered integrin binding peptides specific for certain integrins are administered to a living organism, and the binding of the peptides to sites where endothelial integrins are highly expressed serves to image tumors. The peptides disclosed here may be conjugated to a dye or radiolabel for such imaging.

BRIEF DESCRIPTION OF THE DRAWINGS

FIG. 2 (right panel) shows a high avidity integrin-binding protein in which the integrin binding proteins described below are presented in a tetravalent manner through linkage to a GCN 4-zipper, which spontaneously self-assembles to form a tetramer. Tetravalent presentation of the integrin antagonists will enhance integrin binding by increasing the local concentration of antagonist, upon binding of the first antagonist.

FIGS. 3A, 3B and 3C show the positions of the Cys-Cys disulfide linkages in the sequences of knottin proteins EETI-II (SEQ ID NO: 13), AgRP (SEQ ID NO: 107) and omega agatoxin 4B (SEQ ID NO: 16). Cysteine residues can be seen to be immediately flanking the RGD mimic loops, which, in the present engineered peptides, are between the brackets. For example, in AgRP, it can be seen that the cysteines flanking the RGD mimic sequence will be linked to each other, whereas in EETI they are not. The size of the grafted sequence will depend on the molecular framework structure, such that shorter loops will be preferred in cases where they are in the framework adjacent linked cysteines. Other loops between Cys residues may be engineered according to the present methods. Disulfide linkages for other knottin proteins are set forth in the knottin database. FIG. 3A-C is adapted from Biochemistry, 40, 15520-15527 (2001) and *J. Biol. Chem.*, 2003, 278:6314-6322.

FIG. 7 shows that the best mutants appear to be 1.5B, 2.5A, and 2.5D. This data suggests $K_d$ values of about 50 nM. When displayed on the yeast cell surface, these mutants bind to $\alpha_v\beta_3$ integrin about 2-3× better than the starting mutant RGD-EETI#3 (FN-RGD), although this is a gross estimate since we did not have enough soluble $\alpha_v\beta_3$ integrin to perform full titration curves.

FIG. 8A is a series of 4 pictures showing in vivo imaging of Cy5.5-labeled polypeptides in mice. 1.5 nmol of Cy5.5-labeled EETI-RGD peptide 2.5D or other indicated peptide was injected by tail vein into U87MG glioblastoma xenograft mouse models and imaged at various time points post injection. Arrows indicate the position of tumors. FIG. 8B is a graph showing quantified tumor/normal tissue ratio for Cy5.5-labeled 2.5D (top line, triangles) compared to Cy5.5-labeled FN-RGD (middle line, squares) and Cy5.5-labeled c(RGDyK) (SEQ ID NO: 140) (middle line, circles). The tumor/background ratio shows ~60% greater contrast for the high affinity evolved 2.5D peptide over the weaker binding FN-RGD and c(RGDyK) (SEQ ID NO: 140)peptides. Cy5.5-labeled FN-RDG negative control (bottom line, open squares) indicates background levels.

FIG. 11 is a series of histograms showing residue distribution of mutants isolated from EETI XXXRGDXXXXX library #2. The distribution of residues in different positions is shown for each position.

DETAILED DESCRIPTION OF THE PREFERRED EMBODIMENT

Overview

Figure 1A:
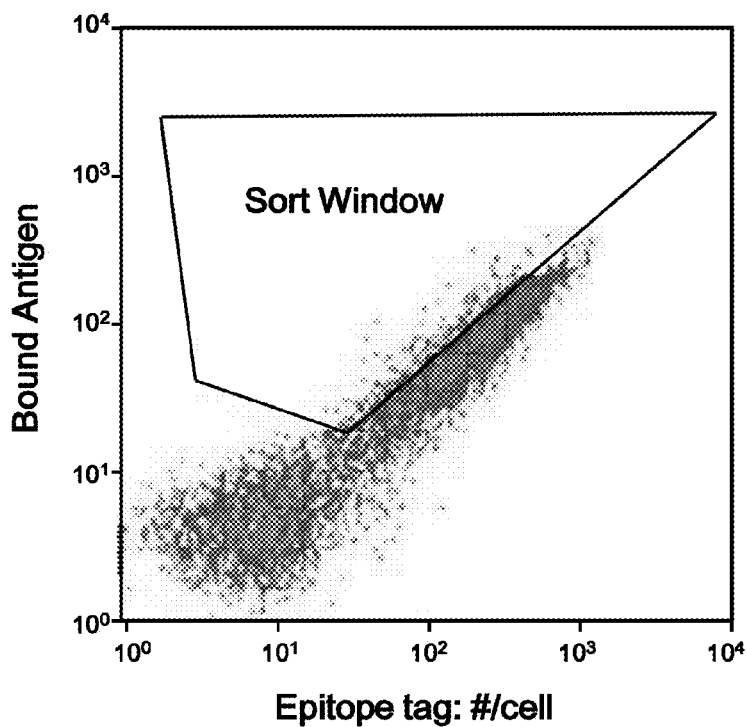
FIG. 1A shows an example of flow cytometry data depicted as a dot plot of individual cells. Yeast cells are double-labeled with a labeled antibody against the c-myc epitope tag (x-axis), and ligand labeled with another dye (y-axis). Since protein expression levels on the yeast cell surface are variable, a 'diagonal' cell population results, in which cells that express more protein bind more ligand; flow cytometry data is depicted as a dot plot of individual cells.
Figure 1B:
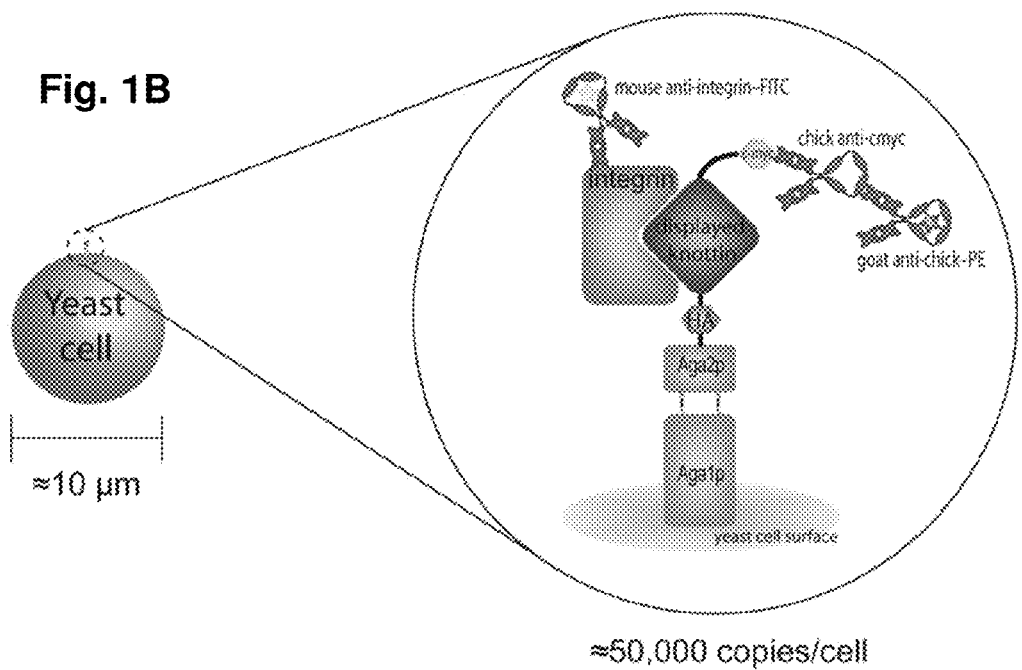
FIG. 1B shows a schematic of the present yeast display system; yeast fusion proteins are expressed on the cell surface (Boder and Wittrup, 1997). The yeast display construct shown in FIG. 1A has the general orientation: Aga2-HA-engineered knottin—c-myc epitope, with the c-myc epitope at the carboxy terminus of the peptide. The displayed knottin is labeled with a chicken anti-cmyc antibody, which is then detected with an Alexa 555-labeled anti-chicken secondary antibody. The displayed knottin is allowed to bind to a test integrin. Bound integrin is detected with an anti-integrin antibody, labeled with FITC.

The present invention involves the selection of a knottin protein as a peptide framework (scaffold) and replacing a portion of the sequence that appears on the surface with a specific binding sequence, e.g., containing an integrin binding sequence (RGD). The resulting engineered peptides have high affinity and specificity for selected integrins present on surfaces of tumor cells, epithelial cells, and the like.

Directed evolution is a useful technology for creating novel biomolecules that enhance or mimic protein function. Small polypeptides with applications as therapeutics and research tools were developed using directed evolution. These peptides are amenable to chemical synthesis and offer facile incorporation into biomaterials. Using molecular cloning, biologically active amino acid sequences derived from cell adhesion proteins (fibronectin) were grafted into several stable, constrained knottin peptide frameworks (EETI, AgRP and Agatoxin IVB) and were shown to bind to integrin receptors ($\alpha_v\beta_3$) with modest affinity. Since polypeptide conformation is critical for high affinity receptor binding and specificity, prototype molecules were subjected to affinity maturation using molecular evolution. Combinatorial libraries of mutants displayed on the yeast cell surface were screened by flow cytometric sorting to isolate polypeptides with enhanced integrin binding affinity. These proteins specifically modulate integrin-mediated cell adhesion and can serve as molecular imaging agents. These results demonstrate that naturally occurring constrained peptide scaffolds 1) can be redirected to function as adhesion molecule mimics and 2) can be engineered for enhanced integrin binding affinity through directed evolution.

The present methods have led to the development of specific binding peptides against the $\alpha_v\beta_3$, $\alpha_v\beta_5$, and, in some cases, the $\alpha 5\beta_1$ integrin receptors, which have been implicated in cell adhesion and angiogenesis of vascular tissue in cancer. Integrin-specific binders comprised of the cyclic peptide Arg-Gly-Asp (RGD, discussed in Background) have shown much therapeutic promise, but can benefit from improvements in affinity and stability. A novel selection approach based on yeast surface display was utilized for affinity maturation and stabilization of molecular scaffolds containing the RGD motif. In addition, frameworks for multivalent RGD ligand presentation through chemical crosslinking and protein engineering are presented.

Knottin proteins containing RGD motifs were assayed for binding against integrins. It was found that the scaffolds offer an extremely stable platform for conformationally constrained ligand presentation and are a useful framework for protein engineering studies. In addition, multivalent protein scaffolds can be engineered by replacing multiple binding faces of knottin proteins with RGD motifs for enhanced integrin binding.

Multivalent presentation of integrin-specific motifs through chemical crosslinking is also contemplated here. Receptor clustering has been shown to be important for high avidity integrin binding and function. A series of crosslinking agents can be developed for multivalent integrin ligand presentation using novel coupling methodology. Synergistic effects have been shown to exist between RGD and other integrin-specific peptide motifs. Therefore, cross linkers could also be designed that incorporate heterofunctional groups to couple different integrin-specific molecules. These multivalent integrin binding proteins and peptides can be tested for their ability to enhance integrin binding and antagonism of cell adhesion.

Combinatorial mutant libraries of RGD-based knottin scaffolds expressed on yeast were screened for specific, high affinity binding against soluble $\alpha_v\beta_3$ integrin using flow cytometry.

Definitions

The term "molecular scaffold" means a polymer having a predefined three-dimensional structure, into which can be incorporated a binding loop, which will contain an RGD mimic as described herein. The term "molecular scaffold" has an art-recognized meaning (in other contexts), which is also intended here. For example, a review by Skerra, "Engineered protein scaffolds for molecular recognition," *J. Mol. Recognit.* 2000; 13:167-187 describes the following scaffolds: single domains of antibodies of the immunoglobulin superfamily, protease inhibitors, helix-bundle proteins, disulfide-knotted peptides and lipocalins. Guidance is given for the selection of an appropriate molecular scaffold.

Incorporation of integrin binding motifs into a molecular (e.g., protein) scaffold offers a framework for ligand presentation that is more rigid and stable than linear or cyclic peptide loops. In addition, the conformational flexibility of small peptides in solution is high, and results in large entropic penalties upon binding. Incorporation of an RGD motif into a protein scaffold provides conformational constraints that are required for high affinity integrin binding, (as evidenced by the CDCRGDCFC (SEQ ID NO: 12) peptide described above (Koivunen et al., 1995)). Furthermore, the scaffold provides a platform to carry out protein engineering studies such as affinity or stability maturation.

Characteristics of a desirable scaffold for protein design and engineering include 1) high stability in vitro and in vivo, 2) the ability to replace amino acid regions of the scaffold with other sequences without disrupting the overall fold, 3) the ability to create multifunctional or bispecific targeting by engineering separate regions of the molecule, and 4) a small size to allow for chemical synthesis and incorporation of non-natural amino acids if desired. Scaffolds derived from human proteins are favored for therapeutic applications to reduce toxicity or immunogenicity concerns, but are not always a strict requirement. Other scaffolds that have been used for protein design include fibronectin (Koide et al., 1998), lipocalin (Beste et al., 1999), cytotoxic T lymphocyte-associated antigen 4 (CTLA-4) (Hufton et al., 2000), and tendamistat (McConnell and Hoess, 1995; Li et al., 2003). While these scaffolds have proved to be useful frameworks for protein engineering, molecular scaffolds such as knottins have a distinct advantage: their small size.

The term "proliferative diseases" refers to diseases in which some tissue in a patient proliferates at a greater than normal rate. Proliferative diseases may be cancerous or non-cancerous. Non-cancerous proliferative diseases include epidermic and dermoid cysts, lipomas, adenomas, capillary and cutaneous hemangiomas, lymphangiomas, nevi lesions, teratomas, nephromas, myofibromatosis, osteoplastic tumors, other dysplastic masses and the like.

The types of proliferative diseases which may be treated or imaged with compounds and compositions of the present invention include epidermic and dermoid cysts, lipomas, adenomas, capillary and cutaneous hemangiomas, lymphangiomas, nevi lesions, teratomas, nephromas, myofibromatosis, osteoplastic tumors, other dysplastic masses and the like.

The types of cancers which may be treated or imaged with compounds and compositions of the present invention include: breast carcinoma, bladder carcinoma, brain cancer, colorectal carcinoma, esophageal carcinoma, gastric carcinoma, germ cell carcinoma e.g., testicular cancer, gynecologic carcinoma, hepatocellular carcinoma, small cell lung carcinoma, non-small cell lung carcinoma, lymphomas, Hodgkin's lymphoma, non-Hodgkin's lymphoma, malignant melanoma, multiple myeloma, neurologic carcinoma, ovarian carcinoma, pancreatic carcinoma, prostate carcinoma, renal cell carcinoma, Ewings sarcoma, osteosarcoma, soft tissue sarcoma, pediatric malignancies and the like.

The term "effective amount" means an amount of a compound of the present invention that is capable of modulating binding of an integrin to a cognate ligand.

The term "knottin protein" means a structural family of small proteins, typically 25-40 amino acids, that bind to a range of molecular targets like proteins, sugars and lipids. Their three-dimensional structure is essentially defined by a peculiar arrangement of three to five disulfide bonds. A characteristic knotted topology with one disulfide bridge crossing the macro-cycle limited by the two other intrachain disulfide bonds, which was found in several different microproteins with the same cysteine network, lent its name to this class of biomolecules. Although their secondary structure content is generally low, the knottins share a small triple-stranded antiparallel β-sheet, which is stabilized by the disulfide bond framework. Biochemically well-defined members of the knottin family, also called cysteine knot proteins, include the trypsin inhibitor EETI-II from *Ecballium elaterium* seeds, the neuronal N-type $Ca^{2+}$ channel blocker ω-conotoxin from the venom of the predatory cone snail *Conus geographus*, agouti-related protein (See Millhauser et al., "Loops and Links: Structural Insights into the Remarkable Function of the Agouti-Related Protein," *Ann. N.Y. Acad. Sci.*, Jun. 1, 2003; 994(1): 27-35), the omega agatoxin family, etc.

Knottin proteins are shown in FIG. 3 as having a characteristic disulfide linking structure. This structure is also illustrated in Gelly et al., "The KNOTTIN website and database: a new information system dedicated to the knottin scaffold," *Nucleic Acids Research*, 2004, Vol. 32, Database issue D156-D159. A triple-stranded β-sheet is present in many knottins. The cysteines involved in the knot are shown as connected by lines in FIG. 3 indicating which Cys residues are linked to each other. The spacing between Cys residues is important in the present invention, as is the molecular topology and conformation of the RGD-containing integrin binding loop. These attributes are critical for high affinity integrin binding. The RGD mimic loop is inserted between knottin Cys residues, but the length of the loop must be adjusted for optimal integrin binding depending on the three-dimensional spacing between those Cys residues. For example, if the flanking Cys residues are linked to each other, the optimal loop may be shorter than if the flanking Cys residues are linked to Cys residues separated in primary sequence. Otherwise, particular amino acid substitutions can be introduced that constrain a longer RGD-containing loop into an optimal conformation for high affinity integrin binding.

The term "amino acid" includes both naturally occurring and synthetic amino acids and includes both the D and L form of the acids as well as the racemic form. More specifically, amino acids contain up to ten carbon atoms. They may contain an additional carboxyl group, and heteroatoms such as nitrogen and sulfur. Preferably the amino acids are α and β-amino acids. The term α-amino acid refers to amino acids in which the amino group is attached to the carbon directly attached to the carboxyl group, which is the α-carbon. The term β-amino acid refers to amino acids in which the amino group is attached to a carbon one removed from the carboxyl group, which is the β-carbon. The amino acids described here are referred to in standard IUPAC single letter nomenclature, with "X" meaning any amino acid.

The term "EETI" means Protein Data Bank Entry (PDB) 2ETI. Its entry in the Knottin database is EETI-II. It has the sequence (SEQ ID NO: 13)
GC PRILMR [CKQDSDC]LAGCV[CGPNGFC]G The bold and underlined portion is replaced above and in the examples below by the present RGD mimic sequence(s). Loops 2 and 3, including the end defining cysteines, are show in brackets. These loops can also be varied without affecting binding efficiency, as is demonstrated below.

The term "AgRP" means PDB entry 1HYK. Its entry in the Knottin database is SwissProt AGRP_HUMAN, where the full-length sequence of 129 amino acids may be found. It comprises the sequence beginning at amino acid 87. An additional G is added to this construct. It also includes a C105A mutation described in Jackson, et al. 2002 *Biochemistry*, 41, 7565.

(SEQ ID NO: 14)
GCVRLHESCLGQQVPCCDPCATCYCRFFNAFCYCR-KLGTAMNPCSRT

The dashed portion shows a fragment omitted in the "mini" version, below. The bold and underlined portion, from loop 4, is replaced by the RGD sequences described below.

The term "mini" in reference to AgRP means PDB entry 1MRO. It is also SwissProt AGRP_HUMAN. It has the sequence, similar to that given above, (SEQ ID NO: 15)
GCVRLHESCLGQQVPCCDP*A*ATCYCRFFNAFCYCR where the italicized "A" represents an amino acid substitution which eliminates a possible dimer forming cystine. (Cystine herein refers to the single amino acid; cysteine to the dimer.). The bold and underlined portion, from loop 4, is replaced by the below described he RGD sequences.

The term "agatoxin" means omega agatoxin PDB 1OMB and the SwissProt entry in the knottin database TOG4B_AGEAP. It has the sequence (SEQ ID NO: 16)
EDN--CIAEDYGKCTWGGTKCCRGRPCRCSMIGTNCECT-
PRLIMEGLSFA The dashes indicate portions of the peptide omitted for the "mini" agatoxin. As shown in Table 3, an additional glycine is added to the N-terminus of the mini-construct. The bold and underlined portion is replaced by the below described he RGD sequences.

The term "substantial identity" in the context of a peptide indicates that a peptide comprises a sequence with at least 70% sequence identity to a reference sequence, preferably 80%, more preferably 85%, most preferably at least 90% or at least 95% sequence identity to the reference sequence over a specified comparison window, which in this case is either the entire peptide, a molecular scaffold portion, or a binding loop portion (~9-11 residues). Preferably, optimal alignment is conducted using the homology alignment algorithm of Needleman and Wunsch (1970) *J. Mol. Biol.*, 48:443 453. An indication that two peptide sequences are substantially identical is that one peptide is immunologically reactive with antibodies raised against the second peptide. Another indication for present purposes, that a sequence is substantially identical to a specific sequence explicitly exemplified is that the sequence in question will have an integrin binding affinity at least as high as the reference sequence. Thus, a peptide is substantially identical to a second peptide, for example, where the two peptides differ only by a conservative substitution. "Conservative substitutions" are well known, and exemplified, e.g., by the PAM 250 scoring matrix. Peptides that are "substantially similar" share sequences as noted above except that residue positions that are not identical may differ by conservative amino acid changes. As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the NIH Multiple alignment workshop (http://helixweb.nih.gov/multi-align/). Three-dimensional tools may also be used for sequence comparison.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "endothelial integrin" is used in its conventional sense and means integrins expressed on the outer apical pole of the surface epithelium, and are involved in angiogenesis. More specific details are found at *J. Clin. Invest.*, 110:913-914 (2002).

The term "optical label" is used in its conventional sense to mean, e.g., Cy-5.5 and other dyes useful as near infrared imaging agents. A variety of optical labels can be used in the practice of the invention and include, for example, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumarin 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; La Jolta Blue; phthalo cyanine; and naphthalo cyanine. Other useful labels include the Alexa Fluor® dyes from Invitrogen, which are sulfonated dyes, based on aminocoumarin, rhodamine, etc.

The term "positron-emitting label" is used in its conventional sense and means a label for detection by a positron emission camera, as in positron emission tomography, in which the label is attached, e.g., via a chelator, to a peptide according to the present invention. The most common labels used positron emitting nuclei in PET are $^{11}$C, $^{13}$N, $^{15}$O and $^{18}$F. Positron emitters zirconium-89 ($^{89}$Zr) and iodine-124 ($^{124}$I) are also contemplated for their long half life. Other labels include in particular $^{94m}$Tc, $^{68}$Ga and $^{18}$F, $^{64}$Cu, $^{86}$Y, and $^{76}$Br.

The term "engineered integrin binding loop" means a primary sequence of about 9-13 amino acids which have been created ab initio through experimental methods such as directed molecular evolution to bind to endothelial integrins. That is, the sequence contains an RGD sequence or the like, placed between amino acids which are particular to the scaffold and the binding specificity desired. The RGD (RYD, etc) binding sequence is not simply taken from a natural binding sequence of a known protein.

EXPERIMENTAL

Library Creation

In order to generate a randomized library of RGD mimic sequences, oligonucleotides were prepared which coded for various RGD mimic sequences as they were to be contained within a selected knottin scaffold. Since the knottin/RGD engineered sequence was relatively short, the DNA used to express the engineered protein in yeast could be prepared synthetically. The DNA sequences to be ligated into the yeast display vector were obtained from MWG-BIOTECH Inc., High Point, N.C. Where an amino acid was to be varied, twenty different codons, each coding for a different amino acid, were synthesized for a given position. Randomized oligonucleotide synthesis has been used to create a coding cassette in which about 5 to about 15 amino acids are randomized (see, e.g., Burritt et al., (1996) *Anal. Biochem.* 238:1 13; Lowman (1997) *Annu. Rev. Biophys. Biomol. Struct.* 26:410 24; Wilson (1998) *Can. J. Microbiol.* 44:313 329).

The yeast display vector used for evolution of improved mutants is called "pCT". The vector is further described in US 2004/0146976 to Wittrup, et al., published Jul. 29, 2004, entitled "Yeast cell surface display of proteins and uses thereof." As described there, the vector provides a genetic fusion of the N terminus of a polypeptide of interest to the C-terminus of the yeast Aga2p cell wall protein. The outer wall of each yeast cell can display approximately $10^4$-$10^5$ protein agglutinins. The vector contains the specific restriction sites and illustrates the transcriptional regulation by galactose, the N-terminal HA and C-terminal c-myc epitope tags and the Factor Xa protease cleavage site.

The vector used in the present work contained NheI (GCTAGC) (SEQ ID NO: 17) and BamHI (GGATCC) (SEQ ID NO: 18) restriction sites for specific insertion of the RGD mimic coding sequence.

Labeling Yeast-Displayed Polypeptides

Below is a typical protocol to label a yeast library samples for sorting by flow cytometry (FACS):

1. Want $2 \times 10^6$ cells, $OD_{600}$ of 1.0≈$10^7$ cells/mL
2. Add 1 mL PBS/BSA (phosphate buffered saline containing 1 mg/mL bovine serum albumin) to wash cells
3. Spin down cells 3 min at 8000 RPM
4. Remove supernatant using vacuum
5. Re-suspend in 40 µL PBS/BSA containing proper amount of integrin (100 nM [2.5 µL of stock $\alpha_v\beta_3$]; no anti-cmyc at this point)
6. Incubate for 1.5 h at r.t (w/tumbling)
7. Add 1:250 dilution of (chick anti-cmyc) to labeling solution
8. DO NOT wash cells at this point.
9. Incubate 1 h at 4° C. (w/tumbling)
10. Keep on ice after this step.
11. Spin down cells 3 min at 8000 RPM, 4° C. and vacuum supernatant
12. Repeat wash steps 2-4
13. Re-suspend in 40 µL PBS/BSA containing proper amount of secondary labels (secondary labeling is simultaneous)
    i. Anti-integrin Ab (FITC conj): 1:25 dilution+Anti-chick (Alexa 555): 1:100 dilution
    ii. Positive control: Anti-chick (Alexa 555): 1:100 dilution (for FACS compensation)
    iii. Positive control: Anti-chick (Alexa 488): 1:100 dilution (for FACS compensation)
14. Incubate on ice 30 min and keep in dark (lid on ice bucket)
15. Spin down cells at 3 min at 8000 RPM, 4° C. and vacuum supernatant
16. Repeat steps 2-4: Add 1 mL PBS/BSA, pellet cells, vacuum supernatant
17. Leave pelleted cells on ice until use.

Fluorescent Cell Sorting

Commercially available flow cytometers can measure fluorescence emissions at the single-cell level at four or more wavelengths, at a rate of approximately 50,000 cells per second (Ashcroft and Lopez, 2000). Typical flow cytometry data are shown in FIG. 4-7, in which yeast have been labeled with two different color fluorescent probes to measure protein expression levels and bound soluble ligand (in this case integrin receptor). A 'diagonal' population of cells results due to variation in protein expression levels on a per cell basis: cells that express more protein will bind more ligand. The equilibrium binding constant ($K_d$) can be determined by titration of soluble ligand, and the dissociation rate constant ($k_{off}$) can be measured through competition binding of unlabeled ligand. With yeast, a monodispersity of tethered proteins exists over the cell surface, and soluble ligand are used for binding and testing, such that avidity effects are not observed, unlike other display methods using immobilized ligands. To date, the properties of most proteins expressed on the yeast cell surface mimic what is seen in solution in terms of stability and binding affinity (Bader et al., 2000; Feldhaus et al., 2003; Holler et al., 2000; VanAntwerp and Wittrup, 2000). See, also, Weaver-Feldhaus et al., "Directed evolution for the development of conformation-specific affinity reagents using yeast display," *Protein Engineering Design and Selection* Sep. 26, 2005 18(11):527-536.

Cell sorting was carried out on a FACSVantage (BD Biosciences) multiparameter laser flow cytometer and cell sorter. Before sorting, fluorescent staining was carried out as described above, so that analysis of integrin binding and c-myc expression levels were detected, as described above. Cells with the highest levels of integrin binding, normalized for c-myc expression levels, were gated and sorted into a collection tube containing culture media. Sorted clones were propagated in culture and flow cytometric screening was repeated several times to obtain an enriched population of yeast-displayed peptides with high affinity integrin binding.

After obtaining a pool of cells with high integrin binding affinity, single yeast clones were obtained by plating onto Petri dishes. Plasmid DNA was obtained from the entire yeast population, transformed to *E. coli* and then individual *E. coli* clones were selected for plasmid recovery and sequencing to determined the aa composition of individual mutants. The DNA sequences of representative peptides are given below.

Sequence Design: EETI-II Scaffold and Mini-AgRP Scaffold

The sequences listed below were generated from three different yeast displayed combinatorial libraries—two libraries based on the EETI-II scaffold and one library based on the Mini-AgRP scaffold. All libraries were sorted by fluorescence activated cell sorting (FACS). Mutants from each round were isolated and sequenced.

The EETI-II-based library was:

(SEQ ID NO: 19)
GCXXXRGDXXXXXCKQDSDCLAGCVCGPNGFCG, where X=any amino acid. This library produced mutants 1.x, listed below. A follow-up library was made in a similar manner in an attempt to improve the mutants made from the original library just mentioned. These resultant mutants are labeled 2.x, listed below.

In the above sequence EETI-II loops 2 and 3 (from left to right) are also underlined, but not bolded. Flanking cysteines are not underlined. As will be discussed below, these sequences have been shown to be tolerant to diversity without affecting the binding capacity of the binding loop.

The above-described library was also prepared with the insert XXRGDXXXX and these EETI-II peptides were mixed with the library shown here before sorting. However, no sequences from this library were isolated. This indicates the importance of having the proper number of flanking residues around the RGD sequence in this scaffold.

EETI-II Based Sequences:

TABLE 1

Sequences wherein the RGD motif (in italics) is found in the insert at positions 3-5.

| Peptide identifier | Sequence | SEQ ID NO: |
|---|---|---|
| RGD-EETI#2 | GCT*GRGDS*SPASSKCKQDSDCLA GCVCGPNGFCG | (SEQ ID NO: 20) |

TABLE 1-continued

Sequences wherein the RGD motif (in italics) is found in the insert at positions 3-5.

| Peptide identifier | Sequence | SEQ ID NO: |
|---|---|---|
| RGD-EETI#3 | GCVT*GRGDS***PASSCKQDSDCLA GCVCGPNGFCG | (SEQ ID NO: 21) |

RGD-EETI#3 had binding estimated to be in the range of $K_d$ 100-200 nM. RGD-EETI#2 had approximately half the affinity of RGD-EETI#3. The bolded sequences were chosen for initial loop design from native fibronectin RGD loop sequences.

Variants based on RGD-EETI#3 above were prepared, with the RGD motif at amino acid positions 6-8, where the sequence RGD is italicized in 1.4A. In other words, the starting library was GCXXXRGDXXXXXCKQDSD-CLAGCVCGPNGFCG (SEQ ID NO: 22)

The integrin-binding loop was inserted after the second residue and the first Cys.

TABLE 2

EETI sequences wherein the RGD motif (in italics in 1.4A) is found in the insert at positions 4-6.

| Peptide identifier | Sequence | SEQ ID NO: |
|---|---|---|
| 1.4A | GCAEP*RGD*MPWTWCKQDSDCLAGCVCGPNGFCG | (SEQ ID NO: 23) |
| 1.4B | GCVGGRGDWSPKWCKQDSDCPAGCVCGPNGFCG | (SEQ ID NO: 24) |
| 1.4C | GCAELRGDRSYPECKQDSDCLAGCVCGPNGFCG | (SEQ ID NO: 25) |
| 1.4E | GCRLPRGDVPRPHCKQDSDCQAGCVCGPNGFCG | (SEQ ID NO: 26) |
| 1.4H | GCYPLRGDNPYAACKQDSDCRAGCVCGPNGFCG | (SEQ ID NO: 27) |
| 1.5B | GCTIGRGDWAPSECKQDSDCLAGCVCGPNGFCG | (SEQ ID NO: 28) |
| 1.5F | GCHPPRGDNPPVTCKQDSDCLAGCVCGPNGFCG | (SEQ ID NO: 29) |
| 2.3A | GCPEPRGDNPPPSCKQDSDCRAGCVCGPNGFCG | (SEQ ID NO: 30) |
| 2.3B | GCLPPRGDNPPPSCKQDSDCQAGCVCGPNGFCG | (SEQ ID NO: 31) |
| 2.3C | GCHLGRGDWAPVGCKQDSDCPAGCVCGPNGFCG | (SEQ ID NO: 32) |
| 2.3D | GCNVGRGDWAPSECKQDSDCPAGCVCGPNGFCG | (SEQ ID NO: 33) |
| 2.3E | GCFPGRGDWAPSSCKQDSDCRAGCVCGPNGFCG | (SEQ ID NO: 34) |
| 2.3F | GCPLPRGDNPPTECKQDSDCQAGCVCGPNGFCG | (SEQ ID NO: 35) |
| 2.3G | GCSEARGDNPRLSCKQDSDCRAGCVCGPNGFCG | (SEQ ID NO: 36) |
| 2.3H | GCLLGRGDWAPEACKQDSDCRAGCVCGPNGFCG | (SEQ ID NO: 37) |
| 2.3I | GCHVGRGDWAPLKCKQDSDCQAGCVCGPNGFCG | (SEQ ID NO: 38) |
| 2.3J | GCVRGRGDWAPPSCKQDSDCPAGCVCGPNGFCG | (SEQ ID NO: 39) |
| 2.4A | GCLGGRGDWAPPACKQDSDCRAGCVCGPNGFCG | (SEQ ID NO: 40) |
| 2.4C | GCFVGRGDWAPLTCKQDSDCQAGCVCGPNGFCG | (SEQ ID NO: 41) |
| 2.4D | GCPVGRGDWSPASCKQDSDCRAGCVCGPNGFCG | (SEQ ID NO: 42) |

TABLE 2-continued

EETI sequences wherein the RGD motif (in italics in 1.4A) is found in the insert at positions 4-6.

| Peptide identifier | Sequence | SEQ ID NO: |
|---|---|---|
| 2.4E | GCPRPRGDNPPLTCKQDSDCLAGCVCGPNGFCG | (SEQ ID NO: 43) |
| 2.4F | GCYQGRGDWSPSSCKQDSDCPAGCVCGPNGFCG | (SEQ ID NO: 44) |
| 2.4G | GCAPGRGDWAPSECKQDSDCQAGCVCGPNGFCG | (SEQ ID NO: 45) |
| 2.4J | GCVQGRGDWSPPSCKQDSDCPAGCVCGPNGFCG | (SEQ ID NO: 46) |
| 2.5A | GCHVGRGDWAPEECKQDSDCQAGCVCGPNGFCG | (SEQ ID NO: 47) |
| 2.5C | GCDGGRGDWAPPACKQDSDCRAGCVCGPNGFCG | (SEQ ID NO: 48) |
| 2.5D | GCPQGRGDWAPTSCKQDSDCRAGCVCGPNGFCG | (SEQ ID NO: 49) |
| 2.5F | GCPRPRGDNPPLTCKQDSDCLAGCVCGPNGFCG | (SEQ ID NO: 50) |
| 2.5H | GCPQGRGDWAPEWCKQDSDCPAGCVCGPNGFCG | (SEQ ID NO: 51) |
| 2.5J | GCPRGRGDWSPPACKQDSDCQAGCVCGPNGFCG | (SEQ ID NO: 52) |

Thus there has been described an engineered integrin binding peptide comprising a scaffold sequence and an RGD insert, both of which may be modified as described.

The EETI-II scaffold as described above reveals a number of specific sequences, which form the EETI-II knottin scaffold as illustrated in FIG. 3, having three disulfide linkages. The native sequence, which is replaced by the insert is shown in brackets in FIG. 3 and in bold underline above; the insert is shown in bold underline in Tables 1 and 2. The scaffold sequence may be varied, as the primary function of the scaffold is to maintain the orientation of the RGD insert. The scaffold should have the GPNG (SEQ ID NO: 109) sequence, which is known to be needed for folding (Wentzel, et al., "Sequence Requirements of the GPNG (SEQ ID NO: 109) β-Turn of the *Ecballum elaterium* Trypsin Inhibitor Explored by Combinatorial Library Screening," *J. Biol. Chem.* 274(30):21037-21043 (1999)). Lysine 15 may be removed for ease of synthesis and labeling, and replaced with a less reactive residue. It can also be seen that the sequence CLAG (SEQ ID NO: 110) has been varied, e.g., CPAG (SEQ ID NO: 111), CQAG (SEQ ID NO: 112), CRAG (SEQ ID NO: 113). These mutations were isolated from the library; however, are thought to have arisen from primer errors, since mutagenesis was not performed at this amino acid position.

The RGD insert, on either side of the linked Cys residues, comprises the sequence RGD within an 11 amino acid sequence of 11 amino acids replaces the native sequence, with R at the 4$^{th}$ position. Putting R in the 3$^{rd}$ position (EETI #2) was found to decrease binding in the peptides tested. That is, the inserts, which had the sequence $X_1X_2X_3R_4G_5D_6X_7X_8X_9X_{10}X_{11}$ (sequence (a)) were superior to $X_1X_2R_3G_4D_5X_6X_7X_8X_9X_{10}X_{11}$ (sequence (b)), where the subscript indicates position in the insert). The length of the loop is based on the distance between the adjacent Cys residues, but may be varied between about 9 and 13 residues. As shown in FIG. 3, for EETI-II the adjacent Cys residues are not linked to each other; rather they are linked to other Cys residues in a peptide "scaffold," which is a knottin peptide such as listed above in Tables 1-4.

EETI Sequence Variations

The RGD-containing loop may be varied from the specific sequences disclosed. For example the loop sequence of 2.5F, PLPRGDNPPTE (SEQ ID NO: 106) (See below) may be varied in the 8 non-underlined residues to a certain degree without affecting binding specificity and potency. For example, if three of the eleven residues were varied, one would have about 70% identity to 2.5D. For guidance in selecting which residues to vary, histograms in FIG. 11 present information on likely residues for each position. For example, in position −3 (the first X, one would most likely use a proline residue, based on isolated mutants that had positive integrin binding. However, His or Leu are also possible choices, as shown by their higher incidence in mutants with good integrin binding properties.

The sequences from Table 2 were aligned using NPS@: Network Protein Sequence Analysis, TIBS 2000 March Vol. 25, No. 3 [291]:147-150, Combet C., Blanchet C., Geourjon C. and Deléage G. The alignment was performed at http://npsa-pbil.ibcp.fr/cgi-bin/align_multalin.pl, using default parameters. Residues conserved for 90% or more (uppercase letters): 24 is 72.73%. The sequences in Table 2 are considered substantially identical to the consensus sequence.

```
                                           (SEQ ID NO: 53)
GCPXGRGDWAPPSCKQDSDCRAGCVCGPNGFCG,
where X = any amino acid.
```

Agouti-Related Protein (AgRP) and Agatoxin Sequences:

The two wild-type proteins AgRP and Agatoxin are quite different in sequence, but they have the same three-dimensional fold. As a result, any RGD sequence that works in AgRP will work in Agatoxin, and vice versa.

The following sequences illustrate various RGD mimics, showing improvements in integrin binding properties obtained by the yeast display molecular evolution process described above. The integrin binding properties of the peptides were RGD-AgRP #1<#2, <#3:

TABLE 3

AgRP peptides

| ID no. | Sequence | SEQ ID NO: |
|---|---|---|
| RGD-AgRP#1 | GCVRLHESCLGQQVPCCDPCATCYCRGDCYCRKLGTAMNPCSRT | (SEQ ID NO 54) |
| RGD-AgRP#2 | GCVRLHESCLGQQVPCCDPCATCYCTGRGDSCYCRKLGTAMNPCSRT | (SEQ ID NO 55) |
| RGD-AgRP#3 | CVRLHESCLGQQVPCCDPCATCYCTGRGDSPASCYCRKLGTAMNPCSRT | (SEQ ID NO: 56) |
| Mini-RGD-AgRP | GCVRLHESCLGQQVPCCDPAATCYCTGRGDSPASCYCR | (SEQ ID NO: 57) |
| Mini-RGD-Agatoxin | GCIAEDYGKCTWGGTKCCRGRPCRCTGRGDSPASCECT | (SEQ ID NO: 58) |

A shortened version of AgRP was also prepared. The Mini-AgRP-based starting library was: GCVRLHESCLGQQVPCCDPAATCYC<u>XXRGDXXXX</u>CYCR (SEQ ID NO: 59)

Variants based on Mini-RGD-AgRP isolated by the techniques described above are shown below.

TABLE 4

Mini-RGD-AgRP peptides

| Number | Sequence | SEQ ID NO: |
|---|---|---|
| 3A | GCVRLHESCLGQQVPCCDPAATCYCVVRGDWRKRCYCR | (SEQ ID NO: 60) |
| 3B | GCVRLHESCLGQQVPCCDPAATCYCEERGDMLEKCYCR | (SEQ ID NO: 61) |
| 3C | GCVRLHESCLGQQVPCCDPAATCYCETRGDGKEKCYCR | (SEQ ID NO: 62) |
| 3D | GCVRLHESCLGQQVPCCDPAATCYCQWRGDGDVKCYCR | (SEQ ID NO: 63) |
| 3E | GCVRLHESCLGQQVPCCDPAATCYCSRRGDMRERCYCR | (SEQ ID NO: 64) |
| 3F | GCVRLHESCLGQQVPCCDPAATCYCQYRGDMKHCYCR | (SEQ ID NO: 65) |
| 3G | GCVRLHESCLGQQVPCCDPAATCYCTGRGDTKVLCYCR | (SEQ ID NO: 66) |
| 3H | GCVRLHESCLGQQVPCCDPAATCYCVERGDMKRRCYCR | (SEQ ID NO: 67) |
| 3I | GCVRLHESCLGQQVPCCDPAATCYCTGRGDVRMNCYCR | (SEQ ID NO: 68) |
| 3J | GCVRLHESCLGQQVPCCDPAATCYCVERGDMSKCYCR | (SEQ ID NO: 69) |
| 4A | GCVRLHESCLGQQVPCCDPAATCYCRGRGDMRRECYCR | (SEQ ID NO: 70) |
| 4B | GCVRLHESCLGQQVPCCDPAATCYCEGRGDVKVNCYCR | (SEQ ID NO: 71) |
| 4C | GCVRLHESCLGQQVPCCDPAATCYCVGRGDEKMSCYCR | (SEQ ID NO: 72) |
| 4D | GCVRLHESCLGQQVPCCDPAATCYCVSRGDMRKRCYCR | (SEQ ID NO: 73) |
| 4E | GCVRLHESCLGQQVPCCDPAATCYCERRGDSVKKCYCR | (SEQ ID NO: 74) |
| 4F | GCVRLHESCLGQQVPCCDPAATCYCEGRGDTRRRCYCR | (SEQ ID NO: 75) |
| 4G | GCVRLHESCLGQQVPCCDPAATCYCEGRGDVVRRCYCR | (SEQ ID NO: 76) |
| 4H | GCVRLHESCLGQQVPCCDPAATCYCKGRGDNKRKCYCR | (SEQ ID NO: 77) |
| 4I | GCVRLHESCLGQQVPCCDPAXTCYCKGRGDVRRVCYCR | (SEQ ID NO: 78) |
| 4J | GCVRLHESCLGQQVPCCDPAATCYCVGRGDNKVKCYCR | (SEQ ID NO: 79) |
| 5A | GCVRLHESCLGQQVPCCDPAATCYCVGRGDNRLKCYCR | (SEQ ID NO: 80) |
| 5B | GCVRLHESCLGQQVPCCDPAATCYCVERGDMKKCYCR | (SEQ ID NO: 81) |
| 5C | GCVRLHESCLGQQVPCCDPAATCYCEGRGDMRRRCYCR | (SEQ ID NO: 82) |
| 5D | GCVRLHESCLGQQVPCCDPAATCYCQGRGDGDVKCYCR | (SEQ ID NO: 83) |
| 5E | GCVRLHESCLGQQVPCCDPAATCYCSGRGDNDLVCYCR | (SEQ ID NO: 84) |
| 5F | GCVRLHESCLGQQVPCCDPAATCYCVERGDMIRCYCR | (SEQ ID NO: 85) |
| 5G | GCVRLHESCLGQQVPCCDPAATCYCSGRGDNDLVCYCR | (SEQ ID NO: 86) |
| 5H | GCVRLHESCLGQQVPCCDPAATCYCEGRGDMKMKCYCR | (SEQ ID NO: 87) |

TABLE 4-continued

Mini-RGD-AgRP peptides

| Number | Sequence | SEQ ID NO: |
|---|---|---|
| 5I | GCVRLHESCLGQQVPCCDPAATCYCIGRGDVRRRCYCR | (SEQ ID NO: 88) |
| 5J | GCVRLHESCLGQQVPCCDPAATCYCEERGDGRKKCYCR | (SEQ ID NO: 89) |
| 6B | GCVRLHESCLGQQVPCCDPAATCYCEGRGDRDMKCYCR | (SEQ ID NO: 90) |
| 6C | GCVRLHESCLGQQVPCCDPAATCYCTGRGDEKLRCYCR | (SEQ ID NO: 91) |
| 6E | GCVRLHESCLGQQVPCCDPAATCYCVERGDGNRRCYCR | (SEQ ID NO: 92) |
| 6F | GCVRLHESCLGQQVPCCDPAATCYCESRGDVVRKCYCR | (SEQ ID NO: 93) |
| 7C | GCVRLHESCLGQQVPCCDPAATCYC YGRGDNDLR CYCR | (SEQ ID NO: 94) |

Anti-Angiogenic Activity

The present peptides have been shown to bind to integrins $\alpha_v\beta_3$ and $\alpha_v\beta_5$, by in vitro experiments in which the peptides were incubated with soluble integrins as described above.

Based on present knowledge of cell adhesion and tumorigenesis, it may be expected that the present peptides will function in vivo as well as in vitro, and that they will exhibit anti-angiogenic and anti-proliferative activity. It is known that the integrin $\alpha_v\beta_3$ is required for angiogenesis, see Brooks et al., *Science* 264:569-571. In order to demonstrate and evaluate such activity, a number of assays, known in the art are included within the present concepts.

Such assays include, but are not limited to, assays of endothelial cell proliferation, endothelial cell migration, cell cycle analysis, and endothelial cell tube formation, detection of apoptosis, e.g., by apoptotic cell morphology or Annexin V-FITC assay, chorioallantoic membrane (CAM) assay, and inhibition of renal cancer tumor growth in nude mice. Examples of such assays are given in U.S. Pat. No. 6,962,974 to Kalluri, issued Nov. 8, 2005, entitled "Anti-angiogenic proteins and fragments and methods of use thereof." For example, C-PAE cells are grown to confluence in DMEM with 10% fetal calf serum (FCS) and kept contact inhibited for 48 hours. Control cells are 786-O (renal carcinoma) cells, PC-3 cells, HPEC cells, and A-498 (renal carcinoma) cells. Cells are harvested with typsinization (Life Technologies/Gibco BRL, Gaithersburg, Md., USA). A suspension of 12,500 cells in DMEM with 1% FCS is added to each well of a 24-well plate coated with 10 µg/ml fibronectin. The cells are incubated for 24 hours at 37° C. with 5% $CO_2$ and 95% humidity. Medium is removed and replaced with DMEM containing 0.5% FCS and 3 ng/ml bFGF (R&D Systems, Minneapolis, Minn., USA). Cells are treated with concentrations of the present engineered peptides ranging from 0.01 to 50 µg/ml. All wells receive 1µ Curie of $^3$H-thymidine at the time of treatment. After 24 hours, medium is removed and the wells are washed with PBS. Cells are extracted with 1N NaOH and added to a scintillation vial containing 4 ml of ScintiVerse II (Fisher Scientific, Pittsburgh, Pa., USA) solution. Thymidine incorporation is measured using a scintillation counter. The showing incorporation of $^3$H-thymidine into C-PAE cells treated with varying amounts of the peptides will show inhibition of cell division.

For animal testing, about two million 786-O cells are injected subcutaneously into 7- to 9-week-old male athymic nude mice. In the first group of mice, the tumors are allowed to grow to about 700 mm³. In a second group of mice, the tumors are allowed to group to 100 mm³. The engineered peptide (e.g., EETI-1.5B, 2.5A, and 2.5D), in sterile PBS is injected I.P. daily for 10 days, at a concentration of 20 mg/kg for the mice with tumors of 700 mm³, and 10 mg/kg for the mice with tumors of 100 mm3. Control mice receive either BSA or the PBS vehicle. The results will show a change in tumor volume from 700 mm³ for 10 mg/kg peptide treated, BSA-treated (+), and control mice. Tumors in the peptide-treated mice will shrink, while tumors in BSA-treated and control mice will grow.

In another known protocol (See again U.S. Pat. No. 6,962,974), about 5 million PC-3 cells (human prostate adenocarcinoma cells) are harvested and injected subcutaneously into 7- to 9-week-old male athymic nude mice. The tumors grow for 10 days, and are then measured with Vernier calipers. The tumor volume is calculated using the standard formula, and animals are divided into groups of 5-6 mice. Experimental groups are injected I.P. daily with a test engineered peptide (10 mg/kg/day) or a control drug (e.g., an anti-integrin antibody) (10 mg/kg/day). The control group receives PBS each day. The results will show that an engineered peptide inhibits the growth of tumors as well, or slightly better, than did the control drug. The experiment may be repeated at different dosages and times.

EETI, AgrP and AgatoxinPeptide Constructs

The peptides specifically set forth above may be modified in a number of ways. For example, the peptides may be further cross-linked internally, or may be cross linked to each other, or the RGD mimic loops may be grafted onto other cross linked molecular scaffolds. There are a number of commercially available crosslinking reagents for preparing protein or peptide bioconjugates. Many of these cross-linkers allow dimeric homo- or heteroconjugation of biological molecules through free amine or sulfhydryl groups in protein side chains. More recently, other crosslinking methods involving coupling through carbohydrate groups with hydrazide moieties have been developed. These reagents have offered convenient, facile, crosslinking strategies for researchers with little or no chemistry experience in preparing bioconjugates.

The present peptides may be produced by recombinant DNA or may be synthesized in solid phase using a peptide synthesizer, which has been done for the peptides of all three scaffolds described here. They may further be capped at their N-termini by reaction with fluorescein isothiocyanate (FITC) or other labels, and, still further, may be synthesized with amino acid residues selected for additional crosslinking reactions. TentaGel S RAM Fmoc resin (Advanced ChemTech) may be used to give a C-terminal amide upon cleavage. B-alanine is used as the N-terminal amino acid to prevent thiazolidone formation and release of fluorescein during peptide deprotection (Hermanson, 1996). Peptides are cleaved from the resin and side-chains are deprotected with 8% trifluoroacetic acid, 2% triisopropylsilane, 5% dithiothreitol, and the final product is recovered by ether precipitation. Peptides are purified by reverse phase HPLC using an acetonitrile gradient in 0.1% trifluoroacetic acid and a C4 or C18 column (Vydac) and verified using matrix-assisted laser desorption/ionization time-of-flight mass spectrometry (MALDI-TOF) or electrospray ionization-mass spectrosometry (ESI-MS).

When the present peptides are produced by recombinant DNA, expression vectors encoding the selected peptide are transformed into a suitable host. The host should be selected to ensure proper peptide folding and disulfide bond formation as described above. Certain peptides, such as EETI-II can fold properly when expressed in prokaryotic hosts such as bacteria.

Exemplary DNA sequences used for the present peptides are given below:

```
RGD-EETI#3-based hits (DNA sequences)
1.4B
                                          (SEQ ID NO: 95)
GGGTGCGTGGGGGGAGAGGGGATTGGAGCCCGAAGTGGTGCAAACAGGA

CTCCGACTGCCCGGCTGGCTGCGTTTGCGGGCCCAACGGTTTCTGCGGA 1.5B
                                          (SEQ ID NO: 96)
GGGTGCACGATCGGAGAGGGGATTGGGCCCCCTCGGAGTGCAAACAGGA

CTCCGACTGCCTGGCTGGCTGCGTTTGCGGGCCCAACGGTTTCTGCGGA 1.5F
                                          (SEQ ID NO: 97)
GGGTGCCACCCGCCGAGAGGGGATAACCCCCCCGTGACTTGCAAACAGGA

CTCCGACTGCCTGGCTGGCTGCGTTTGCGGGCCCAACGGTTTCTGCGGA 2.4F
                                          (SEQ ID NO: 98)
GGGTGCTATCAAGGAAGAGGGGATTGGTCTCCTTCATCGTGCAAACAGGA

CTCCGACTGCCCAGCTGGCTGCGTTTGCGGGCCCAACGGTTTCTGCGGA 2.5A
                                          (SEQ ID NO: 99)
GGGTGCCATGTAGGAAGAGGGGATTGGGCTCCTGAAGAGTGCAAACAGGA

CTCCGACTGCCAAGCTGGCTGCGTTTGCGGGCCCAACGGTTTCTGCGGA 2.5C
                                         (SEQ ID NO: 100)
GGGTGCGATGGAGGAAGAGGGGATTGGGCTCCTCCAGCGTGCAAACAGGA

CTCCGACTGCCGAGCTGGCTGCGTTTGCGGGCCCAACGGTTTCTGCGGA 2.5D
                                         (SEQ ID NO: 101)
GGGTGCCCTCAAGGAAGAGGGGATTGGGCTCCTACATCGTGCAAACAGGA

CTCCGACTGCCGAGCTGGCTGCGTTTGCGGGCCCAACGGTTTCTGCGGA 2.5F
                                         (SEQ ID NO: 102)
GGGTGCCCTCGACCAAGAGGGGATAACCCTCCTCTAACGTGCAAACAGGA

CTCCGACTGCCTAGCTGGCTGCGTTTGCGGGCCCAACGGTTTCTGCGGA 2.5H
                                         (SEQ ID NO: 103)
GGGTGCCCTCAAGGAAGAGGGGATTGGGCTCCTGAATGGTGCAAACAGGA

CTCCGACTGCCCAGCTGGCTGCGTTTGCGGGCCCAACGGTTTCTGCGGA 2.5J
                                         (SEQ ID NO: 104)
GGGTGCCCTCGAGGAAGAGGGGATTGGTCTCCTCCAGCGTGCAAACAGGA

CTCCGACTGCCAAGCTGGCTGCGTTTGCGGGCCCAACGGTTTCTGCGGA
```

Dimeric, trimeric, and tetrameric complexes of the present peptides can be formed through genetic engineering of the above sequences or by reaction of the synthetic cross-linkers with engineered peptides carrying an introduced cysteine residue, for example on the C-terminus of the peptide. These oligomeric peptide complexes can be purified by gel filtration. Oligomers of the present peptides can be prepared by preparing vectors encoding multiple peptide sequences end-to-end. Also, multimers may be prepared by complexing the peptides, such as, e.g., described in U.S. Pat. No. 6,265,539. There, an active HIV peptide is prepared in multimer form by altering the amino-terminal residue of the peptide so that it is peptide-bonded to a spacer peptide that contains an amino-terminal lysyl residue and one to about five amino acid residues such as glycyl residues to form a composite polypeptide. Alternatively, each peptide is synthesized to contain a cystine (Cys) residue at each of its amino- and carboxy-termini. The resulting di-cystine-terminated (di-Cys) peptide is then oxidized to polymerize the di-Cys peptide monomers into a polymer or cyclic peptide multimer. Multimers may also be prepared by solid phase peptide synthesis utilizing a lysine core matrix. The present peptides may also be prepared as nanoparticles. See, "Multivalent Effects of RGD Peptides Obtained by Nanoparticle Display," Montet, et al., *J. Med. Chem.;* 2006; 49(20) pp 6087-6093. EETI dimerization may be carried out with the present EETI-II peptides according to EETI-II dimerization paper that just came out: "Grafting of thrombopoietin-mimetic peptides into cystine knot miniproteins yields high-affinity thrombopoietin antagonist and agonists," Krause, et al., *FEBS Journal;* 2006; 274 pp 86-95.

One may also prepare chemically synthesized peptide-based crosslinking reagents for use in cross-linking the present peptides. The peptide may further contain a fluorescent label (fluorescein) and two or more thiol-reactive maleimide groups introduced at lysine residues spaced along a flexible backbone composed of glycine, serine, and glutamic acid (Cochran and Stern, 2000; Cochran et al., 2000). The non-repeating backbone amino acid sequences are designed to be water-soluble with little propensity to form an ordered structure, and to provide sufficient length and flexibility to allow integrin binding side chains to bind simultaneously to a cell surface. Maleimide-to-maleimide distances for the cross-linkers, in extended conformations for allowing pendant groups to present peptides in the same plane, are approximately 45 Angstroms for the dimeric cross-linkers, and 50 Angstroms for the trimeric, and tetrameric cross linkers, as estimated from molecular models.

Figure 2:
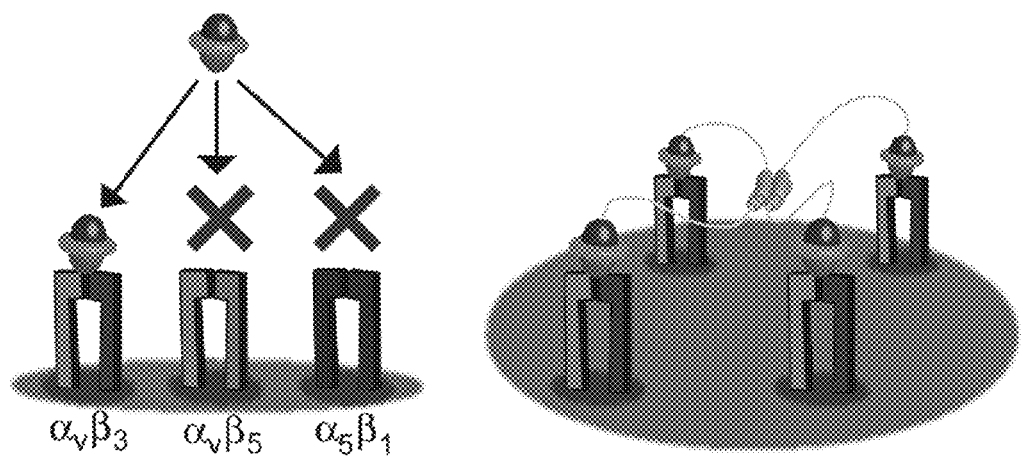
FIG. 2 (left panel) is a schematic representation of an integrin antagonist having high specificity for one integrin ($\alpha_v\beta_3$ here) engineered using yeast display and flow cytometry enrichment as referred to in FIG. 1. Integrin antagonists with ultra high specificity will allow for detection and inhibition of only certain integrins.
Figure 4A:
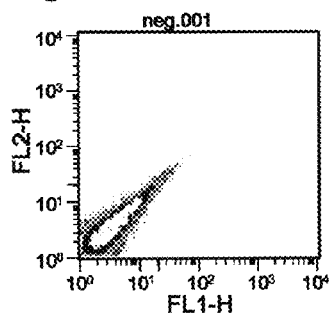
FIG. 4A-FIG. 4I is a series of nine panels, (a) through (i) from top left to bottom right, showing flow cytometry data obtained for yeast-displayed RGD-EETI#3 (also called FN-RGD). Panels (a) through (c) are controls; FL1-H represents the signal generated from the FITC-labeled integrin antibody, and FL2-H represents the signal generated from the chicken anti-cmyc antibody+Alexa-555 labeled anti-chicken secondary antibody. Panels (d) through (f) are histograms of the data presented below in panels (g) (h) and (i). Panels (g), (h) and (i) (Bottom row) are dot plots of RDG-EETI#3 induced at 30° C., with 100 nM integrin $\alpha_v\beta_3$ (e), at 20° C., with 100 nM integrin $\alpha_v\beta_3$ (f) and 10FN ($10^{th}$ domain of fibronectin) induced at 30° C., with 100 nM integrin $\alpha_v\beta_3$. The plots show that the RGD-EETI#3 (FN-RGD) peptide binds better than the $10^{th}$ domain of fibronectin, a natural $\alpha_v\beta_3$ integrin binder, and, further, that the peptide folds correctly at both 30° C. and 20° C. expression.
Figure 4B:
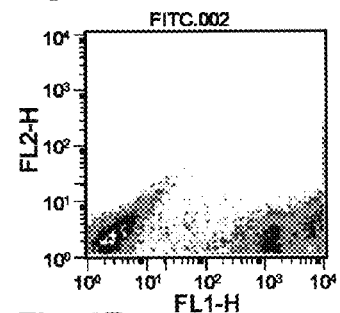
Figure 4C:
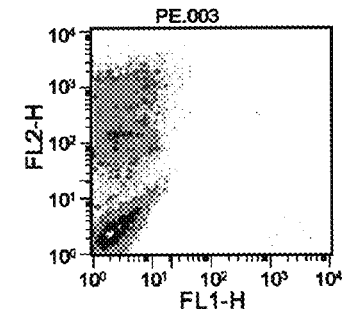
Figure 4D:
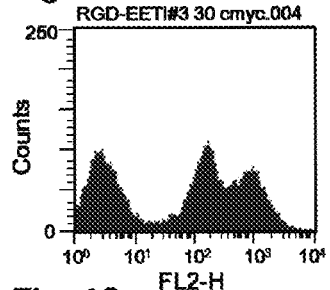
Figure 4E:
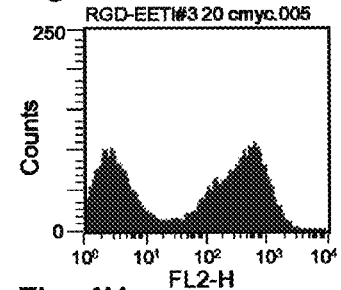
Figure 4F:
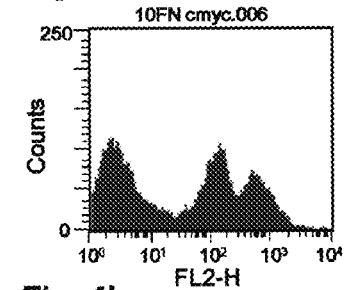
Figure 4G:
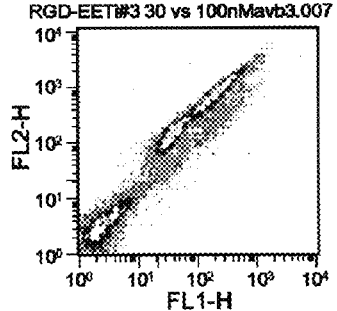
Figure 4H:
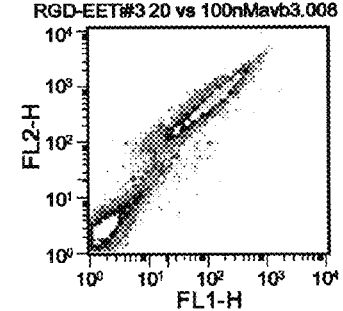
Figure 4I:
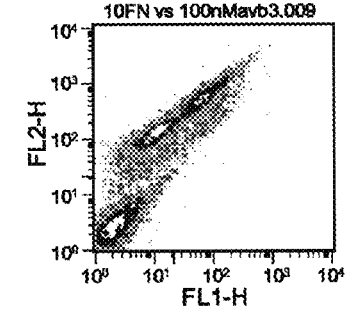
Figure 5A:
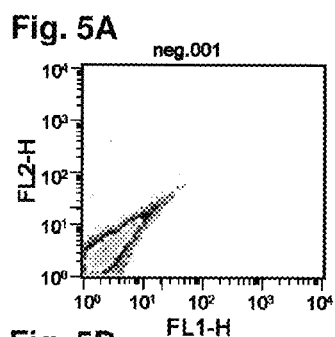
FIG. 5A through FIG. 5G is a series of seven panels, (a) through (g) from top left to bottom right, showing flow cytometry data obtained for yeast-displayed RGD-AgRP#3 (panel d), Agatoxin #2 (panel e), mini AgRP (panel f) and mini-RGD-Agatoxin (panel g). Panels (a) through (c) are controls; parameters are FL1-H and FL2-H are as in FIG. 4; Second row panels (d) and (e) are, respectively, dot plots of RGD-AgRP#3 with 100 nM integrin $\alpha_v\beta_3$ and RGD-agatoxin #2 with 100 nM integrin $\alpha_v\beta_3$. Third row panels (f) and (g) are, respectively, dot plots of mini-RGD-AgRP with 100 nM integrin $\alpha_v\beta_3$ and mini-RGD-agatoxin with 100 nM integrin $\alpha_v\beta_3$. The plots show that the "mini" versions of RGD-AgRP #3 and RGD-agatoxin#2 bind to integrin $\alpha_v\beta_3$ just as well as the full-length versions.
Figure 5B:
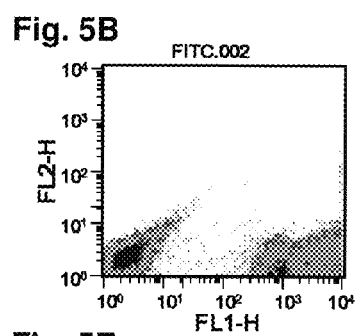
Figure 5C:
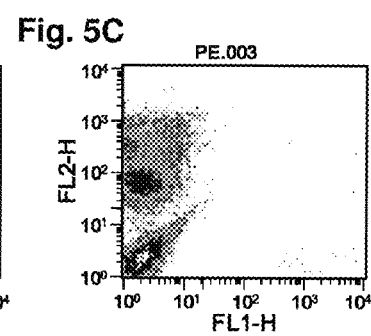
Figure 5D:
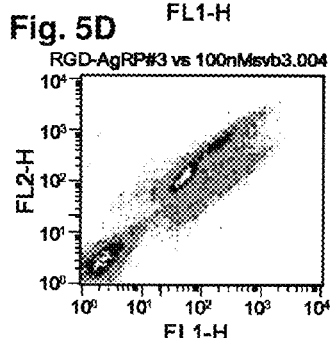
Figure 5E:
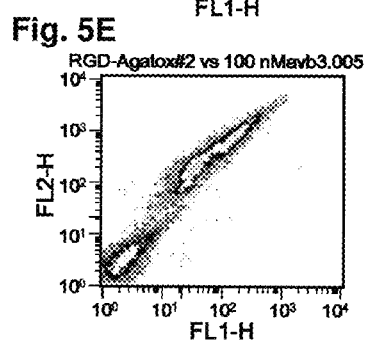
Figure 5F:
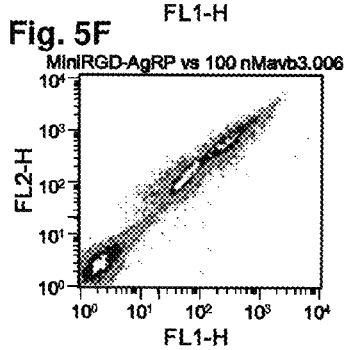
Figure 5G:
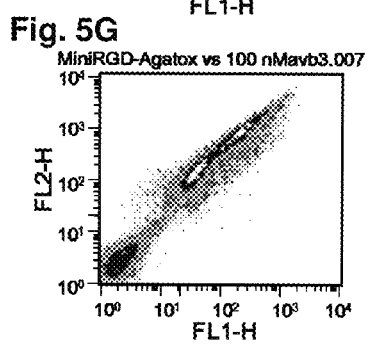
Figure 6A:
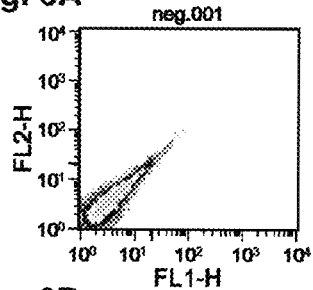
FIG. 6A through FIG. 6M is a series of 13 panels (a) through (m) showing dot plots of EETI-based RGD mutants obtained by directed evolution, labeled with 100 nM of $\alpha_v\beta_3$ integrin. The first row consists of controls. FL1H and FL2H are labeled as before. The samples are labeled from left to right for each row. Samples 1.5B (d), 1.4B (e), 1.5F (f), 2.4F (g), 2.5A (h), 2.5C (i), 2.5D (j), 2.5F (k), 2.5H (l) and 2.5J (m) represent EETI-based variants as set forth in Table 2.
Figure 6B:
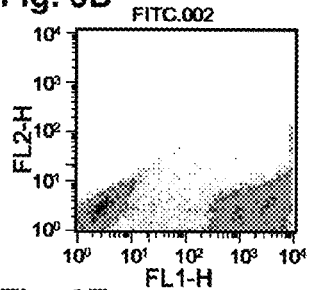
Figure 6C:
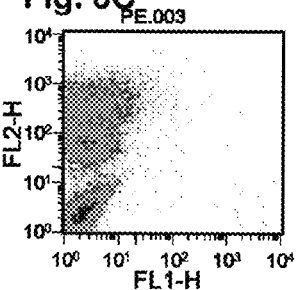
Figure 6D:
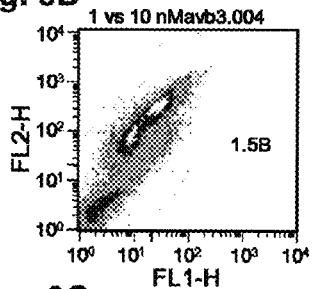
Figure 6E:
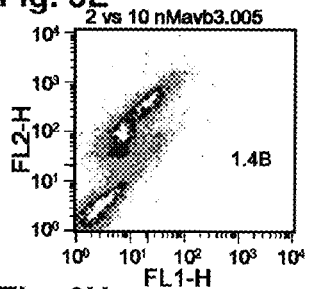
Figure 6F:
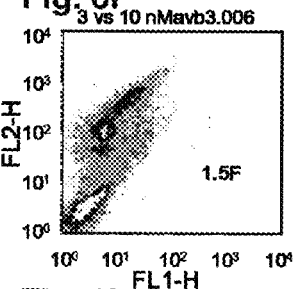
Figure 6G:
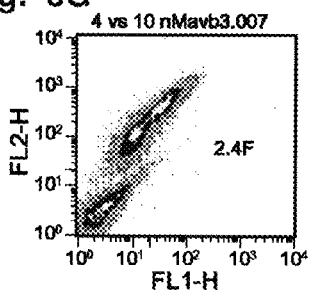
Figure 6H:
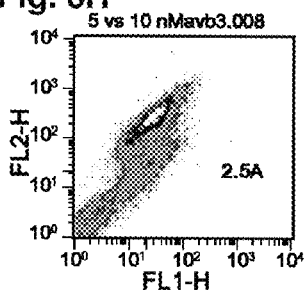
Figure 6I:
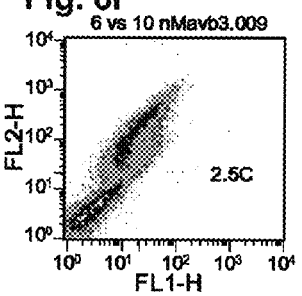
Figure 6J:
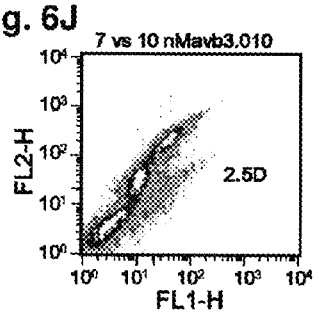
Figure 6K:
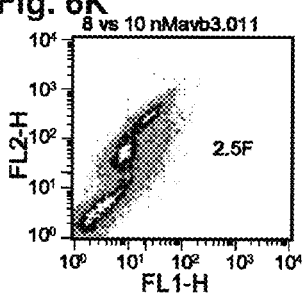
Figure 6L:
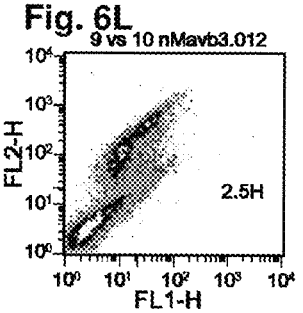
Figure 6M:
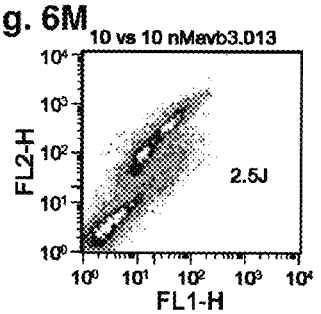
Figure 7A:
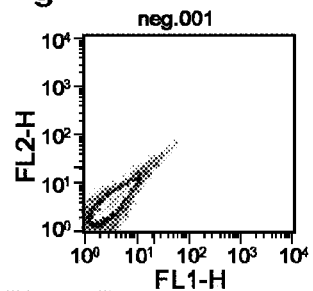
FIG. 7A through FIG. 7M is a series of 13 panels showing dot plots and histograms (panels (c), (f), (i), (k), and (m)) showing a control (a), and the samples as labeled in the center column of the figure, i.e., 1.5B, 2.4F, 2.5A, 2.5D and 2.5J. These peptides are labeled with 50 nM integrin $\alpha_v\beta_3$ and further defined in the table below. The flow cytometry parameters are as given above.
Figure 7B:
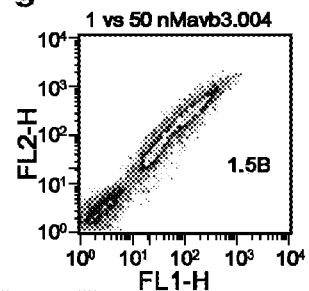
Figure 7C:
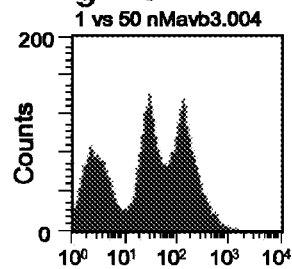
Figure 7D:
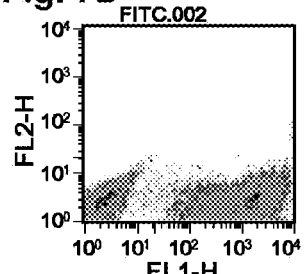
Figure 7E:
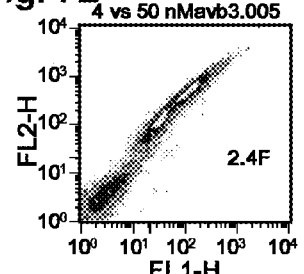
Figure 7F:
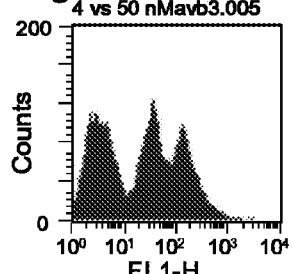
Figure 7G:
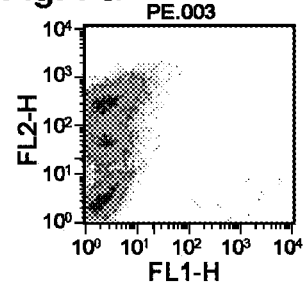
Figure 7H:
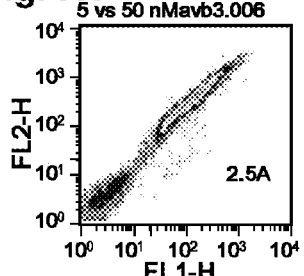
Figure 7I:
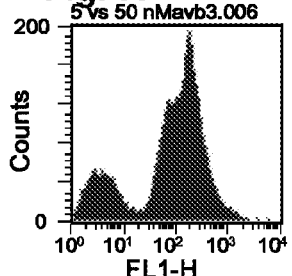
Figure 7K:
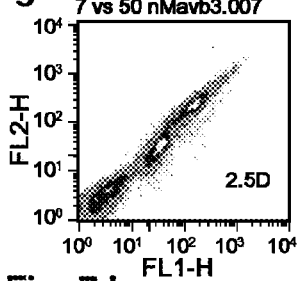
Figure 7L:
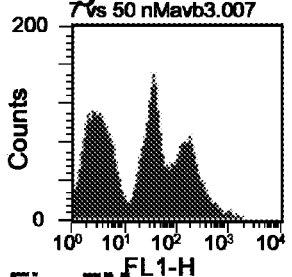
Figure 7J:
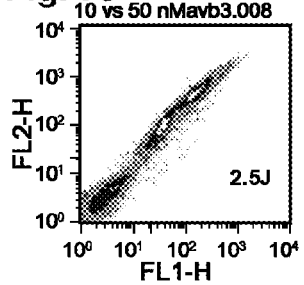
Figure 7M:
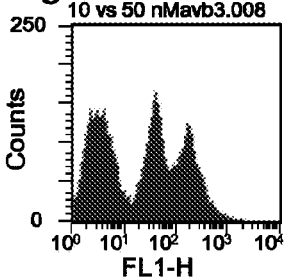

Other reagents would allow multivalent presentation of integrin binding peptides or small protein scaffolds. Ruthenium-based metathesis catalysts would allow site-specific crosslinking of alkene functional groups incorporated into amino acid side chains. The ability to specifically couple biomolecules using a chemical strategy that does not rely on natural amino acids would be extremely useful in creating small oligomeric peptide and protein motifs. An example is illustrated in FIG. 2. An amphipathic helix is derived from the coiled coil helix of the transcription factor GCN4, in which hydrophobic positions of heptad repeat have been exchanged to insert RGD mimics. Further details are given in Pack et al., "Tetravalent miniantibodies with high avidity assembling in *Escherichia coli.,*" *J Mol Biol.* 1995 Feb. 10; 246(1):28-34.

Synergistic sites on fibronectin and other adhesion proteins have been identified for enhanced integrin binding (Ruoslahti, 1996; Koivunen et al., 1994; Aota et al., 1994; Healy et al., 1995). The ability to incorporate different integrin-specific motifs into one soluble molecule would have an important impact on therapeutic development. Crosslinkers with heterofunctional specificity may be used for creating integrin-binding proteins with synergistic binding effects. In addition, these same crosslinkers could easily be used to create bispecific targeting molecules, or as vehicles for delivery of radionuclides or toxic agents for imaging and therapeutic applications.

Methods of Use

The present engineered peptides may be used in a variety of ways. If the peptides are attached to a surface, they may be used to attract/recruit cells to grow on the surface. For example, the present peptides may be applied to prosthetic devices, implants, bone grafts, and the like to promote tissue growth and healing at the site. They may be attached to culture dishes and promote attachment and differentiation of cells in culture. In addition, the present engineered peptides may be used to modulate cell binding to selected integrins such as $\alpha_5\beta_1$, $\alpha_v\beta_3$ and $\alpha_v\beta_5$, particularly $\alpha_v\beta_3$, by adding the peptides to a cell culture to prevent cells expressing these integrins from adhering to a substrate. In a series of experiments using the present RGD-containing peptides to block adhesion of U87MG glioblastoma cells to vitronectin-coated plates, it was found that the present peptides 2.5F, 2.5D, and 1.5D all blocked adhesion better than controls and comparative compounds FN-RGD and c(RGDyK) (SEQ ID NO: 140) (data not shown). Also, the present 2.5F, 2.5D and 1.5B peptides were tested for blocking adhesion of U87MG glioblastoma cells to fibronectin-coated plates. In this case, only echistatin and polypeptide 2.5F blocked adhesion of U87MG glioblastoma cells to the fibronectin-coated plates. This confirms that the RGD-miniprotein 2.5F binds with strong affinity to the $\alpha_5\beta_1$ integrin subtype.

These binding studies show that the present peptides can be used in soluble form to modulate binding of cells to known cell culture substrates (extracellular matrix). Cell binding to integrins can be used to modulate stem cell self-renewal or differentiation. For example, it is known that stem cells express higher levels of the beta 1-integrin family of extracellular matrix receptors than transit amplifying cells and this can be used to isolate each subpopulation of keratinocyte and to determine its location within the epidermis. See, Watt, "Epidermal stem cells: markers, patterning and the control of stem cell fate," Philos Trans R Soc Lond B Biol Sci., 1998 Jun. 29; 353(1370): 831-837. Alternatively, the engineered peptides may be prepared and coated on plates or incorporated into polymers or other biomaterials and used as a cell culture substrate to promote adhesion by the selected integrin.

The present peptides may also be used to treat proliferative diseases, when administered in soluble form. By attaching to cellular integrins, they block attachment of the cells and inhibit their growth and development. The present peptides will therefore find use in cancer therapy. The instant peptides are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are also useful when coadminsitered with radiation therapy. The present peptides may also be chemically linked to cytotoxic agents. They may also be used with other angiogenesis inhibitors. "Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, interferon-.α., interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107. (1996); Jpn. J. Pharmacol., Vol. 75, p. 105 (1997); Cancer Res., Vol. 57, p. 1625 (1997); Cell, Vol. 93, p. 705 (1998); Intl. J. Mol., Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141 145 (1985)), and antibodies to VEGF (see; Nature Biotechnology, Vol. 17, pp. 963 968 (October 1999); Kim et al., Nature, 362, 841 844 (1993).

The present peptides may also be used in vitro as cell labeling reagents, and in vivo as imaging or diagnostic agents, binding to cells, such as tumor cells, which express high levels of a specific integrin.

Synthesis of Soluble Peptides

Folding Conditions for EETI-II Polypeptides

In preparing the present peptides, it is essential that the correct disulfide linkages be formed, and that the peptide be correctly folded. Glutathione-assisted oxidative folding of the cystine-knot was used. An exemplary protocol for EETI-II is given below. Large scale folding reactions were performed with 20% DMSO (v/v) in 0.1 M ammonium bicarbonate, pH 9 and 2.5 mM reduced glutathione while gently rocking overnight. The final oxidized product was purified by semi-preparative HPLC using various linear gradients of solvent A and solvent B. Following purification, the peptide was lyophilized and stored until used. Working concentrations of pure peptide dissolved in purified water were determined by amino acid analysis. The purified peptide was analyzed by HPLC and ESI-MS.

Solvent (A) is 99.9% water 0.1% TFA, (B) is 10% water 90% MeCN and 0.1% TFA.

Folding Conditions for Mini-AGRP Polypeptides

Tris pH 8.0

10 mM reduced glutathione 2 mM oxidized glutathione 0.5 M DMSO with or without 2-4M guanidine (depending on the peptide)

1-3 days at room temperature.

Data on Synthesized Agouti Peptides: The peptides were tested for activity; the results are as follows, with the peptide designation corresponding to the sequence given in Table 4: IC50's (obtained by competing off binding of $^{125}$I-echistatin as described above)

WT—1.4±0.7 µM

3F—880±340 nM

6E—130±20 nM

6F—410±80 nM

7C—23±4 nM

Imaging Probes

The present polypeptides target $\alpha_v\beta_3$, $\alpha_v\beta_5$, and in some cases $\alpha_5\beta_1$ integrin receptors. They do not bind to other integrins tested. Thus, these engineered integrin-binding polypeptides have broad diagnostic and therapeutic applications in a variety of human cancers that specifically overexpress the above named integrins. As described below, these polypeptides bind with high affinity to both detergent-solubilized and tumor cell surface integrin receptors. Furthermore, when used as optical imaging agents in mouse xenograft models, the tumor/background signal ratio generated by these engineered polypeptides is approximately 60% greater than that elicited by an alternative pentapeptide currently under pre-clinical development. Also, the present engineered high-affinity integrin-binding polypeptides can also be labeled with positron emitting isotopes and changed from optical imaging probes to robust positron emission tomography (PET)-based imaging agents. In a clinical setting, these polypeptides will be used to visualize integrin expression in the human body for diagnostic and management applications in cancer. They can be coupled to radionuclides for therapeutic purposes. They offer advantages of stability, which reduces toxic uptake of free radionuclides by the kidneys.

As described above, it is known that the integrin $\alpha_v\beta_3$ is expressed during angiogenesis. The $\alpha_v\beta_3$ (and $\alpha_v\beta_5$) integrins are also highly expressed on many tumor cells including osteosarcomas, neuroblastomas, carcinomas of the lung, breast, prostate, and bladder, glioblastomas, and invasive melanomas The $\alpha_v\beta_3$ integrin has been shown to be expressed on tumor cells and/or the vasculature of breast, ovarian, prostate, and colon carcinomas, but not on normal adult tissues or blood vessels. Therefore, noninvasive methods to visualize and quantify integrin expression in vivo are crucial for patient-specific treatment of cancer with integrin antagonists. Also, the $\alpha_5\beta_1$ has been shown to be expressed on tumor cells and/or the vasculature of breast, ovarian, prostate, and colon carcinomas, but not on normal adult tissue or blood vessels. The present, small, conformationally-constrained polypeptides (about 33 amino acids) are so constrained by intramolecular bonds, such as shown in FIG. 3. For example, EETI-II has three disulfide linkages. This will make it more stable in vivo. These peptides target $\alpha_v$ integrins alone, or both $\alpha_v$ and $\alpha_5\beta_1$ integrins. Until now, it is believed that the development of a single agent that can bind $\alpha_v\beta_3$, $\alpha_v\beta_5$, and $\alpha_5\beta_1$ integrins with high affinity and specificity has not been achieved. Since all three of these integrins are expressed on tumors and are involved in mediating angiogenesis and metastasis, a broad spectrum targeting agent (i.e., $\alpha_v\beta_3$, $\alpha_v\beta_5$, and $\alpha_5\beta_1$) will likely be more effective for diagnostic and therapeutic applications.

The present engineered polypeptides (termed RGD-miniproteins) have several advantages over previously identified integrin-targeting compounds. They possess a compact, disulfide-bonded core that confers proteolytic resistance and exceptional in vivo stability.

Figure 8C:
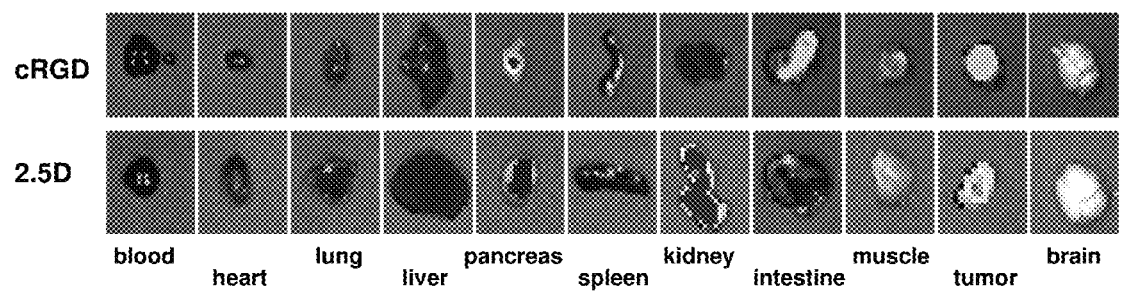
FIG. 8C is a series of images of different organs showing uptake of Cy5.5-labeled 2.5D and a comparison peptide, c(RGDyK) (SEQ ID NO: 140). It can be seen that the tumor took up significantly more 2.5D than c(RGDyK) (SEQ ID NO: 140), and that other organs were not significantly showing fluorescence, except for the kidney, where the peptide would accumulate prior to excretion.

Our studies indicate their half-life in mouse serum to be approximately 90 hours (data not shown). Their larger size (~3-4 kDa) and enhanced affinity compared to RGD-based cyclic peptides confer enhanced pharmacokinetics and biodistribution for molecular imaging and therapeutic applications. This is described in connection with FIG. 8. These RGD-miniproteins are small enough to allow for chemical synthesis and site-specific conjugation of imaging probes, radioisotopes, or chemotherapeutic agents. Furthermore, they can easily be chemically modified to further improve in vivo properties if necessary. The imaging study shown in FIG. 8 shows tumor localization by peptide 2.5D. The tumor is indicated by an arrow. The near infrared fluorescent Cy5.5 label study provides guidance for the preparation of these polypeptides as $^{18}$F and $^{64}$Cu-labeled PET imaging probes. In the clinical setting, these imaging agents will play a critical role in identifying patients whose cancer would benefit most from specific integrin-targeted therapy, and will provide a molecular rationale for why treatments may later fail if tumors cease to express these integrins. They may also serve to stage cancer when coupled with existing PET tracers such as 2-fluoro-2-deoxy-glucose (FDG). In addition, as described above, these RGD-miniproteins may be used for treatment of a variety of human cancers, as RGD-based targeting agents have been shown to have therapeutic efficacy through caspase-mediated apoptosis and cell death (see, Brooks, P. C., Montgomery, A M., Rosenfeld, M., Reisfeld, R A, Hu, T., Klier, G. & Cheresh, D. A. (1994). Integrin alpha v beta 3 antagonists promote tumor regression by inducing apoptosis of angiogenic blood vessels. *Cell* 79, 1157-64.; Chatterjee, S., Brite, K. H. & Matsumura, A (2001). Induction of apoptosis of integrin-expressing human prostate cancer cells by cyclic Arg-Gly-Asp peptides. *Clin Cancer Res* 7, 3006-11.

Polypeptide Synthesis and Folding: RGD-miniproteins described below were synthesized using standard Fmoc-based solid phase peptide synthesis with a CS Bio CS336S automated synthesizer (Menlo Park, Calif.). The polypeptides originally contained a lysine at position 15 that was mutated to a serine to facilitate chemical coupling of imaging probes specifically to the N-terminus. Crude polypeptide was purified by reversed phase HPLC using a $C_{18}$ column (Vydac). The correct molecular mass was verified using electrospray mass spectrometry. Polypeptides were folded with the assistance of dimethyl sulfoxide and glutathione. Folded polypeptides exhibit a distinct chromatographic profile that allows them to be purified from unfolded or misfolded species by reversed-phase HPLC.

Figure 9:
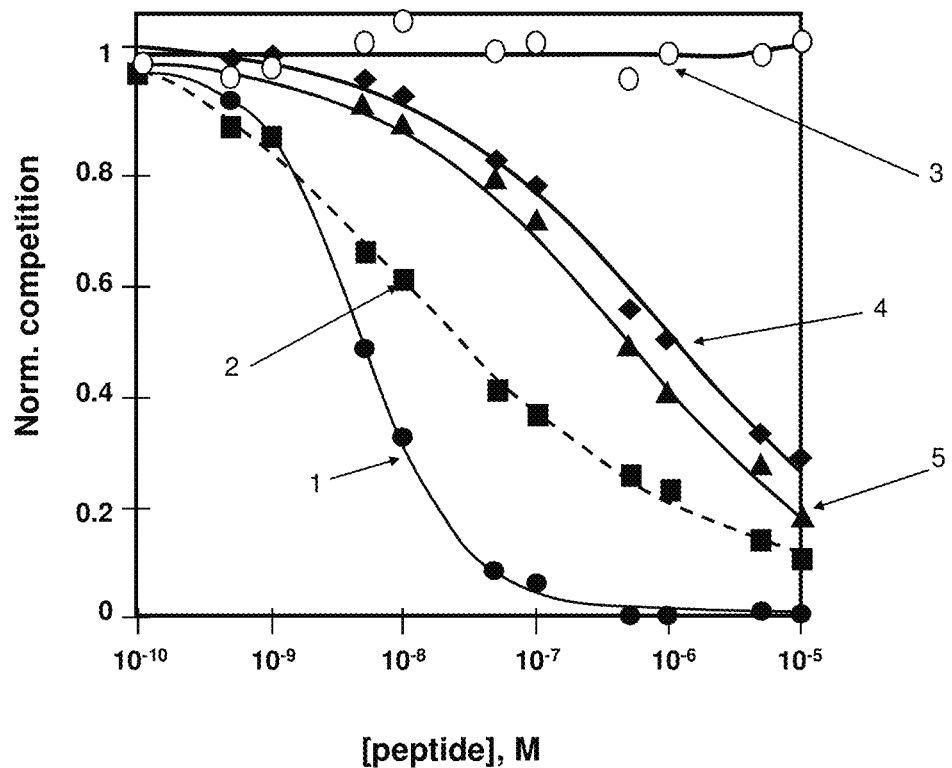
FIG. 9 is a graph showing normalized competition plotted against peptide concentration in an integrin-binding assay on U87MG glioblastoma cells. Relative polypeptide binding affinity was measured by competition of $^{125}$I-labeled echistatin with unlabeled echistatin (line 1), 2.5D (line 2), FN-RGD (line 5), c(RGDyK) (SEQ ID NO: 140) (line 4), and scrambled FN-RDG (line 3).

Binding to tumor cells overexpressing $\alpha_v\beta_3$ integrins: Referring now to FIG. 9, RGD-miniproteins were tested for their ability to compete for cell surface integrin binding with $^{125}$1-labeled echistatin, a protein which binds the $\alpha_v\beta_3$ integrin with a $K_D$ of 0.3 nM. U87MG glioblastoma cells, which express ~$10^5$ $\alpha_v\beta_3$ integrin receptors per cell, were used for these studies. We compared the receptor binding affinity of loop-grafted FN-RGD (designated FN-RGD), and three of our affinity-matured mutants, designated Miniprotein 1.5B, 2.5D, or 2.5F (see Table 2), to that of c(RGDyK) (SEQ ID NO: 140), a pentapeptide currently under preclinical development for molecular imaging applications. An EETI-based polypeptide with a scrambled RDG amino acid sequence, designated FN-RDG, served as a negative control. All of the RGD-containing peptides inhibited the binding of $^{125}$1-labeled echistatin to U87MG cells in a dose dependent manner. Their $IC_{50}$ values (corresponding to data in FIG. 9) are shown in the Table 5 below.

TABLE 5

IC50 values of 1.5B, 2.5D and 2.5F

|  | Cy5.5 | Echistatin | c(RGDyK) (SEQ ID NO: 140) | Loop-grafted FN-RGD | Miniprotein 1.5B | Miniprotein 2.5D | Miniprotein 2.5F |
| --- | --- | --- | --- | --- | --- | --- | --- |
| $IC_{50}$ | No | 4.9 ± 1.0 nM | 860 ± 400 nM | 370 ± 150 nM | 13 ± 3.3 nM | 16 ± 6.1 nM | 26 ± 5.4 nM |
| $IC_{50}$ | Yes | 2.6 ± 0.2 nM | 62.9 ± 4.1 nM | 33.9 ± 13 nM | 6.4 ± 3.3 nM | 4.2 ± 0.9 nM | 3.4 ± 0.8 nM |

The above table shows competition binding of engineered peptides with $^{125}$I-echistatin to U87MG tumor cells. Half-maximal inhibitory concentrations (IC$_{50}$) represent the standard deviation of data measured on at least three separate days. Data for unlabeled and Cy5.5-labeled peptides are shown. Site-specific labeling of RGD miniproteins with a near-infrared optical imaging probe: The free N-terminal amine of our polypeptides was used for site-specific attachment of Cy5.5, a near infrared imaging probe.

Our evolved mutants were shown to bind to U87MG cells with a 50 to 80-fold higher affinity than both of the parental loop-grafted FN-RGD and c(RGDyK) (SEQ ID NO: 140).

Figure 10:
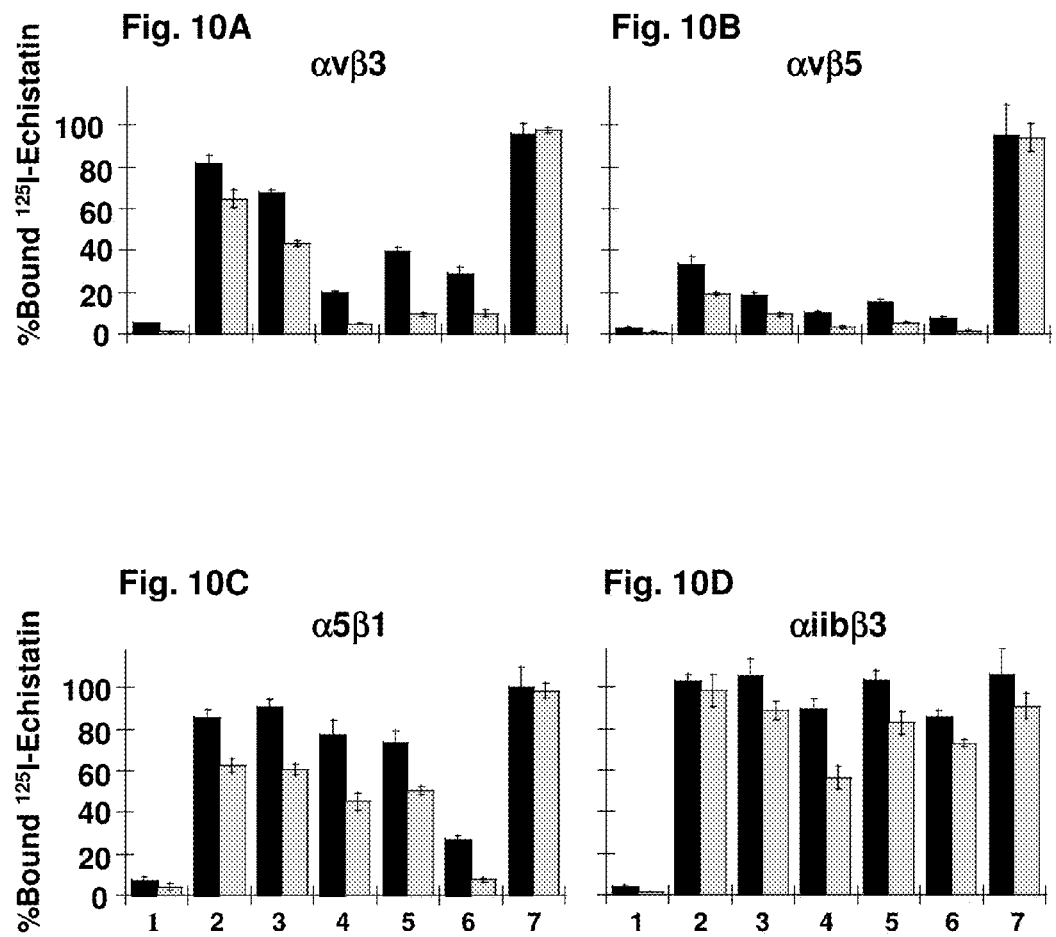
FIG. 10A through FIG. 10D is a series of histograms showing binding specificities to integrins $\alpha_v\beta_3$, $\alpha_v\beta_5$, $\alpha_5\beta_1$, and $\alpha_{iib}\beta_3$ for engineered EETI-RGD peptides compared to controls. Error bars represent experiments performed in triplicate. Competition binding of 0.06 nM $^{125}$I echistatin with 5 nM (black bars) and 50 nM (grey bars) unlabeled peptide to plate-coated integrins was measured. 1=echistatin; 2=c(RGDyK) (SEQ ID NO: 140); 3=FN-RGD; 4=1.5B; 4=2.5D; 5=2.5F; 6=FN-RDG. The engineered peptides have very little binding to $\alpha_{iib}\beta_3$ integrin.
Figure 12A:
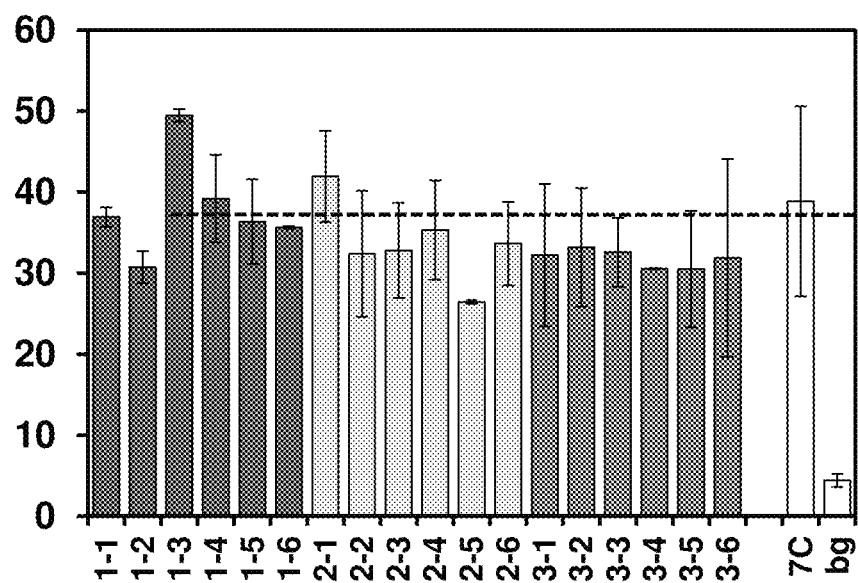
FIGS. 12A and 12B are a pair of bar graphs showing binding results of mutagenesis of AgRP loops 1-3 using degenerate codons. Binding of 50 nM integrin to yeast-displayed AgRP peptide clones from sort round 4 of degenerate codon libraries is shown. Top graph shows binding to αvβ3 integrin; bottom graph shows binding to αiibβ3 integrin. Background, marked "bg" indicates cells stained with fluorescein-conjugated anti-integrin antibodies only. Numbers are arbitrary fluorescence units.
Figure 12B:
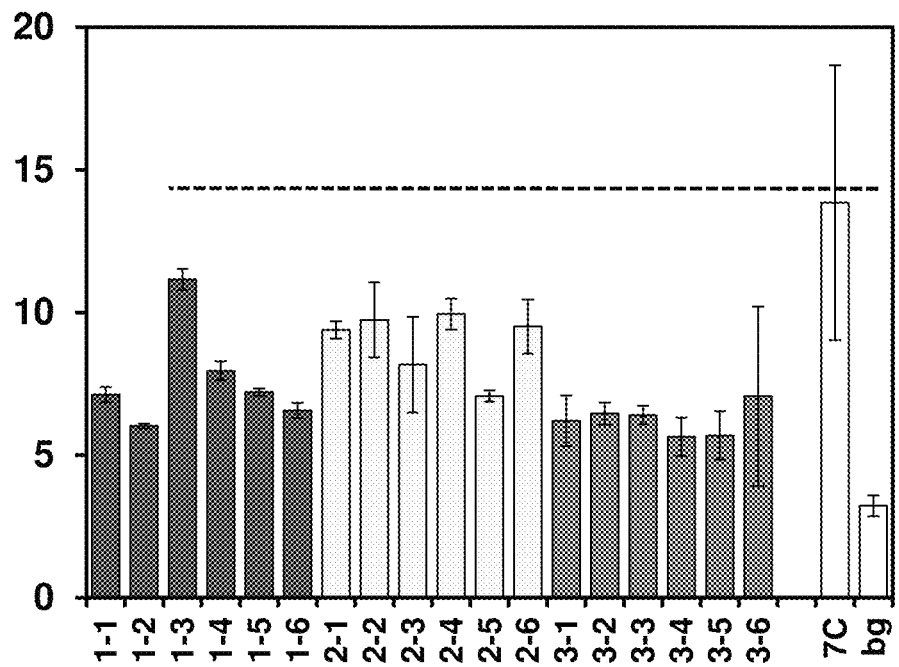

Unique Integrin Binding Specificities: Since U87MG cells have been shown to express $\alpha_v\beta_3$, $\alpha_v\beta_5$, and $\alpha_5\beta_1$ integrins, it was necessary to use another means to measure integrin-binding specificity. This was done by competition of $^{125}$I-echistatin to detergent-solubilized integrin receptors coated onto microtiter plates (see FIG. 10). As expected, echistatin binds strongly to all of the tested integrins. The scrambled FN-RDG miniprotein, the negative control, did not bind to any of the integrins used in this study. All peptides bound to $\alpha_v\beta_3$ and $\alpha_v\beta_5$ integrins to some degree, with the engineered RGD-miniproteins 1.5B, 2.5D, and 2.5F showing the strongest levels of binding. This is consistent with previous studies which have shown $\alpha_v$ integrin receptors can accommodate a wide range of RGD-containing cyclic structures. Interestingly, the RGD-miniprotein 2.5F binds with strong affinity to the $\alpha_5\beta_1$ integrin subtype, while RGD-miniproteins 1.5B and 2.5D exhibit only minimal binding to this receptor. However, since $\alpha_5\beta_1$ integrins are expressed on many tumors and are all involved in mediating angiogenesis and metastasis, a broad spectrum agent that targets all three integrins will be useful for diagnostic and therapeutic applications. With the exception of echistatin, all of the RGD-containing peptides bound weakly to the $\alpha_{IIb}\beta_3$ receptor, showing the specificity of the present peptides for the αv and α5-containing integrin heterodimers. This characteristic is valuable for molecular imaging and therapeutic applications, since binding to $\alpha_{IIb}\beta_3$ on platelet cells prevents blood clotting and would lead to non-specific in vivo effects.

```
                                               (SEQ ID NO: 28)
1.5B: GCTIGRGDWAPSECKQDSDCLAGCVCGPNGFCG (SEQ ID NO: 49)
2.5 D GCPQGRGDWAPTSCKQDSDCRAGCVCGPNGFCG (SEQ ID NO: 50)
2.5F  GCPRPRGDNPPLTCKQDSDCLAGCVCGPNGFCG
```

Viewing 1.5B and 2.5D together, one observes the identical "GRGDWAP" (SEQ ID NO: 108) motif that these peptides have in common, and would be expected to confer the integrin specificity observed. On the other hand, the unique specificity of 2.5F (strong affinity to the $\alpha_5\beta_1$ integrin subtype), is reflected in the additional proline residues.

The proline rich sequence of 2.5F may constrain the binding epitope into a favorable conformation for these high affinity interactions. We are now pursuing molecular modeling and structural studies to provide insight into the unique binding integrin specificity of this peptide.

In another experiment, the ability of engineered knottin peptides to block U87MG cell adhesion to vitronectin- and fibronectin-coated microtiter plates. Vitronectin is a natural ligand for several integrins, including $\alpha_v\beta_3$ and $\alpha_v\beta_5$. The RGD-containing peptides were all able to inhibit U87MG cell adhesion to vitronectin-coated plates in a dose-responsive manner. The IC$_{50}$ values of cell adhesion correlated with the $^{125}$I-echistatin competition binding data (above), indicating that inhibition of cell adhesion is directly related to integrin binding events. Fibronectin also binds to several integrins, (including $\alpha_v\beta_3$ and $\alpha_5\beta_1$), but the $\alpha_5\beta_1$ integrin receptor is generally selective for fibronectin. We found that only echistatin and knottin peptide 2.5F were able to block U87MG cell adhesion to fibronectin-coated plates, consistent with their ability to bind both $\alpha_v$ and $\alpha_5\beta_1$ integrins with high affinity. The FN-RDG2 negative control was not able to inhibit U87MG cell adhesion to vitronectin or fibronectin, as expected.

Engineered Knottin Peptides Exhibit High Stability in Serum

The stability of the knottin peptide 2.5D upon exposure to human or mouse serum at 37° C. was measured. Reversed-phase HPLC was used to quantify the amount of intact knottin peptide remaining at various times post incubation. We found that approximately 90% of the peptide remained after incubation for 24 h in human and mouse serum, with approximately 70% remaining after 96 h.

Soluble Expression of Engineered AgRP Peptides

*P. pastoris* was chosen for recombinant expression of the engineered AgRP peptides, as it has been successfully used to express proteins with disulfide bonds and significant secondary structure. The eukaryotic quality control machinery in the secretory pathway of yeast should help ensure proper folding and high levels of soluble expression of the AgRP peptides, which have four disulfide bonds and complex folds. Using conditions and procedures described in the *P. pastoris* expression kit (Invitrogen K1750-01), AgRP clones 6C, 7A (named above as 5E), 7C, 7E, and 7J (named above as 6B) were produced in yields of 3-10 mg/L culture.

TABLE 6

Sequences of Additional AgRP mutants isolated from flow cytometry sort rounds 6 and 7.

| Clone | Loop 4 sequence |
|---|---|
| 7A (5E) (SEQ ID NO: 114) | GCVRLHESCLGQQVPCCDPAATCYCSGRGDNDLVCYCR |
| 7B (SEQ ID NO: 115) | GCVRLHESCLGQQVPCCDPAATCYCKGRGDARLQCYCR |
| 7E (SEQ ID NO: 116) | GCVRLHESCLGQQVPCCDPAATCYCVGRGDDNLKCYCR |
| 7J (6B) (SEQ ID NO: 90) | GCVRLHESCLGQQVPCCDPAATCYCEGRGDRDMKCYCR |

The engineered AgRP peptides were expressed with N-terminal FLAG epitope tags (DYKDDDDK) SEQ ID NO: 138 and C-terminal hexahistidine tags for use as handles in purification and cell binding assays through antibody detection. The expressed peptides were purified by Ni-affinity chromatography and determined to be >90% pure by reversed-phase HPLC and gel-filtration chromatography. SDS-PAGE analysis was performed on reduced and non-reduced. Peptide composition was confirmed and exact concentrations were determined by amino acid analysis (data not shown), and masses were obtained by MALDI-TOF mass spectrometry.

To determine whether the FLAG and hexahistidine tags would interfere with αvβ3 integrin binding, one of the AgRP clones, 7C, was prepared without epitope tags by solid-phase peptide synthesis using standard Fmoc chemistry. The crude, reduced peptide was purified by reversed-phase HPLC, then oxidized with glutathione and DMSO, as previously described. The fully oxidized peptide was purified from unfolded and misfolded states by reversed-phase HPLC, and the mass was confirmed by mass spectrometry.

To compare the αvβ3 integrin binding affinities of synthetic and recombinant AgRP peptides, a competition binding assay using U87MG glioblastoma cells, which express approximately $10^5$ αvβ3 receptors per cell, as well as αvβ5 and α5β1 integrins. Recombinant AgRP peptide 7C (20 nM) was pre-incubated with $10^5$ cells and binding was then competed off using synthetic AgRP peptide 7C at concentrations ranging from 1 nM to 500 nM. After washing, the cells were stained with a fluorescein-conjugated anti-FLAG antibody and then analyzed by flow cytometry. Competition of synthetic peptide by recombinant peptide was performed analogously. These experiments gave essentially identical half-maximal inhibitory concentration ($IC_{50}$) values (22±3 nM and 23±6 nM, respectively; suggesting that both recombinant and synthetic AgRP peptides are correctly folded and that the FLAG and His epitope tags on the recombinant peptide do not interfere with integrin binding.

Integrin Binding Affinity and Specificity of Engineered AgRP Peptides.

Direct equilibrium binding titrations of the recombinant engineered AgRP peptides were performed on U87MG glioblastoma cells. Peptides were incubated with cells for 3 h at 4° C., followed by staining with a fluorescein-conjugated anti-His antibody and analysis by flow cytometry. Equilibrium binding constant ($K_D$) values were obtained by fitting plots of concentration versus mean fluorescence intensity to a sigmoidal curve using KaleidaGraph software.

TABLE 7

Binding and cell adhesion data summary for engineered AgRP peptides.

| | binding ($K_D$; nM) | | adhesion ($IC_{50}$; nM) |
|---|---|---|---|
| Clone | U87MG | K562-αvβ3 | K562-αvβ3 |
| 6C | 13 ± 2 | 15 ± 4 | 650 ± 250 |
| 7A | 0.78 ± 0.37 | 0.89 ± 0.36 | 61 ± 19 |
| 7C | 1.8 ± 0.6 | 2.4 ± 0.8 | 12 ± 6 |
| 7E | 1.4 ± 0.5 | 1.6 ± 1.1 | 9.9 ± 5.8 |
| 7J | 8.3 ± 1.8 | 16 ± 8 | 200 ± 150 |
| Echistatin | nd | nd | 3.2 ± 2.7 | nd = not determined

As shown above, all five engineered AgRP peptides tested bound with low nanomolar to high picomolar affinity, and the tightest binder, 7A, isolated from sort round 7, showed 17-fold improvement over the worst binder, 6C, isolated from sort round 6. The saturation levels for the different clones vary roughly with affinity. This suggests that the mutants have different binding off-rates that dictate their $K_D$ values, with weaker binding clones having faster off-rates. Alternatively, the differences in saturation levels could be due to integrin receptor clustering that is differentially elicited or stabilized by clones with varying affinities.

To determine the binding specificities of the AgRP peptides for αvβ3 integrin versus the αvβ5 and α5β1 integrins also expressed on U87MG cells, K562 leukemia cells that had been stably transfected with individual α and β integrin subunits were used. The engineered AgRP peptides were tested for binding to untransfected K562 cells, which intrinsically express α5β1 integrin. Equilibrium binding assays were performed on the untransfected K562 cells as described above for the U87MG cells. Three peptide concentrations were tested. Negligible signal over background levels (cells stained with fluorescein-conjugated anti-His antibody alone) even at 500 nM, the highest concentration tested, was observed. This demonstrated that the engineered AgRP peptides do not appreciably bind to α5β1 integrin, and that the K562 cells transfected to express other integrins would be useful in determining integrin-binding specificity.

The engineered AgRP peptides were tested for binding to K562 cells expressing αvβ5 αiiiβ3 or αvβ3 integrins. The peptides were tested at three concentrations with very little signal over background for cells expressing αvβ5 integrin, even at 500 nM, the highest concentration. The peptides bound weakly to the K562 cells expressing αiiβ3 integrins and, as expected, strongly to the K562 cells expressing αvβ3 integrins. In order to determine $K_D$ values for the engineered AgRP peptides against K562-αiiβ3 and K562-αvβ3 cells, binding titrations were done over a larger range of concentrations. $K_D$ values for AgRP peptide binding to K562-αvβ3 cells were essentially identical to the $K_D$ values obtained for the U87MG cells, indicating that binding of engineered AgRP peptides to U87MG cells is mediated by αvβ3 integrin (Table 7). $K_D$ values for peptide binding to K562-αiibβ3 cells could not be determined because binding was still increasing at the highest concentration (5 μM) of peptides tested. However, from the data, it may be estimated that the $K_D$ values for AgRP peptide binding to the K562-αiibβ3 cells are much greater than 100 nM.

Inhibition of Vitronectin-Mediated Cell Adhesion by Engineered AgRP Peptides.

To determine whether the engineered AgRP peptides could inhibit cell adhesion mediated by vitronectin, the primary ligand for αvβ3 integrin, K562-αvβ3 cells were incubated with varying concentrations of peptides in microtiter wells coated with vitronectin to determine the ability of the peptides to inhibit cell adhesion. The engineered AgRP peptides were able to block vitronectin-mediated adhesion of the K562-αvβ3 cells with $IC_{50}$ values ranging from 9.9 to 650 nM (Table 7). The $IC_{50}$ values for inhibition of cell adhesion were 6- to 67-fold greater than the $K_D$ values against the K562-αvβ3 cells. This difference may be a result of multivalent interactions between the cell surface αvβ3 integrins and the immobilized vitronectin, thereby making it more difficult for the peptides to compete.

Whether the engineered AgRP peptides could block vitronectin-mediated adhesion to the U87MG cells was tested using an analogous assay. However, adhesion of the U87MG cells was only partially blocked by the peptides, even at concentrations up to 1 μM. In contrast, the RGD-containing disintegrin echistatin, which binds strongly to αvβ3, αvβ5, α5β1, and αiibβ3 integrins, blocked U87MG cell adhesion to vitronectin with an $IC_{50}$ of 5.8 nM. The AgRP peptides may not effectively block U87MG adhesion compared to the K562-αvβ3 cells because the αvβ5 integrins co-expressed on the surface of the U87MG cells could also contribute to vitronectin-mediated adhesion and compensate for the loss of αvβ3 integrin function. These data provide further evidence that the engineered AgRP peptides bind to αvβ3 but not to αvβ5 integrins.

Mutagenesis of AgRP Loops 1, 2 and 3.

Modification of the remaining AgRP loops (loops 1, 2, or 3) were studied for their effect on integrin binding affinity or specificity, and/or on the tolerance of the other AgRP loops to mutagenesis for further protein engineering studies. This is illustrated as follows:

```
                                            (SEQ ID NO: 117)
GCXXXXXXXCLGQQVPCCDPAATCYCYGRGDNDLRCYCR
```

In this sequence loops one and four are underlined.

```
                                            (SEQ ID NO: 118)
GCVRLHESCXXXXXXXCCDPAATCYCYGRGDNDLRCYCR
```

In this sequence loops two and four are underlined.

```
                                            (SEQ ID NO: 119)
GCVRLHESCLGQQVPCCXXXXXXCYCYGRGDNDLRCYCR
```

In this sequence loops three and four are underlined. Loop 4 contains the engineered regions previously described, and loops 1-3 are being modified in this example.

Yeast-displayed libraries using clone 7C as a starting point, with loops 1, 2, or 3 as shown above individually substituted with randomized sequences using degenerate codons were prepared. These randomized loop libraries were subjected to four rounds of screening by FACS to ascertain whether it would be possible to select mutants that retained binding to αvβ3 integrin. In each screening round, the yeast were labeled for peptide expression using the cMyc epitope and incubated with 50 nM αvβ3 integrin, followed by staining with fluorescently labeled secondary antibodies. Although the initial libraries showed significantly diminished binding to αvβ3 integrin compared to the parent clone 7C, mutants that retained affinity for αvβ3 integrin were enriched after four rounds of screening (data not shown).

After sort round four, six yeast-displayed clones were chosen at random from each loop-mutagenized library (Table 8), and were tested for their ability to bind integrins.

TABLE 8

Modified Loop Sequences of AgRP Loops 1, 2 and 3

| Clone[a] | Modified Loop Sequence |
|---|---|
| 1-1 | ASGSGDP SEQ ID NO: 120 |
| 1-2 | RPLGDAG SEQ ID NO: 121 |
| 1-3 | LAGLSGP SEQ ID NO: 122 |
| 1-4 | RSASVGG SEQ ID NO: 123 |
| 1-5 | IASGLFG SEQ ID NO: 124 |
| 1-6 | DLYGSHD SEQ ID NO: 125 |
| 2-1 | GGSVGVE SEQ ID NO: 126 |
| 2-2 | DPRVGVR SEQ ID NO: 127 |
| 2-3 | ADTLMAA SEQ ID NO: 128 |
| 2-4 | EWGRGGD SEQ ID NO: 129 |
| 2-5 | GSWGTLA SEQ ID NO: 130 |
| 2-6 | WGSILGH SEQ ID NO: 131 |
| 3-1 | GTPKPE SEQ ID NO: 132 |
| 3-2 | SRSDAH SEQ ID NO: 133 |
| 3-3 | SGLGNR SEQ ID NO: 134 |

TABLE 8-continued

Modified Loop Sequences of AgRP Loops 1, 2 and 3

| Clone[a] | Modified Loop Sequence |
|---|---|
| 3-4 | QGREQS SEQ ID NO: 135 |
| 3-5 | TVTNSR SEQ ID NO: 136 |
| 3-6 | TSKQHH SEQ ID NO: 137 |

[a]First number indicates mutated loop, second number indicates clone number.

Yeast displaying each mutant were treated with 50 nM αvβ3, 50 nM αiib β3, or 50 nM αv β5 integrin, then stained with an appropriate fluorescein-conjugated anti-integrin antibody and analyzed by flow cytometry. None of the clones bound to αv β5 integrin (data not shown). In contrast, all of the clones bound αvβ3 integrin at levels close to that of the parent clone 7C. The clones also weakly bound to αiib β3 integrin, albeit at lower levels compared to the parent clone 7C. The ratio of αv β3 binding to αiib β3 binding was increased for all of the clones over the parent clone 7C. These data suggest that AgRP loops 1, 2, and 3 are in principle tolerant to mutagenesis and they may contribute to binding specificity through either direct integrin contacts or through structural changes in the engineered AgRP peptides.

The above binding studies demonstrate that the engineered AgRP peptides are selective for αv β3 over several other integrins that also recognize RGD sequences, namely αv β5, α β1, and αiib β3. The engineered peptides did not bind at all to αv β5 or α5 β1, whereas weak binding was observed against αiib β3 integrin. It has been a challenge in the past to select peptides that are selective for αv β3 over αiib β3 and vice versa. Without wishing to be bound by any theory, it is believed that the examples here provide guidance for design of such selective peptides. RGD ligands bind to αv β3 and αiib β3 near β-propeller loops of the a subunit that form a cap subdomain and a so-called specificity-determining loop in the β3 subunit. Structural differences between αv and αiib are responsible for variations in the cap subdomain and the β3 specificity-determining loop, while the remainder of the αv and αiib β-propeller structures are conserved. Consequently, specificity of RGD-containing peptides for αv β3 versus αiib β3 is controlled by the deeper β-propeller pocket of αiib. The Arg residue in RGD must be in an extended conformation to reach into the αiib pocket to hydrogen bond with αiib-Asp224, while αv-Asp150 and αv-Asp218 residues are found in a shallower pocket. Furthermore, αiib β3 shows a preference for aliphatic residues flanking RGD, as αv-Asp218 is replaced by a hydrophobic Phe231 in αiib. It is postulated that the engineered AgRP peptides tested here have predominantly hydrophilic or charged residues flanking RGD, which may clash with αiib-Phe231.

Mutagenesis and Screening of AgRP Loop 1, 2, and 3 Libraries

Libraries of AgRP clone 7C (Table 8) with loop 1, 2, or 3 substituted with 7, 7, or 6 randomized amino acid residues, respectively, were prepared as described above. For screening, each library was incubated with 50 nM αv β3 integrin and $2\times10^7$ cells were sorted by FACS as described above. Three additional rounds of FACS were performed to enrich for a pool of clones that retained binding to αv β3 integrin. In these subsequent sort rounds the libraries were over sampled at least 10-fold to ensure diversity was maintained, but the integrin concentration was kept at 50 nM. Clones from the fourth round of sorting were isolated and sequenced as described above.

Recombinant and Synthetic Production of Engineered AgRP Mutants

Peptides were expressed recombinantly using the Multi-Copy *Pichia* Expression Kit (Invitrogen K1750-01). The open reading frame encoding the clone of interest was inserted into pPIC9K plasmid between the AvrII and MluI restriction sites. In addition, DNA encoding for a FLAG tag was inserted between SnaBI and AvrII sites, while DNA encoding for a hexahistidine tag was inserted between MluI and NotI restriction sites. ~10 µg of plasmid was linearized by cutting with SacI then electroporated into the *P. pastoris* strain GS115. Yeast were allowed to recover on RDB plates and were then transferred to YPD plates containing 4 mg/mL geneticin. Geneticin-resistant colonies were grown in BMGY and then induced in BMMY. Cultures were grown for 3 days with methanol concentration maintained at ~0.5%.

AgRP Clone 7C was also prepared without FLAG or His tags using solid-phase peptide synthesis on a CS Bio peptide synthesizer (Menlo Park, Calif.) using standard Fmoc chemistry. The peptide was purified by reversed-phase HPLC and then folded using 4 M guanidine, 10 mM reduced glutathione, 2 mM oxidized glutathione, and 0.5 M DMSO at pH 7.5. The correctly folded peptide was separated from unfolded and partly folded peptides by reversed-phase HPLC, where it appeared as a single peak with a shorter retention time than unfolded or misfolded precursors. All peptides, recombinant and synthetic, were characterized by amino acid analysis (AAA Service Laboratory, Damascus, Oreg.) and MALDI-TOF mass spectrometry (Stanford Protein and Nucleic Acid Facility), which gave a single peak corresponding to the fully folded protein containing four disulfide bonds.

Cell Binding Assays

All cell lines were cultured at 37° C. with 5% $CO_2$. Adherent U87MG cells were obtained from ATCC and cultured in DMEM media (Gibco 11995) supplemented with 10% fetal bovine serum. Untransfected K562 cells ($\alpha 5$ $\beta 1$-positive) were obtained from ATCC and cultured in suspension in IMDM media (Gibco 12440) supplemented with 10% fetal bovine serum. K562 cells stably transfected with $\alpha v$ $\beta 3$, $\alpha v$ $\beta 5$, or $\alpha iib$ $\beta 3$ integrins were obtained from S. Blystone (Blystone, S. D., Graham, I. L., Lindberg, F. P. & Brown, E. J. (1994). Integrin avb3 differentially regulates adhesive and phagocytic functions of the fibronectin receptor a5b1. J. Cell Biol. 127, 1129-1137) and were grown in media supplemented with 10 µg/mL geneticin. Equilibrium binding assays were performed with $10^5$ cells per reaction. Cells were suspended in IBB with varying amounts of engineered AgRP peptide at 4° C. for 3 h with gentle rocking. The cells were washed and resuspended in BPBS with a 1:40 dilution of fluorescein-conjugated anti-6X-His antibody (Bethyl A190-113F) and incubated on ice for 20 min. After washing, the cells were analyzed by flow cytometry using a BD FACSCalibur instrument and CellQuest software (Becton Dickinson, Franklin Lakes, N.J.). Mean fluorescence intensity values for each cell population was plotted against concentration on a log scale. Data was fit to sigmoidal curves to obtain equilibrium dissociation constants using KaleidaGraph (Synergy Software), and is presented as average values with standard deviations. Each assay was performed a minimum of three times.

Modifications of EETI-II Loops 2 and 3

This example involves the creation of EETI loop-substituted libraries in which a single cysteine-flanked loop of EETI (loop 2 or loop 3) was substituted with randomized amino acid sequences of variegated lengths in order to explore the tolerance of the EETI scaffold for different loop sizes and amino acid compositions. Libraries were generated by overlap extension PCR using degenerate NNS oligonucleotides (N=any nucleotide, S=G or C). Six libraries in total were generated: two libraries of EETI loop 2 variants with substitution lengths of 7 amino acids (EL2-7) and 9 amino acids (EL2-9), and four libraries of EETI loop 3 variants with substitution lengths of 6 amino acids (EL3-6), 7 amino acids (EL3-7), 8 amino acids (EL3-8), and 9 amino acids (EL3-9). EETI loop 1, which is responsible for binding to trypsin, was used as a handle to probe the structural integrity of the EETI loop-substituted clones. Library DNA was electroporated into the *S. cerevisiae* EBY100 strain with linearized yeast-display plasmid as previously described. By performing dilution plating, it was estimated that the sizes of the loop-substituted libraries ranged from $5 \times 10^6$-$1 \times 10^7$ transformants. At least 50 clones from each of the six original libraries were sequenced to confirm that the substituted loops were of the correct lengths and had diverse amino acid compositions. The amino acid frequencies of the loop-substituted regions were similar to those expected for a degenerate NNS codon library.

Isolation of EETI Loop-Substituted Trypsin-Binding Clones

It has been previously demonstrated that retention of the correct pairings of disulfide-bonded cystines in EETI can be examined by testing for trypsin binding. Each of the EETI loop-substituted libraries was screened for clones that were both displayed on the yeast cell surface (as detected by indirect immunofluorescence against the C-terminal cMyc epitope tag) and properly folded (as determined by their ability to bind fluorescently-labeled trypsin) using dual-color fluorescence-activated cell sorting (FACS). By performing repeated rounds of FACS on each yeast-displayed library, each time collecting the top 1-2% of trypsin-binding clones, EETI loop-substituted clones that retained the highest levels of trypsin-binding ability were enriched. After four rounds of sorting, a pool of clones that showed moderate to wild-type levels of trypsin binding had been isolated from each library.

The amino acid frequencies of the enriched library populations also differed from their original, unsorted counterparts. Notably, glycine was enriched in all EETI loop-substituted libraries compared to the starting libraries, and cysteine virtually disappeared from all trypsin-binding clones, except in the EL3-7 library. Apart from glycine, hydrophilic residues predominated in the loop-substituted positions of enriched clones, which was expected given their solvent-accessibility. EETI loop 2-substituted clones were relatively tolerant of diversity across all loop positions. Glycine comprised approximately 25-30% of all amino acids in EETI loop 2-substituted trypsin-binding clones at all positions in the loop except the second. On average, EETI loop 2-substituted sequences of both 7- and 9-amino acids contained approximately 2 glycine residues per clone. Proline and serine, residues that commonly populate turn segments, predominated in the second position of EETI loop 2-substituted variants (FIG. 5).

The overall diversities of EETI loop 3-substituted clones were slightly higher than those of loop 2-substituted clones. The greatest levels of diversity occurred in the middle positions of the substituted loops of loop 3 variants while the first, penultimate, and final positions had the lowest diversities. Approximately 75% of all EL3-9 clones began with one of four preferred residues: asparagine, arginine, valine, and histidine. The most common amino acids for the penultimate and final positions of EETI loop 3 were glycine and tyrosine, respectively; nearly a quarter of all loop 3 substituted sequences from enriched clones ended in a glycine-tyrosine doublet. We observed the aforementioned trends in tolerated EETI loop 3 substituted clones across all loop lengths.

EETI loop 3 was very tolerant of substitution with 6, 8, and 9 amino acid sequences, but surprisingly did not appear to be tolerant of a 7-amino acid loop.

The Table 9 below show frequencies of amino acid substitutions in different positions, taken from the enriched library:

TABLE 9

| Amino Acid Substitutions | | | | | | | |
|---|---|---|---|---|---|---|---|
| EETI Loop 3 Substituted with 9 Amino Acids | | | | | | | |
| Loop Position | 1 | N (36%) | R (15%) | V (15%) | | | |
| | 2 | R (19%) | K (15%) | T (13%) | N (10%) | P (10%) | |
| | 3 | N (21%) | T (21%) | R (11%) | | | |
| | 4 | N (17%) | T (17%) | R (15%) | | | |
| | 5 | R (19%) | G (13%) | N (12%) | H (10%) | | |
| | 6 | G (17%) | N (13%) | T (13%) | R (12%) | D (10%) | |
| | 7 | P (12%) | T (12%) | L (10%) | M (10%) | R (10%) | |
| | 8 | G (60%) | S (17%) | | | | |
| | 9 | Y (85%) | | | | | |
| EETI Loop 3 Substituted with 8 Amino Acids | | | | | | | |
| Loop Position | 1 | R (27%) | I (20%) | V (12%) | N (11%) | L (9%) | |
| | 2 | H (16%) | R (12%) | N (11%) | G (9%) | K (9%) | S (9%) |
| | 3 | S (18%) | N (16%) | R (12%) | T (12%) | | |
| | 4 | G (20%) | R (18%) | K (12%) | T (9%) | | |
| | 5 | R (14%) | H (11%) | G (11%) | Q (11%) | | |
| | 6 | R (16%) | G (14%) | H (9%) | | | |
| | 7 | G (38%) | S (14%) | A (11%) | R (11%) | K (9%) | |
| | 8 | Y (50%) | F (14%) | T (11%) | | | |
| EETI Loop 3 Substituted with 7 Amino Acids | | | | | | | |
| Loop Position | 1 | R (18%) | N (17%) | D (11%) | L (11%) | I (9%) | S (9%) |
| | 2 | R (14%) | S (12%) | G (11%) | L (11%) | P (11%) | T (9%) |
| | 3 | G (18%) | S (16%) | N (11%) | P (11%) | R (9%) | T (9%) |
| | 4 | P (12%) | T (12%) | S (9%) | Y (9%) | | |
| | 5 | C (14%) | G (14%) | P (12%) | R (9%) | T (9%) | |
| | 6 | G (36%) | R (20%) | A (9%) | | | |
| | 7 | Y (38%) | F (20%) | C (18%) | | | |
| EETI Loop 3 Substituted with 6 Amino Acids | | | | | | | |
| Loop Position | 1 | D (27%) | N (27%) | H (18%) | | | |
| | 2 | T (21%) | K (10%) | P (10%) | Q (10%) | R (10%) | S (10%) |
| | 3 | R (24%) | D (10%) | L (10%) | | | |
| | 4 | S (34%) | T (14%) | D (10%) | | | |
| | 5 | G (34%) | R (16%) | N (14%) | | | |
| | 6 | Y (31%) | T (23%) | | | | |
| EETI Loop 2 Substituted with 7 Amino Acids | | | | | | | |
| Loop Position | 1 | G (32%) | S (19%) | V (9%) | | | |
| | 2 | P (21%) | S (19%) | V (9%) | | | |
| | 3 | G (26%) | S (13%) | V (9%) | | | |
| | 4 | G (24%) | L (11%) | A (9%) | | | |
| | 5 | G (43%) | S (13%) | | | | |
| | 6 | G (21%) | S (21%) | L (13%) | V (9%) | | |
| | 7 | G (19%) | S (15%) | R (13%) | V (11%) | L (9%) | |
| | 8 | S (23%) | G (17%) | R (11%) | | | |
| | 9 | G (38%) | P (13%) | A (9%) | Q (9%) | S (9%) | |
| EETI Loop 2 Substituted with 9 Amino Acids | | | | | | | |
| Loop Position | 1 | G (26%) | D (18%) | V (11%) | N (10%) | | |
| | 2 | P (44%) | G (21%) | | | | |
| | 3 | G (41%) | A (10%) | | | | |
| | 4 | G (21%) | L (13%) | V (11%) | A (10%) | | |
| | 5 | G (33%) | S (15%) | R (10%) | | | |
| | 6 | G (38%) | S (13%) | | | | |
| | 7 | G (44%) | T (11%) | E (10%) | | | |

Imaging

Site-specific labeling with imaging probe: The free N-terminal amine of the engineered peptide was used for site-specific attachment of Cy5.5, a near-infrared imaging probe. Cy5.5 monofunctional N-hydroxysuccinimide ester (Amersham Biosciences) was covalently-coupled to all of the polypeptides described above, and the complexes were purified by reversed-phase HPLC. The molecular masses of the conjugated polypeptides were confirmed by mass spectrometry (data not shown). Interestingly, Cy5.5 conjugation slightly increased the affinity of the polypeptides to U87MG cells; however, the Cy5.5-labeled FN-RDG negative control exhibited no binding.

In Vivo Optical Imaging of Tumors in Mouse U87MG Xenograft Models

Whole-body imaging of subcutaneous mouse xenografts were imaged with the IVIS 200 system (Xenogen) and quantified with Living Image 2.50.1 software. FIG. 8A shows typical NIR fluorescent images of athymic nude mice bearing subcutaneous U87MG glioblastoma tumors after intravenous (iv) injection of 1.5 nmol of Cy5.5-labeled RGD-miniprotein 2.5D, or the Cy5.5-labeled FN-RDG negative control. The fluorescence intensity of the tumor to normal tissue (T/N) ratio as a function of time is depicted in FIG. 8B, which also includes the corresponding values for iv injection of Cy5.5-labeled loop grafted FN-RGD and c(RGDyK) (SEQ ID NO: 140). The Cy5.5-labeled RGD-miniprotein 2.5D shows approximately a 60% greater T/N ratio at both early and late time points compared to both the FN-RGD and the c(RGDyK) (SEQ ID NO: 140) pentapeptide. These results indicate that integrin binding affinity plays a role in tumor targeting, and provides a strong foundation for clinical translation of RGD-miniproteins as $^{18}$F and $^{64}$Cu-labeled PET imaging probes.

Preparation of Radiolabeled Integrin-Binding Polypeptides for microPET Imaging.

Integrin binding polypeptides are conjugated to $^{18}$F and $^{64}$Cu radioprobes for microPET imaging, which is PET based imaging in small animals. Both radioprobes are studied due to potential differences in metabolism, pharmacokinetics, and biodistribution.

Polypeptide synthesis: Polypeptides are synthesized, folded, purified, and characterized as described above.

Preparation of 4-[$^{18}$F] fluorobenzoyl-labeled polypeptides ([$^{18}$F] FB): [$^{18}$F] FB-labeled polypeptides are prepared by conjugation of the N-terminal amine with N-succinimidyl 4-[$^{18}$F]fluorbenzoate ([$^{18}$F]SFB) under slightly basic conditions as previously described. (See, Chen, X., Liu, S., Hou, Y., Tohme, M., Park, R, Bading, J. R & Conti, P. S. (2004). MicroPET imaging of breast cancer alpha v-integrin expression with $^{64}$Cu-labeled dimeric RGD peptides. Mol Imaging Bioi 6, 350-9; and Chen, X., Park, R, Tohme, M., Shahinian, A H., Bading, J. R & Conti, P. S. (2004). MicroPET and autoradiographic imaging of breast cancer alpha v-integrin expression using $^{18}$F- and $^{64}$Cu labeled RGD peptide. Bioconjug Chem 15, 41-9).

Briefly, [$^{18}$F]SFB are purified by semipreparative HPLC, and the appropriate fraction are collected, diluted with water and trapped by a C-18 cartridge. The cartridge will then be washed with water and blown dried with Argon. [$^{18}$F]SFB is eluted with acetonitrile and rotovapped to dryness. The dried [$^{18}$F]SFB is dissolved in dimethyl sulfoxide and allowed to react with polypeptides in sodium phosphate buffer. Final purification is done by semipreparative HPLC. (See, Zhang, X., Xiong, Z., Wu, Y., Cai, W., Tseng, J. R, Gambhir, S. S. & Chen, X. (2006). Quantitative PET imaging of tumor integrin alphavbeta3 expression with 18F-FRGD2. J Nucl Med 47, 113-21.)

Before $^{18}$F is used, synthesis and purification conditions should be first validated with nonradioactive $^{19}$F-labeled polypeptides, and confirmed using mass spectrometry.

Preparation of DOTA-conjugated polypeptides: 1,4,7,10-tetradodecane-N,N',N'',N'''-tetraacetic acid (DOTA) are conjugated to polypeptides in a manner similar to that described before. (See, Cheng, Z., Xiong, Z., Subbarayan, M., Chen, X. & Gambhir, S. S. (2007).) Briefly, DOTA is activated with 1-ethyl-3-[3-(dimethylamino)propyl]carboiimide at pH 5.5 for 30 minutes (4° C.) with a molar ratio of DOTA:EDC:N-hydroxysulfonosuccinimide=1:1:0.8. Polypeptides are then be added to the prepared sulfosuccinimidyl ester of DOTA in a stoichiometry of 5:1. The reaction is mixed at pH 8.5-9.0 overnight (4° C.). The resulting DOTA-conjugated polypeptides are then purified by reversed phase HPLC on a semipreparative C-18 column, and stored as a lyophilized solid. The mass is verified by electrospray mass spectrometry.

Preparation of [$^{64}$Cu]-DOTA-polypeptide radiotracers: The DOTA-conjugated polypeptides are radiolabeled with $^{64}$Cu by incubation of 5 mCi $^{64}$CuCl$_2$ in 0.1 N NaOAc, pH 5.5 for 1 h at 50° C., and terminated with trifluoroacetic acid. The radiolabeled complex is then be purified by HPLC, dried by rotovap, reconstituted in phosphate buffered saline and passed through a 0.22 11 m filter for animal experiments. Before $^{64}$Cu is used, synthesis and purification conditions should be first validated with nonradioactive "mock" Cu-DOTA-conjugated polypeptides, and confirmed using mass spectrometry.

In-Vitro Characterization of Radiolabeled Integrin-Binding Polypeptides for microPET Imaging Nonradioactive versions of all polypeptides (mock-PET tracers) are tested first to determine if conjugation alters their stability or integrin binding affinity. This is not expected, since the conjugation chemistry will occur at a site in the polypeptide that is distant from the RGD-based integrin binding loop, where prior Cy5.5 conjugation has shown little effect (FIG. 8).

$\alpha_v\beta_3$ integrin binding assay: An $\alpha_v\beta_3$ integrin receptor binding assay is performed to determine the relative affinities of the mock-PET tracers compared to their unlabeled polypeptides. Briefly, $2\times10^5$ U87MG glioblastoma cells are incubated with 0.06 nM $^{125}$I-echistatin in integrin binding buffer (25 mM Tris-HCl, pH 7.4, 150 mM NaCl$_2$ 1 mM CaCl$_2$ 1 mM MgCl$_2$, 1 mM MnCl$_2$, 0.1% BSA), in the presence of increasing concentrations of mock-PET tracers at room temperature. After incubation for 3 h, cells are pelleted by centrifugation at 1500 RPM and washed three times in binding buffer to remove unbound ligands. The radioactivity remaining in the cell pellet is measured by $\gamma$ counting. IC$_{50}$ values are determined by plotting the % competition and using a four-point binding equation (Kaleidagraph) to fit the data.

In-vitro serum stability studies: Nonradioactive mock-PET tracers are incubated with mouse and human serum for various time points at 37° C., and aliquots are acidified and flash frozen. The aliquots are then thawed and microcentrifuged at high speeds to remove aggregates. The soluble fraction is passed through a Sep-Pak C$_{18}$ cartridge (Waters Corp), and rinsed several times with water containing 0.1% TFA (solvent A). The cartridge-bound PET-tracers are eluted with 90% acetonitrile containing 0.1% TFA, lyophilized, and resuspended in solvent A. The solution is passed through a NANOSEP (Pall Corp) 10 kDa cutoff filter and analyzed by reversed-phase HPLC to determine the amount of polypeptide-conjugate remaining.

In-vivo metabolic stability study: The metabolic stability of radiolabeled PET tracers is evaluated in normal athymic nude mice. These animals are sacrificed and dissected at various time points (30 min, 60 min, 120 min) after injection of radiotracer via the tail vein. Blood is immediately be centrifuged at 15,000 g for 5 min. Liver and kidneys are homogenized and extracted with phosphate buffered saline (PBS) and centrifuged at 15,000 g for 5 min. The extracted organ fractions and a urine sample are separately passed through Sep-Pak $C_{18}$ cartridges (Waters Corp) to collect the radioactive polypeptide tracers. The PET tracers are eluted with 90% acetonitrile containing 0.1% TFA, lyophilized, and resuspended in solvent A. The solution are analyzed by reversed-phase HPLC to determine how much of the tracer is intact post injection and the clearance half-life from different organs.

MicroPET Imaging in Mouse Tumor Models Using Radiolabeled Integrin-Binding Polypeptides To assess the potential of integrin-binding polypeptides as clinical imaging agents, six polypeptides (c(RGDyK) (SEQ ID NO: 140), FN-RDG, FN-RGD, Miniprotein 1.5B, Miniprotein 2.5D, and Miniprotein 2.5F are conjugated to $^{18}$F or $^{64}$Cu. Three polypeptide concentrations are tested, ranging from pmol to nmol. Each imaging study is performed in replicates with three mice.

U87MG glioblastoma xenograft mouse model: All animal procedures are performed in the Stanford Small Animal Imaging Facility, according to protocols approved by the Stanford University Administrative Panels on Laboratory Animal Care. The U87MG glioblastoma cell line (ATCC, Manassas, Va.) is maintained at 37° C. in a humidified atmosphere containing 5% $CO_2$ in Isocove's modified Dulbecco's medium supplemented with 5% heat-inactivated fetal bovine serum (Invitrogen Carlsbad Calif.) and penicillin/streptomycin as an antibiotic. Female athymic nude mice (nu/nu) obtained from Charles River Laboratories, Inc (Cambridge, Mass.) 4 to 6 weeks of age, are subcutaneously injected on the shoulder with $2 \times 10^7$ U87MG glioblastoma cells suspended in 100-uL of phosphate buffered saline. Tumors are allowed to grow to approximately 1 cm for the microPET imaging experiments.

MicroPET imaging: MicroPET imaging of tumor-bearing mice is performed on a microPET R4 rodent model scanner (Concorde Microsystems Inc, Knoxville, Tenn.). U87MG tumor bearing mice are injected with PET imaging agent via the tail vein. At various times post injection, the mice are anesthetized with 2% isoflurane, and 10 min static scans are obtained. Images are reconstructed by a two-dimensional ordered expectation maximum subset algorithm as previously described. Regions of interest (ROI) are drawn over the tumor on decay corrected whole body images and ROI derived % injected dose per gram of tissue is determined. Statistical analysis is performed using the student's t-test for unpaired data. A 95% confidence level is used to determine statistical significance.

Female athymic mice bearing U87MG tumors were injected with 80-150 μCi of $^{64}$Cu-DOTA-knottin 2.5D or 7-9 μCi of [$^{18}$F]-FB-E[knottin 2.5D]. Static images were taken at various timepoints post injection using a microPET R4 rodent model scanner (Concorde Microsystems Inc, Knoxville, Tenn.). Both the $^{64}$Cu- and $^{18}$F-labeled knottin 2.5D clearly targeted the U87MG tumor, with high contrast relative to the contralateral background. Uptake was also observed in the kidney as both probes cleared through the bladder. Probe uptake in the tumor was essentially blocked by preinjection of the unlabeled peptide demonstrating specific targeting of the tumor.

In vivo biodistribution studies: Mice are sacrificed by exanguinations at various time points postinjection. Blood, tumor and the major organs and tissues are collected, wet-weighed and measured in a γ-counter. The % injected dose per gram is determined for each sample. For each mouse, radioactivity of the tissue samples is calibrated against a known aliquot of the injectate. Values are reported as the mean±standard deviation.

The following Table 10 quantifies the $^{64}$Cu-DOTA knottin uptake by direct tissue sampling of the mice up to 24 hours post injection and is reported in % ID (percent injected dose)/gram. Similar results were obtained with [$^{18}$F]-FB-E [knottin 2.5D].

TABLE 10

| | Organ Uptake | | | | |
| --- | --- | --- | --- | --- | --- |
| | Mean | | | | |
| | 0.5 h | 1 h | 2 h | 4 h | 25 h |
| Tumor | 4.94 | 4.47 | 2.89 | 2.24 | 1.31 |
| Liver | 1.39 | 1.29 | 0.98 | 0.92 | 0.53 |
| Kidney | 7.26 | 4.06 | 3.45 | 3.26 | 1.75 |
| Muscle | 0.45 | 0.28 | 0.07 | 0.06 | 0.03 |

The above results compare favorably with imaging done with cyclic RGD.

In previous work, glycosylation or polyethylene glycol modification of the c(RGDyK) (SEQ ID NO: 140) pentapeptide was shown to enhance its pharmacokinetic profiles compared to the unmodified c(RGDyK) (SEQ ID NO: 140) PET tracer. (See, Chen, X., Hou, Y., Tohme, M., Park, R, Khankaldyyan,V., Gonzales-Gomez, I., Bading, J. R, Laug, W. E. & Conti, P. S. (2004). Pegylated Arg-Gly-Asp peptide: $^{64}$Cu labeling and PET imaging of brain tumor alphavbeta3-integrin expression. J Nucl Med 45, 1776-83., and Haubner, R, Wester, H. J., Burkhart, F., Senekowitsch-Schmidtke, R, Weber, W., Goodman, S. L., Kessler, H. & Schwaiger, M. (2001). Glycosylated RGD-containing peptides: tracer for tumor targeting and angiogenesis imaging with improved biokinetics. J Nucl Med 42, 326-36.)

Moreover, [$^{18}$F] Galacto-c(RGDfK) has recently been used in humans for PET-based clinical trials, and its uptake was shown to correlate well with expression αvβ3 in several different human tumors. (See, Beer, A J., Haubner, R, Wolf, I., Goebel, M., Luderschmidt, S., Niemeyer, M., Grosu, A L., Martinez, M. J., Wester, H. J., Weber, W. A & Schwaiger, M. (2006). PET-based human dosimetry of 18F-galacto-RGD, a new radiotracer for imaging alpha v beta3 expression. J Nucl Med 47, 7639., and Haubner, R, Weber, W. A, Beer, A J., Vabuliene, E., Reim, D., Sarbia, M., Becker, K. F., Goebel, M., Hein, R, Wester, H. J., Kessler, H. & Schwaiger, M. (2005). Noninvasive visualization of the activated alpha v beta 3 integrin in cancer patients by positron emission tomography and [18F]Galacto-RGD. PLoS Med 2, e70.) Similar polypeptide modifications can be applied here if PET imaging data indicates poor pharmacokinetics or biodistribution in vivo.

Other Labeling Strategies

Peptides with paramagnetic ions as labels for use in magnetic resonance imaging have also been described (Lauffer, R. B. Magnetic Resonance in Medicine 1991 22:339-342). The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Presence of the label, as compared to imaging of normal tissue, permits determination of the spread of the cancer. The amount of label within an organ or tissue also allows determination of the presence or absence of cancer in that organ or tissue. $^{90}Y$ and $^{177}Lu$ may be used for therapy.

DOTA Chemical Conjugation and $^{64}Cu$ Radiolabeling of Peptides 2.5D and 2.5F

Peptides 2.5D and 2.5F, containing the engineered sequences flanking the RGD integrin binding motif, were radiolabeled, as were controls containing the native fibronectin RGD sequence and a scrambled RGD sequence (RDG instead of RGD).

The radiolabel was coupled at the amino terminus through 1,4,7,10-tetradodecane-N,N',N",N'"-tetraacetic acid (DOTA; Sigma Aldrich) which was activated with 1-ethyl-3-[3-(dimethylamino)propyl]carbodiimide (EDC; Pierce) and N-hydroxysulfonosuccinimide (SNHS; Pierce) in water (pH 5.5) for 40 min at room temperature using a 1:1:1 molar ratio of DOTA:EDC:SNHS. Peptides were dissolved in 300 µL of sodium phosphate buffer (30 mM, pH 8.5), and added to the above in-situ prepared sulfosuccinimidyl ester of DOTA (DOTA-OSSu). A molar excess of DOTA-OSSu was used to drive the conjugation reaction to completion. The reaction was allowed to proceed at room temperature for 1 h and mixed at 4° C. overnight. The resulting DOTA-peptide conjugates were purified by reversed-phase HPLC and stored as a lyophilized solid. The product masses were verified by ESI-MS and MALDI-TOF-MS and peptide concentrations were determined by amino acid analysis.

The DOTA-conjugated peptides (25 µg) were radiolabeled with $^{64}Cu$ by incubating with 2-3 mCi $^{64}CuCl_2$ (University of Wisconsin-Madison, Madison, Wis.) in 0.1 N sodium acetate (pH 6.3) for 1 h at 45° C. The reaction was terminated with the addition of EDTA. The radiolabeled complexes were purified using a PD-10 column (Amersham) or by radio-HPLC using a gamma detector, dried by rotary evaporation, reconstituted in PBS, and passed through a 0.22 µm filter for animal experiments. The radiochemical purity, determined as the ratio of the main product peak to other peaks, was determined by HPLC to be >95%. The radiochemical yield, determined as the ratio of final activity of the product over the starting activity used for the reaction, was usually over 80%. At least 7 radiolabeling reactions were performed for experiments run on different days.

A U87MG glioblastoma xenograft mouse model was used. U87MG cells were maintained at 37° C. in a humidified atmosphere containing 5% $CO_2$ in Dulbecco's modified eagle medium, 10% heat-inactivated fetal bovine serum, and penicillin-streptomycin (all from Invitrogen). Animal procedures were carried out according to a protocol by Stanford University Administrative Panels on Laboratory Animal Care. Female athymic nude mice (nu/nu), obtained at 4-6 weeks of age (Charles River Laboratories, Inc.), were injected subcutaneously in the right or left shoulder with $2\times10^7$ U87MG glioblastoma cells suspended in 100 µL of PBS. Mice were used for in vivo imaging studies when their tumors reached approximately 8 to 10 millimeters in diameter.

U87MG tumor-bearing mice (n=3 or more for each probe) were injected with ~100 µCi of $^{64}Cu$-DOTA-conjugated peptides via the tail vein and imaged with a microPET R4 rodent model scanner (Siemens Medical) using 3 or 5 min static scans. For blocking experiments, mice were co-injected with 330 µg (~0.5 µmol) of unlabeled c(RGDyK) (SEQ ID NO: 140). Images were reconstructed by a two dimensional ordered expectation maximum subset algorithm and calibrated as previously described (Wu, Y, Zhang, X, Xiong, Z, et al. microPET imaging of glioma integrin {alpha}v{beta}3 expression using (64)Cu-labeled tetrameric RGD peptide. J Nucl Med 2005; 46:1707-18). ROIs were drawn over the tumor on decay-corrected whole body images using ASIPro VM software (Siemens Medical). The mean counts per pixel per minute were obtained from the ROI and converted to counts per milliliter per minute with a calibration constant. ROIs were converted to counts/g/min, and % ID/g values were determined assuming a tissue density of 1 g/mL. No attenuation correction was performed.

Knottin peptides 2.5D and 2.5F were shown to bind to U87MG cells with a significantly stronger affinity ($IC_{50}$=19±6 nM and 26±5 nM, respectively) than both the loop-grafted FN-RGD2 ($IC_{50}$=370±150 nM) and c(RGDyK) (SEQ ID NO: 140) ($IC_{50}$=860±400 nM) peptides. FN-RDG2 was not able to compete for $^{125}I$-echistatin binding to U87MG cells, as expected. Next, DOTA-conjugated peptides were shown to bind to U87MG cells in a dose-dependent manner with affinities that were comparable to the unmodified peptides. Since U87MG cells have been shown to express $\alpha_v\beta_5$, and $\alpha_5\beta_1$ integrins in addition to $\alpha_v\beta_3$ integrin, we measured integrin binding specificity by competition of $^{125}I$-echistatin to detergent-solubilized $\alpha_v\beta_3$, $\alpha_v\beta_5$, $\alpha_5\beta_1$, and $\alpha_{iib}\beta_3$ integrin receptors coated onto microtiter plates. Unlabeled echistatin, our positive control, bound strongly to all of the tested integrins, in agreement with previous reports. All RGD-containing peptides bound to $\alpha_v\beta_3$ and $\alpha_v\beta_5$ integrins to some degree, with the knottin peptides 2.5D, and 2.5F showing the strongest levels of binding compared to FN-RGD2 and c(RGDyK (SEQ ID NO: 140). DOTA-conjugated FN-RDG2, our negative control (having the RGD sequence switched to RDG), did not bind to any of the integrins used in this study.

Tumor uptake at 1 h post injection for two high affinity ($IC_{50}$~20 nM) $^{64}Cu$-DOTA-conjugated knottin peptides was 4.47±1.21 and 4.56±0.64% injected dose/gram (% ID/g), compared to a low affinity knottin peptide ($IC_{50}$~0.4 µM; 1.48±0.53% ID/g) and c(RGDyK) (SEQ ID NO: 140) ($IC_{50}$~1 µM; 2.32±0.55% ID/g), a low affinity cyclic pentapeptide under clinical development. Furthermore, $^{64}Cu$-DOTA-conjugated knottin peptides generated lower levels of non-specific liver uptake (~2% ID/g) compared to c(RGDyK) (SEQ ID NO: 140) (~4% ID/g) 1 h post injection. MicroPET imaging results were confirmed by in vivo biodistribution studies. $^{64}Cu$-DOTA-conjugated knottin peptides were stable in mouse serum, and in vivo metabolite analysis showed minimal degradation in the blood or tumor upon injection. Thus, engineered integrin-binding knottin peptides show great potential as clinical diagnostics for a variety of cancers.

The above results showed that Cy5.5-(optical label described above) and $^{64}Cu$-DOTA-conjugated FN-RGD2 knottin peptides, which bind to integrins with affinities in the low micromolar range, generated significantly weaker imaging signals compared to knottin peptides 2.5D and 2.5F. These results strongly suggest that integrin binding affinity influences tumor uptake of knottin peptides, although other factors such as hydrophobicity can also affect tissue biodistribution. Interestingly, in PET studies knottin peptide 2.5F exhibited slower tumor washout compared to 2.5D, resulting in much higher tumor/blood ratios 4 h post injection. This could be due to the ability of knottin 2.5F to bind more tightly to $\alpha_5\beta_1$ integrins compared to knottin 2.5D or potential differences in peptide hydrophobicity, charge, or off-rates of integrin receptor binding. Finally, we demonstrated that knottin peptides were stable in vitro upon prolonged serum incubation, and in vivo in the tumor and blood during the timeframe in which imaging experiments were performed. In addition to increased tumor uptake, high affinity $^{64}$Cu-DOTA-labeled knottin peptides 2.5D and 2.5F demonstrated more favorable tissue distribution as shown by lower liver uptake compared to $^{64}$Cu-DOTA-c(RGDyK). PEGylated versions of the knottin peptides, as well as oligomeric knottin proteins that present multiple integrin-binding RGD motifs may be synthesized according to known methods and used in the imaging application described here. Based on the teachings of the present disclosure, it may be expected that these peptides will elicit enhanced tissue distribution and/or tumor uptake compared to unmodified knottin peptides, much like that observed with PEGylated and multivalent c(RGDyK) (SEQ ID NO: 140) peptides, respectively.

Imaging with Agouti Peptide 7C Labeled with DOTA-$^{64}$Cu

Figure 13:
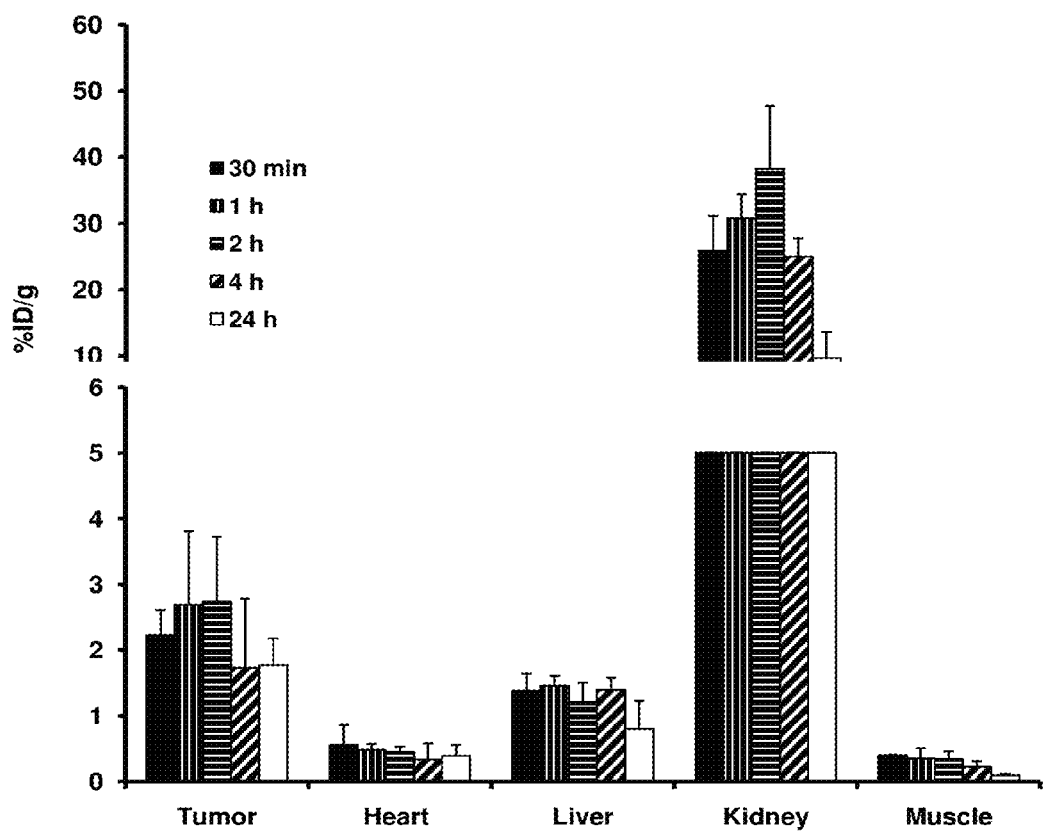
FIG. 13 is a chart showing radioactivity accumulation quantification in selected organs of U87-MG tumor bearing mice at 30 min, 1 hour, 2 hour, 4 hour and 24 hour after injection of $^{64}$Cu-DOTA-7C AgRP engineered peptide.

This example was carried out in similar manner to that above. A $^{64}$Cu Labeled AgRP loop 4 RDG mutant (peptide 7C, described above). It was shown by HPLC radiochromatogram to be essentially pure. Its binding activity was demonstrated with a U87MG cell $^{125}$I-echistatin competition binding assay, as described above. 7C showed better binding than 3F, 6E or 6F. In vitro cell uptake of the $^{64}$Cu labeled 7C on U87-MG cells could be blocked with cRGDyK (SEQ ID NO: 140). Biodistribution studies showed preferential uptake of the labeled 7C by a U87-MG tumor implanted in nude mice. Of non-tumor tissue, the kidneys were shown to have the highest uptake. These data are shown in FIG. 13.

Peptide Formulations

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The pharmaceutical composition may be administered parenterally, topically, orally or locally. It is preferably given by parenteral, e.g., subcutaneous, intradermal or intramuscular route, preferably by subcutaneous or intradermal route, in order to reach proliferating cells in particular (e.g., potential metastases and tumor cells). Within the scope of tumor therapy the peptide may also be administered directly into a tumor.

The composition according to the invention for parenteral administration is generally in the form of a solution or suspension of the peptide in a pharmaceutically acceptable carrier, preferably an aqueous carrier. Examples of aqueous carriers that may be used include water, buffered water, saline solution (0.4%), glycine solution (0.3%), hyaluronic acid and similar known carriers. Apart from aqueous carriers it is also possible to use solvents such as dimethylsulphoxide, propyleneglycol, dimethylformamide and mixtures thereof. The composition may also contain pharmaceutically acceptable excipients such as buffer substances and inorganic salts in order to achieve normal osmotic pressure and/or effective lyophilization. Examples of such additives are sodium and potassium salts, e.g., chlorides and phosphates, sucrose, glucose, protein hydrolysates, dextran, polyvinylpyrrolidone or polyethylene glycol. The compositions may be sterilized by conventional methods, e.g., by sterile filtration. The composition may be decanted directly in this form or lyophilized and mixed with a sterile solution before use.

In one embodiment, the pharmaceutical composition according to the invention is in the form of a topical formulation, e.g., for dermal or transdermal application. The pharmaceutical composition may, for example, take the form of hydrogel based on polyacrylic acid or polyacrylamide (such as Dolobene®, Merckle), as an ointment, e.g., with polyethyleneglycol (PEG) as the carrier, like the standard ointment DAB 8 (50% PEG 300, 50% PEG 1500), or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin, as well as pyrrolidones, e.g., 2-pyrrolidone, N-methyl-2-pyrrolidone, 2-pyrrolidone-5-carboxylic acid or the biodegradable N-(2-hydroxyethyl)-2-pyrrolidone and the fatty acid esters thereof, urea derivatives such as dodecylurea, 1,3-didodecylurea and 1,3-diphenylurea, terpenes, e.g., D-limonene, menthone, a-terpinol, carvol, limonene oxide or 1,8-cineol.

Other formulations are aerosols, e.g., for administering as a nasal spray or for inhalation.

The composition according to the invention may also be administered by means of liposomes which may take the form of emulsions, foams, micelles, insoluble monolayers, phospholipid dispersions, lamella layers and the like. These act as carriers for conveying the peptides to their target of a certain tissue, e.g., lymphoid tissue or tumor tissue or to increase the half-life of the peptides. The present peptides may also be formulated for oral peptide delivery, e.g., with organic acids to inactivate digestive enzymes and a detergent, or bile acid for temporarily opening up the tight junctions within the intestine to facilitate transport into the bloodstream. The present peptides may also be conjugated to carriers such as polyethylene glycol, or modified by glycosylation, or acylation for improvement of circulatory half-life.

If the composition according to the invention is in the form of a topical formulation it may also contain UV-absorbers in order to act, for example, as a sun protection cream, for example, when the formulation is used prophylactically against melanoma.

The person skilled in the art will find suitable formulations and adjuvants in standard works such as "Remington's Pharmaceutical Sciences," 1990.

CONCLUSION

The above specific description is meant to exemplify and illustrate the invention and should not be seen as limiting the scope of the invention, which is defined by the literal and equivalent scope of the appended claims. Any patents or publications mentioned in this specification, including the below cited references are indicative of levels of those skilled in the art to which the patent pertains and are intended to convey details of the invention which may not be explicitly set out but which would be understood by workers in the field Such patents or publications are hereby incorporated by reference to the same extent as if each was specifically and individually incorporated by reference, as needed for the purpose of describing and enabling the methods and materials.

REFERENCES

1. Aota, S., Nomizu, M., Yamada, K. M., "The short amino acid sequence Pro-His-Ser-Arg-Asn in human fibronectin enhances cell-adhesive function," *J Biol Chem*, 1994, 269:24756-61.
2. Archer, G. E., Sampson, J. H., Lorimer, I. A., McLendon, R. E., Kuan, C. T., et al., "Regional treatment of epidermal growth factor receptor vIII-expressing neoplastic meningitis with a single-chain immunotoxin, MR-1," *Clin Cancer Res*, 1999, 5:2646-52.
3. Ashcroft, R. G., Lopez, P. A., "Commercial high-speed machines open new opportunities in high throughput flow cytometry (HTFC)," *J Immunol Methods*, 2000, 243:13-24.
4. Boder, E. T., and Wittrup, K. D., "Yeast surface display for screening combinatorial polypeptide libraries," *Nat Biotechnol*, 1997, 15, 553-7.
5. Beste, G., Schmidt, F. S., Stibora, T., Skerra, A., "Small antibody-like proteins with prescribed ligand specificities derived from the lipocalin fold," *Proc Natl Acad Sci USA*, 1999, 96:1898-903.
6. Biagini, S. C. G., Gibson, S. E., Keen, S. P., "Cross-metathesis of unsaturated a-amino acid derivatives," *J Chem Soc*, 1998, Perkins Trans 1:2485-2499.
7. Blackwell, H. E., Sadowsky, J. D., Howard, R. J., Sampson, J. N., Chao, J. A., et al., "Ring-closing metathesis of olefinic peptides: Design, synthesis, and structural characterization of macrocyclic helical peptides," *J Org Chem*, 2001, 66:5291-5302.
8. Blystone, S. D., Graham, I. L., Lindberg, F. P., Brown, E. J., "Integrin alpha v beta 3 differentially regulates adhesive and phagocytic functions of the fibronectin receptor alpha 5 beta 1," *J Cell Biol*, 1994, 127:1129-37.
9. Boder, E. T., Midelfort, K. S., Wittrup, K. D., "Directed evolution of antibody fragments with monovalent femtomolar antigen-binding affinity," *Proc Natl Acad Sci USA*, 2000, 97:10701-5.
10. Boder, E. T., Wittrup, K. D., "Yeast surface display for screening combinatorial polypeptide libraries," *Nat Biotechnol*, 1997, 15:553-7.
11. Boder, E. T., Wittrup, K. D., "Yeast surface display for directed evolution of protein expression, affinity, and stability," *Methods Enzymol*, 2000, 328:430-44.
12. Bollhagen, R., Schmiedberger, M., Barlos, K., Grell, E., "A new reagent for the cleavage of fully protected peptides synthesized on 2-chlorotrityl chloride resin," *J Chem Soc Chem*, 1994, Comm:2559-60.
13. Brinkley, M. A., "A survey of methods for preparing protein conjugates with dyes, hapten, and cross-linking reagents," *Bioconjugate Chem*, 1992, 3:2-13.
14. Brooks, P. C., Clark, R. A., Cheresh, D. A., "Requirement of vascular integrin alpha v beta 3 for angiogenesis," *Science*, 1994a, 264:569-71.
15. Brooks, P. C., Montgomery, A. M., Rosenfeld, M., Reisfeld, R. A., Hu, T., et al., "Integrin alpha v beta 3 antagonists promote tumor regression by inducing apoptosis of angiogenic blood vessels," *Cell*, 1994b, 79:1157-64.
16. Brooks, P. C., Stromblad, S., Klemke, R., Visscher, D., Sarkar, F. H., Cheresh, D. A., "Antiintegrin alpha v beta 3 blocks human breast cancer growth and angiogenesis in human skin," *J Clin Invest*, 1995, 96:1815-22.
17. Brooks, P. C., Stromblad, S., Sanders, L. C., von Schalscha, T. L., Aimes, R. T., et al., "Localization of matrix metalloproteinase MMP-2 to the surface of invasive cells by interaction with integrin alpha v beta 3," *Cell*, 1996, 85:683-93.
18. Brower, V., "Tumor angiogenesis—new drugs on the block," *Nat Biotechnol*, 1999, 17:963-8.
19. Buerkle, M. A., Pahernik, S. A., Sutter, A., Jonczyk, A., Messmer, K., Dellian, M., "Inhibition of the alpha-nu integrins with a cyclic RGD peptide impairs angiogenesis, growth and metastasis of solid tumours in vivo," *Br J Cancer*, 2002, 86(5), 788-95 86:788-95.
20. Charo, I. F., Nannizzi, L., Phillips, D. R., Hsu, M. A., Scarborough, R. M., "Inhibition of fibrinogen binding to GP IIb-IIIa by a GP IIIa peptide," *J Biol Chem*, 1991, 266:1415-21.
21. Chatterjee, A. K., Morgan, J. P., School, M., Grubbs, R. H., "Synthesis of functionalized olefins by cross and ring-closing metathesis," *J Am Chem Soc*, 2000a, 122:3783-4.
22. Chatterjee, S., Brite, K. H., Matsumura, A., "Induction of apoptosis of integrin-expressing human prostate cancer cells by cyclic Arg-Gly-Asp peptides," *Clin Cancer Res*, 2001, 7:3006-11.
23. Chatterjee, S., Matsumura, A., Schradermeier, J., Gillespie, G. Y., "Human malignant glioma therapy using anti-alpha(v)beta3 integrin agents," *J Neurooncol*, 2000b, 46:135-44.
24. Chen, W., Georgiou, G., "Cell-Surface display of heterologous proteins: From high-throughput screening to environmental applications," *Biotechnol Bioeng*, 2002, 79(5):496-503 79:496-503.
25. Chhabra, S. R., Hothi, B., Evans, D. J., White, P. D., Bycroft, B. W., Chan, W. C., "An appraisal of new variants of Dde amine protecting group for solid phase peptide synthesis," *Tetrahedron Lett*, 1998, 39:1603-1606.
26. Christmann, A., Walter, K., Wentzel, A., Kratzner, R., Kalmar, H., "The cystine knot of a squash-type protease inhibitor as a structural scaffold for *Escherichia coli* cell surface display of conformationally constrained peptides," *Protein Eng*, 1999, 12:797-806.
27. Cochran, A. G., "Antagonists of protein-protein interactions," *Chem Biol*, 2000, 7:R85-R94.
28. Cochran, J. R., Aivazian, D., Cameron, T. O., Stern, L. J., "Receptor clustering and transmembrane signaling in T cells," *Trends Biochem Sci*, 2001a, 26:304-10.
29. Cochran, J. R., Cameron, T. O., Stern, L. J., "The relationship of MHC-peptide binding and T cell activation probed using chemically defined MHC class II oligomers," *Immunity*, 2000, 12:241-50.
30. Cochran, J. R., Cameron, T. O., Stone, J. D., Lubetsky, J. B., Stern, L. J., "Receptor proximity, not intermolecular orientation, is critical for triggering T-cell activation," *J Biol Chem*, 2001b, 276:28068-74.
31. Cochran, J. R., Stern, L. J. 2000. A diverse set of oligomeric class II MHC-peptide complexes for probing T-cell receptor interactions. Chem Biol 7:683-96.

32. Copie, V., Tomita, Y., Akiyama, S. K., Aota, S., Yamada, K. M., et al., "Solution structure and dynamics of linked cell attachment modules of mouse fibronectin containing the RGD and synergy regions: comparison with the human fibronectin crystal structure," *J Mol Biol*, 1998, 277:663-82.

33. Davis, J. H., Bradley, E. K., Miljanich, G. P., Nadasdi, L., Ramachandran, J., Basus, V. J., "Solution structure of omega-conotoxin GVIA using 2-D NMR spectroscopy and relaxation matrix analysis," *Biochemistry*, 1993, 32:7396-405.

34. Desai, N. P., Hubbell, J. A., "Biological responses to polyethylene oxide modified polyethylene terephthalate surfaces," *J Biomed Mater Res*, 1991, 25:829-43.

35. Dickinson, C. D., Veerapandian, B., Dai, X. P., Hamlin, R. C., Xuong, N. H., et al., "Crystal structure of the tenth type III cell adhesion module of human fibronectin," *J Mol Biol*, 1994, 236:1079-92.

36. Dickson, E. F., Pollak, A., Diamandis, E. P., "Ultrasensitive bioanalytical assays using time-resolved fluorescence detection," *Pharmacol Ther*, 1995, 66:207-35.

37. D'Souza, S. E., Ginsberg, M. H., Plow, E. F., "Arginyl-glycyl-aspartic acid (RGD): a cell adhesion motif," *Trends Biochem Sci*, 1991, 16:246-50.

38. D'Souza, S. E., Haas, T. A., Piotrowicz, R. S., Byers-Ward, V., McGrath, D. E., et al., "Ligand and cation binding are dual functions of a discrete segment of the integrin beta 3 subunit: cation displacement is involved in ligand binding," *Cell*, 1994, 79:659-67.

39. Ellgaard, L., Molinari, M., Helenius, A., "Setting the standards: quality control in the secretory pathway," *Science*, 1999, 286:1882-8.

40. Erdreich-Epstein, A., Shimada, H., Groshen, S., Liu, M., Metelitsa, L. S., et al., "Integrins alpha(v)beta3 and alpha (v)beta5 are expressed by endothelium of high-risk neuroblastoma and their inhibition is associated with increased endogenous ceramide," *Cancer Res*, 2000, 60:712-21.

41. Feldhaus, M. J., Siegel, R. W., Opresko, L. K., Coleman, J. R., Feldhaus, J. M., et al., "Flow-cytometric isolation of human antibodies from a nonimmune *Saccharomyces cerevisiae* surface display library," *Nat Biotechnol*, 2003.

42. Folkman, J., "The role of angiogenesis in tumor growth," *Semin Cancer Biol*, 1992, 3:65-71.

43. Folkman, J., Shing, Y., "Angiogenesis," *J Biol Chem*, 1992, 267:10931-4.

44. Friedlander, M., Brooks, P. C., Shaffer, R. W., Kincaid, C. M., Varner, J. A., Cheresh, D. A., "Definition of two angiogenic pathways by distinct alpha v integrins," *Science*, 1995, 270:1500-2.

45. Gottschalk, K. E., Kessler, H., "The structures of integrins and integrin-ligand complexes: implications for drug design and signal transduction," *Angew Chem Int Ed Engl*, 2002, 41:3767-74.

46. Gutheil, J. C., Campbell, T. N., Pierce, P. R., Watkins, J. D., Huse, W. D., et al., "Targeted antiangiogenic therapy for cancer using Vitaxin: a humanized monoclonal antibody to the integrin alphavbeta3," *Clin Can Res*, 2000, 6:3056-61.

47. Haubner, R., Finsinger, D., Kessler, H., "Stereoisomeric peptide libraries and peptidomimetics for designing selective inhibitors of the avb3 integrin for a new cancer therapy," *Angew Chem Int Ed*, 1997, 36:1374-89.

48. Haubner, R., Wester, H. J., Burkhart, F., Senekowitsch-Schmidtke, R., Weber, W., et al., "Glycosylated RGD-containing peptides: tracer for tumor targeting and angiogenesis imaging with improved biokinetics," *J Nucl Med*, 2001a, 42:326-36.

49. Haubner, R., Wester, H. J., Reuning, U., Senekowitsch-Schmidtke, R., Diefenbach, B., et al., "Radiolabeled alpha (v)beta3 integrin antagonists: a new class of tracers for tumor targeting," *J Nucl Med*, 1999, 40:1061-71.

50. Haubner, R., Wester, H. J., Weber, W. A., Mang, C., Ziegler, S. I., et al., "Noninvasive imaging of alpha(v) beta3 integrin expression using 18F-labeled RGD-containing glycopeptide and positron emission tomography," *Cancer Res*, 2001b, 61:1781-5.

51. Hautanen, A., Gailit, J., Mann, D. M., Ruoslahti, E., "Effects of modifications of the RGD sequence and its context on recognition by the fibronectin receptor," *J Biol Chem*, 1989, 264:1437-42.

52. Healy, J. M., Murayama, O., Maeda, T., Yoshino, K., Sekiguchi, K., Kikuchi, M., "Peptide ligands for integrin alpha v beta 3 selected from random phage display libraries," *Biochemistry*, 1995, 34:3948-55.

53. Hermanson, G. T., "Bioconjugate Techniques," *San Diego: Academic Press*, 1996, 785.

54. Hoess, R. H., "Protein design and phage display," *Chem Rev*, 2001, 101:3205-18.

55. Holak, T. A., Bode, W., Huber, R., Otlewski, J., Wilusz, T., "Nuclear magnetic resonance solution and X-ray structures of squash trypsin inhibitor exhibit the same conformation of the proteinase binding loop," *J Mal Biol*, 1989, 210:649-54.

56. Holler, P. D., Holman, P. O., Shusta, E. V., O'Herrin, S., Wittrup, K. D., Kranz, D. M, "In vitro evolution of a T cell receptor with high affinity for peptide/MHC," *Proc Natl Acad Sci USA*, 2000, 97:5387-92.

57. Hufton, S. E., van Neer, N., van den Beuken, T., Desmet, J., Sablon, E., Hoogenboom, H. R., "Development and application of cytotoxic T lymphocyte-associated antigen 4 as a protein scaffold for the generation of novel binding ligands," *FEBS Lett*, 2000, 475:225-31.

58. Hynes, R. O., "Integrins: versatility, modulation, and signaling in cell adhesion," *Cell*, 1992, 69:11-25.

59. Johnson, E. M., Berk, D. A., Jain, R. K., Deen, W. M., "Hindered diffusion in agarose gels: test of effective medium model," *Biophys J*, 1996, 79:3350-3.

60. Johnson, J., W. C., Pagano, T. G., Basson, C. T., Madri, J. A., Gooley, P., Armitage, I. M., "Biologically active Arg-Gly-Asp oligopeptides assume a type II beta-turn in solution," *Biochemistry*, 1993, 32:268-73.

61. Kieke, M. C., Sundberg, E., Shusta, E. V., Mariuzza, R. A., Wittrup, K. D., Kranz, D. M., "High affinity T cell receptors from yeast display libraries block T cell activation by superantigens," *J Mol Biol*, 2001, 307:1305-15.

62. Kim, S., Bell, K., Mousa, S. A., Varner, J. A., "Regulation of angiogenesis in vivo by ligation of integrin alpha5beta1 with the central cell-binding domain of fibronectin," *Am J Pathol*, 2000, 156:1345-62.

63. Koide, A., Bailey, C. W., Huang, X., Koide, S., "The fibronectin type III domain as a scaffold for novel binding proteins," *J. Mol Biol*, 1998, 284:1141-51.

64. Koivunen, E., Gay, D. A., Ruoslahti, E., "Selection of peptides binding to the alpha 5 beta 1 integrin from phage display library," *J Biol Chem*, 1993, 268:20205-10.

65. Koivunen, E., Wang, B., Ruoslahti, E., "Isolation of a highly specific ligand for the alpha 5 beta 1 integrin from a phage display library," *J Cell Biol*, 1994, 124:373-80.

66. Koivunen, E., Wang, B., Ruoslahti, E., "Phage libraries displaying cyclic peptides with different ring sizes: ligand specificities of the RGD-directed integrins," *Biotechnology* (NY), 1995, 13:265-70.
67. Komazawa, H., Saiki, I., Aoki, M., Kitaguchi, H., Satoh, H., et al., "Synthetic Arg-Gly-Asp-Ser analogues of the cell recognition site of fibronectin that retain antimetastatic and anti-cell adhesive properties," *Biol Pharm Bull*, 1993, 16:997-1003.
68. Kraulis, J., Clore, G. M., Nilges, M., Jones, T. A., Pettersson, G., et al., "Determination of the three-dimensional solution structure of the C-terminal domain of cellobiohydrolase I from *Trichoderma reesei*. A study using nuclear magnetic resonance and hybrid distance geometry-dynamical simulated annealing," *Biochemistry*, 1989, 28:7241-57.
69. Krezel, A. M., Wagner, G., Seymour-Ulmer, J., Lazarus, R. A., "Structure of the RGD protein decorsin: conserved motif and distinct function in leech proteins that affect blood clotting," *Science*, 1994, 264:1944-7.
70. Kuan, C. T., Wikstrand, C. J., Bigner, D. D., "EGFRvIII as a promising target for antibody-based brain tumor therapy," *Brain Tumor Pathol*, 2000, 17:71-8.
71. Leahy, D. J., Aukhil, I., Erickson, H. P., "2.0 A crystal structure of a four-domain segment of human fibronectin encompassing the RGD loop and synergy region," *Cell*, 1996, 84:155-64.
72. Li, R., Hoess, R. H., Bennett, J. S., DeGrado, W. F., "Use of phage display to probe the evolution of binding specificity and affinity in integrins," *Protein Engineering In Press*, 2003.
73. Luscinskas, F. W., Lawler, J., "Integrins as dynamic regulators of vascular function," *FASEB J*, 1994, 8:929-38. Maheshwari, G., Brown, G., Lauffenburger, D. A., Wells, A., Griffith, L. G., "Cell adhesion and motility depend on nanoscale RGD clustering," *J Cell Sci*, 2000, 113:1677-86.
74. Maynard, H. D., Okada, S. Y., Grubbs, R. H., "Inhibition of cell adhesion to fibronectin by oligopeptide substituted polynorbornenes," *J Am Chem Soc*, 2001, 123:1275-9.
75. Maynard, J., Georgiou, G., "Antibody engineering," *Annu Rev Biomed Eng*, 2000, 2:339-76.
76. McConnell, S. J., Hoess, R. H., "Tendamistat as a scaffold for conformationally constrained phage peptide libraries," *J Mol Biol*, 1995, 250:460-70.
77. Mehta, R. J., Diefenbach, B., Brown, A., Cullen, E., Jonczyk, A., et al., "Transmembrane-truncated alphav-beta3 integrin retains high affinity for ligand binding: evidence for an 'inside-out' suppressor?" *Biochem.*, 1998, 1330:861-9.
78. Meilhoc, E., Masson, J. M., Teissie, J., "High efficiency transformation of intact yeast cells by electric field pulses," *Biotechnology*, 1990, 8:223-7.
79. Miyamoto, S., Akiyama, S. K., Yamada, K. M., "Synergistic roles for receptor occupancy and aggregation in integrin transmembrane function," *Science*, 1995, 267:883-5.
80. Obara, M., Yoshizato, K., "Possible involvement of the interaction of the alpha 5 subunit of alpha 5 beta 1 integrin with the synergistic region of the central cell-binding domain of fibronectin in cells to fibronectin binding," *Exp Cell Res*, 1995, 216:273-6.
81. Pallaghy, P. K., Nielsen, K. J., Craik, D. J., Norton, R. S., "A common structural motif incorporating a cystine knot and a triple-stranded beta-sheet in toxic and inhibitory polypeptides," *Protein Sci*, 1994, 3:1833-9.
82. Pasqualini, R., Koivunen, E., Kain, R., Landenranta, J., Sakamoto, M., et al., "Aminopeptidase N is a receptor for tumor-homing peptides and a target for inhibiting angiogenesis," *Cancer Res*, 2000, 60:722-7.
83. Pasqualini, R., Koivunen, E., Ruoslahti, E., "A peptide isolated from phage display libraries is a structural and functional mimic of an RGD-binding site on integrins," *J Cell Biol*, 1995, 130:1189-96.
84. Pasqualini, R., Koivunen, E., Ruoslahti, E., "Alpha v integrins as receptors for tumor targeting by circulating ligands," *Nat Biotechnol*, 1997, 15:542-6.
85. Pierschbacher, M. D., Polarek, J. W., Craig, W. S., Tschopp, J. F., Sipes, N. J., Harper, J. R., "Manipulation of cellular interactions with biomaterials toward a therapeutic outcome: a perspective," *J Cell Biochem*, 1994, 56:150-4.
86. Pierschbacher, M. D., Ruoslahti, E., "Cell attachment activity of fibronectin can be duplicated by small synthetic fragments of the molecule," *Nature*, 1984, 309:30-3.
87. Polverino de Laureto, P., Scaramella, E., De Filippis, V., Marin, O., Doni, M. G., Fontana, A., "Chemical synthesis and structural characterization of the RGD-protein decorsin: a potent inhibitor of platelet aggregation," *Protein Sci*, 1998, 7:433-44.
88. Pytela, R., Pierschbacher, M. D., Argraves, S., Suzuki, S., Ruoslahti, E., "Arginine-glycine-aspartic acid adhesion receptors," *Methods Enzymol*, 1987, 144:475-89.
89. Raymond, C. K., Pownder, T. A., Sexson, S. L., "General method for plasmid construction using homologous recombination," *BioTechniques*, 1999, 26:134-41.
90. Ruoslahti, E. 1996. RGD and other recognition sequences for integrins. Annu Rev Cell Dev Biol 12:697-715. Ruoslahti, E., "Targeting tumor vasculature with homing peptides from phage display," *Semin Cancer Biol*, 2000, 10:435-42.
91. Saiki, 1., "Cell adhesion molecules and cancer metastasis," *Jpn Jpharmacol*, 1997, 75:215-42.
92. Saudek, V., Atkinson, R. A., Pelton, J. T., "Three-dimensional structure of echistatin, the smallest active RGD protein," *Biochemistry*, 1991, 30:7369-72.
93. Sblattero, D., Bradbury, A., "A definitive set of oligonucleotide primers for amplifying human V regions," *Immunotechnology*, 1998, 3:271-8.
94. Schier, R., Bye, J., Apell, G., McCall, A., Adams, G. P., et al., "Isolation of high-affinity monomeric human anti-c-erbB-2 single chain Fv using affinity-driven selection," *J Mol Biol*, 1996, 255:28-43.
95. Shakesheff, K., Cannizzaro, S., Langer, R., "Creating biomimetic micro-environments with synthetic polymer-peptide hybrid molecules," *J Biomater Sci Polym Ed*, 1998, 9:507-18.
96. Sheets, M. D., Amersdorfer, P., Finnern, R., Sargent, P., Lindquist, E., et al., "Efficient construction of a large nonimmune phage antibody library: the production of high-affinity human single-chain antibodies to protein antigens," *Proc Natl Acad Sci*, 1998, 95:6157-62.
97. Shiraishi, K., Ohnishi, T., Sugiyama, K., "Preparation of poly(methyl methacrylate) microspheres modified with amino acid moieties," *Macromol Chem Phys*, 1998, 199:2023-2028.
98. Shusta, E. V., Holler, P. D., Kieke, M. C., Kranz, D. M., Wittrup, K. D., "Directed evolution of a stable scaffold for T-cell receptor engineering," *Nat Biotechnol*, 2000, 18:754-9.

99. Sidhu, S. S., Lowman, H. B., Cunningham, B. C., Wells, J. A., "Phage display for selection of novel binding peptides," *Methods Enzymol*, 2000, 328:333-63.
100. Sipkins, D. A., Cheresh, D. A., Kazemi, M. R., Nevin, L. M., Bednarski, M. D., Li, K. C., "Detection of tumor angiogenesis in vivo by alphaVbeta3-targeted magnetic resonance imaging," *Nat Med*, 1998, 4:623-6.
101. Smith, G. P., Patel, S. U., Windass, J. D., Thornton, J. M., Winter, G., Griffiths, A. D., "Small binding proteins selected from a combinatorial repertoire of knottins displayed on phage," *J Mol Biol*, 1998, 277:317-32.
102. Trnka, T. M., Grubbs, R. H., "The development of L2X2Ru=CHR olefin metathesis catalysts: an organometallic success story," *Acc Chem Res*, 2001, 34:18-29.
103. Ulrich, H. D., Patten, P. A., Yang, P. L., Romesberg, F. E., Schultz, P. G., "Expression studies of catalytic antibodies," *Proc Nail Acad Sci*, 1995, 92:11907-11.
104. van Hagen, P. M., Breeman, W. A., Bernard, H. F., Schaar, M., Mooij, C. M., et al., "Evaluation of a radiolabelled cyclic DTPA-RGD analogue for tumour imaging and radionuclide therapy," *Int J Cancer*, 2000, 90:186-98.
105. VanAntwerp, J. J., Wittrup, K. D., "Fine affinity discrimination by yeast surface display and flow cytometry," *Biotechnol Prog*, 2000, 16:31-7.
106. Welschof, M., Krauss, J., eds., "Recombinant antibodies for cancer therapy," Totowa, N.J.: Humana Press, 2003, Vol. 207.
107. Wentzel, A., Christmann, A., Kratzner, R., Kolmar, H., "Sequence requirements of the GPNG beta-turn of the *Ecballium elaterium* trypsin inhibitor II explored by combinatorial library screening," *J Biol Chem*, 1999, 274: 21037-43.
108. Wittrup, K. D., "Phage on display," *Trends Biotechnol*, 1999, 17:423-4.
109. Xiong, J. P., Stehle, T., Diefenbach, B., Zhang, R., Dunker, R., et al., "Crystal structure of the extracellular segment of integrin alpha Vbeta3," *Science*, 2001, 294: 339-45.
110. Xiong, J. P., Stehle, T., Zhang, R., Joachimiak, A., Frech, M., et al., "Crystal structure of the extracellular segment of integrin alpha Vbeta3 in complex with an Arg-Gly-Asp ligand," *Science*, 2002, 296:151-5.
111. Zaccolo, M., Williams, D. M., Brown, D. M., Gherardi, E., "An approach to random mutagenesis of DNA using mixtures of triphosphate derivatives of nucleoside analogues," *J Mol Biol*, 1996, 255:589-603.

What is claimed is:

1. A pharmaceutical composition, comprising:
an integrin binding peptide comprising a knottin protein scaffold comprising an engineered integrin binding loop that binds to at least one of αvβ5 integrin, αvβ3 integrin and α5β1 integrin, wherein the integrin binding peptide comprises an amino acid sequence at least 90% identical to the amino acid sequence of a peptide of any one of SEQ ID NO:23 through SEQ ID NO:52; and
a pharmaceutically acceptable carrier.

2. The pharmaceutical composition of claim 1, wherein the integrin binding peptide comprises an amino acid sequence at least 95% identical to the amino acid sequence of a peptide of any one of SEQ ID NO:23 through SEQ ID NO:52.

3. The pharmaceutical composition of claim 1, wherein the integrin binding peptide comprises the amino acid sequence of a peptide of any one of SEQ ID NO:23 through SEQ ID NO:52.

4. The pharmaceutical composition of claim 1, wherein the integrin binding peptide comprises the amino acid sequence of the peptide of SEQ ID NO:49.

5. The pharmaceutical composition of claim 1, wherein the integrin binding peptide comprises the amino acid sequence of the peptide of SEQ ID NO:50.

6. The pharmaceutical composition of claim 1, wherein the integrin binding peptide has a Kd of not more than 100 nM.

7. The pharmaceutical composition of claim 1, wherein the integrin binding peptide binds to two or more of αvβ5 integrin, αvβ3 integrin and α5β1 integrin.

8. The pharmaceutical composition of claim 1, wherein the integrin binding peptide is conjugated to a chemotherapeutic agent.

9. The pharmaceutical composition of claim 1, wherein the integrin binding peptide is conjugated to a half-life extending moiety.

10. The pharmaceutical composition of claim 1, wherein the composition is suitable for parenteral, oral, topical, or local administration to a subject.

11. A pharmaceutical composition, comprising:
a peptide that binds to at least one of αvβ5 integrin, αvβ3 integrin and α5β1 integrin, the peptide comprising a scaffold portion as set forth in SEQ ID NO: 19 and a binding loop portion, wherein, in the binding loop portion:
X1 is selected from the group consisting of A, V, L, P, F, Y, S, H, D, and N;
X2 is selected from the group consisting of G, V, L, P, R, E, and Q;
X3 is selected from the group consisting of G, A, and P;
X7 is selected from the group consisting of W and N;
X8 is selected from the group consisting of A, P, and S;
X9 is selected from the group consisting of P and R;
X10 is selected from the group consisting of A, V, L, P, S, T, and E; and
X11 is selected from the group consisting of G, A, W, S, T, K, and E, and
a pharmaceutically acceptable carrier.

12. The pharmaceutical composition of claim 11, wherein, in the binding loop portion:
X1 is P;
X2 is Q or R;
X3 is G or P;
X7 is W or N;
X8 is A or P;
X9 is P;
X10 is T or L; and
X11 is S or T.

13. The pharmaceutical composition of claim 11, wherein, in the binding loop portion:
X1 is P;
X2 is Q;
X3 is G;
X7 is W;
X8 is A;
X9 is P;
X10 is T; and
X11 is S.

14. The pharmaceutical composition of claim 11, wherein, in the binding loop portion:
X1 is P;
X2 is R;
X3 is P;
X7 is N;
X8 is P;
X9 is P;
X10 is L; and
X11 is T.

15. The pharmaceutical composition of claim 11, wherein the integrin binding peptide has a Kd of not more than 100 nM.

16. The pharmaceutical composition of claim 11, wherein the integrin binding peptide binds to two or more of $\alpha v\beta 5$ integrin, $\alpha v\beta 3$ integrin and $\alpha 5\beta 1$ integrin.

17. The pharmaceutical composition of claim 11, wherein the integrin binding peptide is conjugated to a chemotherapeutic agent or a half-life extending moiety.

18. The pharmaceutical composition of claim 11, wherein the composition is suitable for parenteral, oral, topical, or local administration to a subject.

* * * * *

```
SEQUENCE LISTING

<160> NUMBER OF SEQ ID NOS: 140

<210> SEQ ID NO 1
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 1

Cys Arg Gly Asp Cys Leu
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 2

Ala Cys Arg Gly Asp Gly Trp Cys Gly
1               5

<210> SEQ ID NO 3
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 3

Ala Cys Asp Cys Arg Gly Asp Cys Phe Cys Gly
1               5                   10

<210> SEQ ID NO 4
<211> LENGTH: 9
<212> TYPE: PRT
<213> ORGANISM: Artificial sequence
<220> FEATURE:
<223> OTHER INFORMATION: Synthetic polypeptide
```

```
<400> SEQUENCE: 4

Cys Arg Arg Glu Thr Ala Trp Ala Cys
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Asn Gly Arg Ala His Ala
1               5

<210> SEQ ID NO 6
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 6

Pro His Ser Arg Asn
1               5

<210> SEQ ID NO 7
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 7

Ala Cys Gly Ser Ala Gly Thr Cys Ser Pro His Leu Arg Arg Pro
1               5                   10                  15

<210> SEQ ID NO 8
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 8

Gly Arg Gly Asp
1

<210> SEQ ID NO 9
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 9

Cys Asp Cys Arg Gly Asp Cys Phe Cys
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MISC_FEATURE
<222> LOCATION: (4)..(4)
<223> OTHER INFORMATION: This amino acid may be D-Phe.

<400> SEQUENCE: 10

Arg Gly Asp Phe Val
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 11

Cys Arg Arg Glu Thr Ala Trp Ala Cys
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 12

Cys Asp Cys Arg Gly Asp Cys Phe Cys
1               5

<210> SEQ ID NO 13
<211> LENGTH: 28
<212> TYPE: PRT
<213> ORGANISM: Ecballium elaterium

<400> SEQUENCE: 13

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 14
<211> LENGTH: 47
<212> TYPE: PRT
<213> ORGANISM: Homo sapiens

<400> SEQUENCE: 14

Gly Cys Val Arg Leu His Glu Ser Cys Leu Gly Gln Gln Val Pro Cys
1               5                   10                  15

Cys Asp Pro Cys Ala Thr Cys Tyr Cys Arg Phe Phe Asn Ala Phe Cys
            20                  25                  30

Tyr Cys Arg Lys Leu Gly Thr Ala Met Asn Pro Cys Ser Arg Thr
        35                  40                  45

<210> SEQ ID NO 15
<211> LENGTH: 35
<212> TYPE: PRT
<213> ORGANISM: Artificial sequence
<220> FEATURE:
<223> OTHER INFORMATION: Synthetic polypeptide
```

```
<400> SEQUENCE: 15

Gly Cys Val Arg Leu His Glu Ser Cys Leu Gly Gln Gln Val Pro Cys
1               5                   10                  15

Cys Asp Pro Ala Ala Thr Cys Tyr Cys Arg Phe Phe Asn Ala Phe Cys
                20                  25                  30

Tyr Cys Arg
        35

<210> SEQ ID NO 16
<211> LENGTH: 48
<212> TYPE: PRT
<213> ORGANISM: Agelenopsis aperta

<400> SEQUENCE: 16

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
                20                  25                  30

Asn Cys Glu Cys Thr Pro Arg Leu Ile Met Glu Gly Leu Ser Phe Ala
            35                  40                  45

<210> SEQ ID NO 17
<211> LENGTH: 6
<212> TYPE: DNA
<213> ORGANISM: Artificial sequence
<220> FEATURE:
<223> OTHER INFORMATION: Synthetic nucleic acid

<400> SEQUENCE: 17 gctagc                                                          6

<210> SEQ ID NO 18
<211> LENGTH: 6
<212> TYPE: DNA
<213> ORGANISM: Artificial sequence
<220> FEATURE:
<223> OTHER INFORMATION: Synthetic nucleic acid

<400> SEQUENCE: 18 ggatcc                                                          6

<210> SEQ ID NO 19
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(5)
<223> OTHER INFORMATION: Xaa may be any amino acid.
<220> FEATURE:
<221> NAME/KEY: MISC_FEATURE
<222> LOCATION: (9)..(13)
<223> OTHER INFORMATION: Xaa may be any amino acid.

<400> SEQUENCE: 19

Gly Cys Xaa Xaa Xaa Arg Gly Asp Xaa Xaa Xaa Xaa Xaa Cys Lys Gln
1               5                   10                  15

Asp Ser Asp Cys Leu Ala Gly Cys Val Cys Gly Pro Asn Gly Phe Cys
                20                  25                  30

Gly
```

```
<210> SEQ ID NO 20
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 20

Gly Cys Thr Gly Arg Gly Asp Ser Pro Ala Ser Ser Lys Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 21
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 21

Gly Cys Val Thr Gly Arg Gly Asp Ser Pro Ala Ser Ser Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 22
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(5)
<223> OTHER INFORMATION: Xaa may be any amino acid.
<220> FEATURE:
<221> NAME/KEY: MISC_FEATURE
<222> LOCATION: (9)..(13)
<223> OTHER INFORMATION: Xaa may be any amino acid.

<400> SEQUENCE: 22

Gly Cys Xaa Xaa Xaa Arg Gly Asp Xaa Xaa Xaa Xaa Xaa Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 23
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 23

Gly Cys Ala Glu Pro Arg Gly Asp Met Pro Trp Thr Trp Cys Lys Gln
1               5                   10                  15

Asp Ser Asp Cys Leu Ala Gly Cys Val Cys Gly Pro Asn Gly Phe Cys
            20                  25                  30

Gly
```

-continued

```
<210> SEQ ID NO 24
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 24

Gly Cys Val Gly Gly Arg Gly Asp Trp Ser Pro Lys Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 25
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 25

Gly Cys Ala Glu Leu Arg Gly Asp Arg Ser Tyr Pro Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 26
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 26

Gly Cys Arg Leu Pro Arg Gly Asp Val Pro Arg Pro His Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 27
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 27

Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 28
<211> LENGTH: 33
<212> TYPE: PRT
<213> ORGANISM: Artificial sequence
<220> FEATURE:
<223> OTHER INFORMATION: Synthetic polypeptide
```

```
<400> SEQUENCE: 28

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 29
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 29

Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 30
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 30

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 31
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 31

Gly Cys Leu Pro Pro Arg Gly Asp Asn Pro Pro Ser Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 32
<211> LENGTH: 33
<212> TYPE: PRT
<213> ORGANISM: Artificial sequence
<220> FEATURE:
<223> OTHER INFORMATION: Synthetic polypeptide
```

-continued

<400> SEQUENCE: 32

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 33
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 33

Gly Cys Asn Val Gly Arg Gly Asp Trp Ala Pro Ser Glu Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 34
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 34

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 35
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 35

Gly Cys Pro Leu Pro Arg Gly Asp Asn Pro Pro Thr Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 36
<211> LENGTH: 33
<212> TYPE: PRT
<213> ORGANISM: Artificial sequence
<220> FEATURE:
<223> OTHER INFORMATION: Synthetic polypeptide

```
<400> SEQUENCE: 36

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 37
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 37

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 38
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 38

Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 39
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 39

Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 40
<211> LENGTH: 33
<212> TYPE: PRT
<213> ORGANISM: Artificial sequence
<220> FEATURE:
<223> OTHER INFORMATION: Synthetic polypeptide
```

```
<400> SEQUENCE: 40

Gly Cys Leu Gly Gly Arg Gly Asp Trp Ala Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 41
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 41

Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 42
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 42

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 43
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 43

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 44
<211> LENGTH: 33
<212> TYPE: PRT
<213> ORGANISM: Artificial sequence
<220> FEATURE:
<223> OTHER INFORMATION: Synthetic polypeptide
```

```
<400> SEQUENCE: 44

Gly Cys Tyr Gln Gly Arg Gly Asp Trp Ser Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 45
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 45

Gly Cys Ala Pro Gly Arg Gly Asp Trp Ala Pro Ser Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 46
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 46

Gly Cys Val Gln Gly Arg Gly Asp Trp Ser Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 47
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 47

Gly Cys His Val Gly Arg Gly Asp Trp Ala Pro Glu Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 48
<211> LENGTH: 33
<212> TYPE: PRT
<213> ORGANISM: Artificial sequence
<220> FEATURE:
<223> OTHER INFORMATION: Synthetic polypeptide
```

<400> SEQUENCE: 48

Gly Cys Asp Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 49
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 49

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 50
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 50

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 51
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 51

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 52
<211> LENGTH: 33
<212> TYPE: PRT
<213> ORGANISM: Artificial sequence
<220> FEATURE:
<223> OTHER INFORMATION: Synthetic polypeptide -continued

```
<400> SEQUENCE: 52

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 53
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Xaa may be any amino acid.

<400> SEQUENCE: 53

Gly Cys Pro Xaa Gly Arg Gly Asp Trp Ala Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 54
<211> LENGTH: 44
<212> TYPE: PRT
<213> ORGANISM: Artificial sequence
<220> FEATURE:
<223> OTHER INFORMATION: Synthetic polypeptide

<400> SEQUENCE: 54

Gly Cys Val Arg Leu His Glu Ser Cys Leu Gly Gln Gln Val Pro Cys
1               5                   10                  15

Cys Asp Pro Cys Ala Thr Cys Tyr Cys Arg Gly Asp Cys Tyr Cys Arg
            20                  25                  30

Lys Leu Gly Thr Ala Met Asn Pro Cys Ser Arg Thr
            35                  40

<210> SEQ ID NO 55
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 55

Gly Cys Val Arg Leu His Glu Ser Cys Leu Gly Gln Gln Val Pro Cys
1               5                   10                  15

Cys Asp Pro Cys Ala Thr Cys Tyr Cys Thr Gly Arg Gly Asp Ser Cys
            20                  25                  30

Tyr Cys Arg Lys Leu Gly Thr Ala Met Asn Pro Cys Ser Arg Thr
            35                  40                  45

<210> SEQ ID NO 56
<211> LENGTH: 49
<212> TYPE: PRT
<213> ORGANISM: Artificial sequence
<220> FEATURE:
<223> OTHER INFORMATION: Synthetic polypeptide
```

```
<400> SEQUENCE: 56

Cys Val Arg Leu His Glu Ser Cys Leu Gly Gln Gln Val Pro Cys Cys
1               5                   10                  15

Asp Pro Cys Ala Thr Cys Tyr Cys Thr Gly Arg Gly Asp Ser Pro Ala
                20                  25                  30

Ser Cys Tyr Cys Arg Lys Leu Gly Thr Ala Met Asn Pro Cys Ser Arg
            35                  40                  45

Thr

<210> SEQ ID NO 57
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 57

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Ser Pro
                20                  25                  30

Ala Ser Cys Tyr Cys Arg
            35

<210> SEQ ID NO 58
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 58

Gly Cys Ile Ala Glu Asp Tyr Gly Lys Cys Thr Trp Gly Gly Thr Lys
1               5                   10                  15

Cys Cys Arg Gly Arg Pro Cys Arg Cys Thr Gly Arg Gly Asp Ser Pro
                20                  25                  30

Ala Ser Cys Glu Cys Thr
            35

<210> SEQ ID NO 59
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (26)..(27)
<223> OTHER INFORMATION: Xaa may be any amino acid.
<220> FEATURE:
<221> NAME/KEY: MISC_FEATURE
<222> LOCATION: (31)..(34)
<223> OTHER INFORMATION: Xaa may be any amino acid.

<400> SEQUENCE: 59

Gly Cys Val Arg Leu His Glu Ser Cys Leu Gly Gln Gln Val Pro Cys
1               5                   10                  15

Cys Asp Pro Ala Ala Thr Cys Tyr Cys Xaa Xaa Arg Gly Asp Xaa Xaa
                20                  25                  30

Xaa Xaa Cys Tyr Cys Arg
            35
```

```
<210> SEQ ID NO 60
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 60

Gly Cys Val Arg Leu His Glu Ser Cys Leu Gly Gln Gln Val Pro Cys
1               5                   10                  15

Cys Asp Pro Ala Ala Thr Cys Tyr Cys Val Val Arg Gly Asp Trp Arg
            20                  25                  30

Lys Arg Cys Tyr Cys Arg
        35

<210> SEQ ID NO 61
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 61

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Met Leu
            20                  25                  30

Glu Lys Cys Tyr Cys Arg
        35

<210> SEQ ID NO 62
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 62

Gly Cys Val Arg Leu His Glu Ser Cys Leu Gly Gln Gln Val Pro Cys
1               5                   10                  15

Cys Asp Pro Ala Ala Thr Cys Tyr Cys Glu Thr Arg Gly Asp Gly Lys
            20                  25                  30

Glu Lys Cys Tyr Cys Arg
        35

<210> SEQ ID NO 63
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 63

Gly Cys Val Arg Leu His Glu Ser Cys Leu Gly Gln Gln Val Pro Cys
1               5                   10                  15

Cys Asp Pro Ala Ala Thr Cys Tyr Cys Gln Trp Arg Gly Asp Gly Asp
            20                  25                  30

Val Lys Cys Tyr Cys Arg
        35
```

```
<210> SEQ ID NO 64
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 64

Gly Cys Val Arg Leu His Glu Ser Cys Leu Gly Gln Gln Val Pro Cys
1               5                   10                  15

Cys Asp Pro Ala Ala Thr Cys Tyr Cys Ser Arg Arg Gly Asp Met Arg
            20                  25                  30

Glu Arg Cys Tyr Cys Arg
        35

<210> SEQ ID NO 65
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 65

Gly Cys Val Arg Leu His Glu Ser Cys Leu Gly Gln Gln Val Pro Cys
1               5                   10                  15

Cys Asp Pro Ala Ala Thr Cys Tyr Cys Gln Tyr Arg Gly Asp Gly Met
            20                  25                  30

Lys His Cys Tyr Cys Arg
        35

<210> SEQ ID NO 66
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 66

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Thr Lys
            20                  25                  30

Val Leu Cys Tyr Cys Arg
        35

<210> SEQ ID NO 67
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 67

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Met Lys
            20                  25                  30

Arg Arg Cys Tyr Cys Arg
        35
```

```
<210> SEQ ID NO 68
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 68

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Val Arg
            20                  25                  30

Met Asn Cys Tyr Cys Arg
        35

<210> SEQ ID NO 69
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 69

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Ser Lys Cys Tyr Cys Arg
        35

<210> SEQ ID NO 70
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 70

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Met Arg
            20                  25                  30

Arg Glu Cys Tyr Cys Arg
        35

<210> SEQ ID NO 71
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 71

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Lys
            20                  25                  30

Val Asn Cys Tyr Cys Arg
        35
```

```
<210> SEQ ID NO 72
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 72

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Glu Lys
            20                  25                  30

Met Ser Cys Tyr Cys Arg
        35

<210> SEQ ID NO 73
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 73

Gly Cys Val Arg Leu His Glu Ser Cys Leu Gly Gln Gln Val Pro Cys
1               5                   10                  15

Cys Asp Pro Ala Ala Thr Cys Tyr Cys Val Ser Arg Gly Asp Met Arg
            20                  25                  30

Lys Arg Cys Tyr Cys Arg
        35

<210> SEQ ID NO 74
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 74

Gly Cys Val Arg Leu His Glu Ser Cys Leu Gly Gln Gln Val Pro Cys
1               5                   10                  15

Cys Asp Pro Ala Ala Thr Cys Tyr Cys Glu Arg Arg Gly Asp Ser Val
            20                  25                  30

Lys Lys Cys Tyr Cys Arg
        35

<210> SEQ ID NO 75
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 75

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Thr Arg
            20                  25                  30

Arg Arg Cys Tyr Cys Arg
        35
```

```
<210> SEQ ID NO 76
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 76

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Val
            20                  25                  30

Arg Arg Cys Tyr Cys Arg
        35

<210> SEQ ID NO 77
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 77

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Asn Lys
            20                  25                  30

Arg Lys Cys Tyr Cys Arg
        35

<210> SEQ ID NO 78
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (21)..(21)
<223> OTHER INFORMATION: Xaa may be any amino acid.

<400> SEQUENCE: 78

Gly Cys Val Arg Leu His Glu Ser Cys Leu Gly Gln Gln Val Pro Cys
1               5                   10                  15

Cys Asp Pro Ala Xaa Thr Cys Tyr Cys Lys Gly Arg Gly Asp Val Arg
            20                  25                  30

Arg Val Cys Tyr Cys Arg
        35

<210> SEQ ID NO 79
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 79

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Lys
            20                  25                  30

Val Lys Cys Tyr Cys Arg
        35
```

```
<210> SEQ ID NO 80
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 80

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Arg
            20                  25                  30

Leu Lys Cys Tyr Cys Arg
        35

<210> SEQ ID NO 81
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 81

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Lys Lys Cys Tyr Cys Arg
        35

<210> SEQ ID NO 82
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 82

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Arg
            20                  25                  30

Arg Arg Cys Tyr Cys Arg
        35

<210> SEQ ID NO 83
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 83

Gly Cys Val Arg Leu His Glu Ser Cys Leu Gly Gln Gln Val Pro Cys
1               5                   10                  15

Cys Asp Pro Ala Ala Thr Cys Tyr Cys Gln Gly Arg Gly Asp Gly Asp
            20                  25                  30

Val Lys Cys Tyr Cys Arg
        35
```

```
<210> SEQ ID NO 84
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 84

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
                20                  25                  30

Leu Val Cys Tyr Cys Arg
        35

<210> SEQ ID NO 85
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 85

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
                20                  25                  30

Ile Arg Cys Tyr Cys Arg
        35

<210> SEQ ID NO 86
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 86

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
                20                  25                  30

Leu Val Cys Tyr Cys Arg
        35

<210> SEQ ID NO 87
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 87

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Lys
                20                  25                  30

Met Lys Cys Tyr Cys Arg
        35
```

<210> SEQ ID NO 88
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 88

Gly Cys Val Arg Leu His Glu Ser Cys Leu Gly Gln Gln Val Pro Cys
1               5                   10                  15

Cys Asp Pro Ala Ala Thr Cys Tyr Cys Ile Gly Arg Gly Asp Val Arg
            20                  25                  30

Arg Arg Cys Tyr Cys Arg
        35

<210> SEQ ID NO 89
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 89

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Gly Arg
            20                  25                  30

Lys Lys Cys Tyr Cys Arg
        35

<210> SEQ ID NO 90
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 90

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Arg Asp
            20                  25                  30

Met Lys Cys Tyr Cys Arg
        35

<210> SEQ ID NO 91
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 91

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Glu Lys
            20                  25                  30

Leu Arg Cys Tyr Cys Arg
        35

<210> SEQ ID NO 92
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 92

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Asn
            20                  25                  30

Arg Arg Cys Tyr Cys Arg
        35

<210> SEQ ID NO 93
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 93

Gly Cys Val Arg Leu His Glu Ser Cys Leu Gly Gln Gln Val Pro Cys
1               5                   10                  15

Cys Asp Pro Ala Ala Thr Cys Tyr Cys Glu Ser Arg Gly Asp Val Val
            20                  25                  30

Arg Lys Cys Tyr Cys Arg
        35

<210> SEQ ID NO 94
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 94

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
            20                  25                  30

Leu Arg Cys Tyr Cys Arg
        35

<210> SEQ ID NO 95
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 95
gggtgcgtgg gggggagagg ggattggagc ccgaagtggt gcaaacagga ctccgactgc        60
ccggctggct gcgtttgcgg gcccaacggt ttctgcgga                               99

<210> SEQ ID NO 96
<211> LENGTH: 99
<212> TYPE: DNA
<213> ORGANISM: Artificial sequence
<220> FEATURE:
<223> OTHER INFORMATION: Synthetic polypeptide

```
<400> SEQUENCE: 96
gggtgcacga tcgggagagg ggattgggcc ccctcggagt gcaaacagga ctccgactgc    60
ctggctggct gcgtttgcgg gcccaacggt ttctgcgga                          99

<210> SEQ ID NO 97
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 97
gggtgccacc cgccgagagg ggataacccc cccgtgactt gcaaacagga ctccgactgc    60
ctggctggct gcgtttgcgg gcccaacggt ttctgcgga                          99

<210> SEQ ID NO 98
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 98
gggtgctatc aaggaagagg ggattggtct ccttcatcgt gcaaacagga ctccgactgc    60
ccagctggct gcgtttgcgg gcccaacggt ttctgcgga                          99

<210> SEQ ID NO 99
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 99
gggtgccatg taggaagagg ggattgggct cctgaagagt gcaaacagga ctccgactgc    60
caagctggct gcgtttgcgg gcccaacggt ttctgcgga                          99

<210> SEQ ID NO 100
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 100
gggtgcgatg gaggaagagg ggattgggct cctccagcgt gcaaacagga ctccgactgc    60
cgagctggct gcgtttgcgg gcccaacggt ttctgcgga                          99

<210> SEQ ID NO 101
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 101
gggtgccctc aaggaagagg ggattgggct cctacatcgt gcaaacagga ctccgactgc    60
cgagctggct gcgtttgcgg gcccaacggt ttctgcgga                          99
```

<210> SEQ ID NO 102
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 102
gggtgccctc gaccaagagg ggataaccct cctctaacgt gcaaacagga ctccgactgc    60
ctagctggct gcgtttgcgg gcccaacggt ttctgcgga    99

<210> SEQ ID NO 103
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 103
gggtgccctc aaggaagagg ggattgggct cctgaatggt gcaaacagga ctccgactgc    60
ccagctggct gcgtttgcgg gcccaacggt ttctgcgga    99

<210> SEQ ID NO 104
<211> LENGTH: 99
<212> TYPE: DNA
<213> ORGANISM: Artificial sequence
<220> FEATURE:
<223> OTHER INFORMATION: Synthetic polypeptide

<400> SEQUENCE: 104
gggtgccctc gaggaagagg ggattggtct cctccagcgt gcaaacagga ctccgactgc    60
caagctggct gcgtttgcgg gcccaacggt ttctgcgga    99

<210> SEQ ID NO 105
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 105

Gly Arg Gly Asp Ser Pro
1               5

<210> SEQ ID NO 106
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 106

Pro Leu Pro Arg Gly Asp Asn Pro Pro Thr Glu
1               5                   10

<210> SEQ ID NO 107
<211> LENGTH: 46
<212> TYPE: PRT
<213> ORGANISM: Artificial sequence
<220> FEATURE:
<223> OTHER INFORMATION: Synthetic polypeptide

```
<400> SEQUENCE: 107

Cys Val Arg Leu His Glu Ser Leu Cys Gly Gln Gln Val Pro Cys Cys
1               5                   10                  15

Asp Pro Cys Ala Thr Cys Tyr Cys Arg Phe Phe Asn Ala Phe Cys Tyr
            20                  25                  30

Cys Arg Lys Leu Gly Thr Ala Met Asn Pro Cys Ser Arg Thr
        35                  40                  45

<210> SEQ ID NO 108
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 108

Gly Arg Gly Asp Trp Ala Pro
1               5

<210> SEQ ID NO 109
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 109

Gly Pro Asn Gly
1

<210> SEQ ID NO 110
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 110

Cys Leu Ala Gly
1

<210> SEQ ID NO 111
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 111

Cys Pro Ala Gly
1

<210> SEQ ID NO 112
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 112

Cys Gln Ala Gly
1
```

<210> SEQ ID NO 113
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 113

Cys Arg Ala Gly
1

<210> SEQ ID NO 114
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 114

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
        35

<210> SEQ ID NO 115
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 115

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Ala Arg
            20                  25                  30

Leu Gln Cys Tyr Cys Arg
        35

<210> SEQ ID NO 116
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 116

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asp Asn
            20                  25                  30

Leu Lys Cys Tyr Cys Arg
        35

<210> SEQ ID NO 117
<211> LENGTH: 39
<212> TYPE: PRT
<213> ORGANISM: Artificial sequence
<220> FEATURE:
<223> OTHER INFORMATION: Synthetic polypeptide

```
<220> FEATURE:
<221> NAME/KEY: MISC_FEATURE
<222> LOCATION: (3)..(9)
<223> OTHER INFORMATION: Xaa may be any amino acid.

<400> SEQUENCE: 117

Gly Cys Xaa Xaa Xaa Xaa Xaa Xaa Xaa Cys Leu Gly Gln Gln Val Pro
1               5                   10                  15

Cys Cys Asp Pro Ala Ala Thr Cys Tyr Cys Tyr Gly Arg Gly Asp Asn
            20                  25                  30

Asp Leu Arg Cys Tyr Cys Arg
        35

<210> SEQ ID NO 118
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (10)..(16)
<223> OTHER INFORMATION: Xaa may be any amino acid.

<400> SEQUENCE: 118

Gly Cys Val Arg Leu His Glu Ser Cys Xaa Xaa Xaa Xaa Xaa Xaa Xaa
1               5                   10                  15

Cys Cys Asp Pro Ala Ala Thr Cys Tyr Cys Tyr Gly Arg Gly Asp Asn
            20                  25                  30

Asp Leu Arg Cys Tyr Cys Arg
        35

<210> SEQ ID NO 119
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (18)..(23)
<223> OTHER INFORMATION: Xaa may be any amino acid.

<400> SEQUENCE: 119

Gly Cys Val Arg Leu His Glu Ser Cys Leu Gly Gln Gln Val Pro Cys
1               5                   10                  15

Cys Xaa Xaa Xaa Xaa Xaa Xaa Cys Tyr Cys Tyr Gly Arg Gly Asp Asn
            20                  25                  30

Asp Leu Arg Cys Tyr Cys Arg
        35

<210> SEQ ID NO 120
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 120

Ala Ser Gly Ser Gly Asp Pro
1               5
```

```
<210> SEQ ID NO 121
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 121

Arg Pro Leu Gly Asp Ala Gly
1               5

<210> SEQ ID NO 122
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 122

Leu Ala Gly Leu Ser Gly Pro
1               5

<210> SEQ ID NO 123
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 123

Arg Ser Ala Ser Val Gly Gly
1               5

<210> SEQ ID NO 124
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 124

Ile Ala Ser Gly Leu Phe Gly
1               5

<210> SEQ ID NO 125
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 125

Asp Leu Tyr Gly Ser His Asp
1               5

<210> SEQ ID NO 126
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 126

Gly Gly Ser Val Gly Val Glu
1               5
```

<210> SEQ ID NO 127
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 127

Asp Pro Arg Val Gly Val Arg
1               5

<210> SEQ ID NO 128
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 128

Ala Asp Thr Leu Met Ala Ala
1               5

<210> SEQ ID NO 129
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 129

Glu Trp Gly Arg Gly Gly Asp
1               5

<210> SEQ ID NO 130
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 130

Gly Ser Trp Gly Thr Leu Ala
1               5

<210> SEQ ID NO 131
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 131

Trp Gly Ser Ile Leu Gly His
1               5

<210> SEQ ID NO 132
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 132

Gly Thr Pro Lys Pro Glu
1               5

```
<210> SEQ ID NO 133
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 133

Ser Arg Ser Asp Ala His
1               5

<210> SEQ ID NO 134
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 134

Ser Gly Leu Gly Asn Arg
1               5

<210> SEQ ID NO 135
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 135

Gln Gly Arg Glu Gln Ser
1               5

<210> SEQ ID NO 136
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 136

Thr Val Thr Asn Ser Arg
1               5

<210> SEQ ID NO 137
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 137

Thr Ser Lys Gln His His
1               5

<210> SEQ ID NO 138
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 138

Asp Tyr Lys Asp Asp Asp Asp Lys
1               5
```

```
<210> SEQ ID NO 139
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 139

Ser Ala Gly Thr
1

<210> SEQ ID NO 140
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: This amino acid may be D-Tyr.

<400> SEQUENCE: 140

Arg Gly Asp Tyr Lys
1               5
```